(12) United States Patent
Himmler et al.

(10) Patent No.: US 9,133,274 B2
(45) Date of Patent: Sep. 15, 2015

(54) METHOD FOR ENGINEERING IMMUNOGLOBULINS

(75) Inventors: Gottfried Himmler, Gross-Enzersdorf (AT); Gerda Redl, Gross-Enzersdorf (AT); Florian Ruker, Vienna (AT); Gordana Wozniak-Knopp, Vienna (AT)

(73) Assignee: F-star Biotechnologische Forschungs-und Entwicklungsges.m.b.H, Vienna (AT)

( * ) Notice: Subject to any disclaimer, the term of this patent is extended or adjusted under 35 U.S.C. 154(b) by 1000 days.

(21) Appl. No.: 12/307,569

(22) PCT Filed: Jul. 5, 2007

(86) PCT No.: PCT/AT2007/000343
§ 371 (c)(1),
(2), (4) Date: Sep. 21, 2009

(87) PCT Pub. No.: WO2008/003116
PCT Pub. Date: Jan. 10, 2008

(65) Prior Publication Data
US 2010/0029497 A1  Feb. 4, 2010

(30) Foreign Application Priority Data
Jul. 5, 2006  (AT) ................... A 1145/2006

(51) Int. Cl.
  *C07K 16/24* (2006.01)
  *C07K 16/10* (2006.01)
  *C07K 16/16* (2006.01)
  *C07K 16/32* (2006.01)
  *C07K 16/40* (2006.01)

(52) U.S. Cl.
  CPC .......... *C07K 16/241* (2013.01); *C07K 16/1063* (2013.01); *C07K 16/16* (2013.01); *C07K 16/32* (2013.01); *C07K 16/40* (2013.01); *C07K 2317/21* (2013.01); *C07K 2317/22* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,475,100 A * | 12/1995 | Hashino et al. ............ 536/23.53 |
| 5,723,323 A | 3/1998 | Kauffman et al. |
| 5,763,192 A | 6/1998 | Kauffman et al. |
| 5,814,476 A | 9/1998 | Kauffman et al. |
| 5,817,483 A | 10/1998 | Kauffman et al. |
| 5,824,514 A | 10/1998 | Kauffman et al. |
| 6,352,842 B1 | 3/2002 | Short et al. |
| 6,358,709 B1 | 3/2002 | Short et al. |
| 6,361,974 B1 | 3/2002 | Short et al. |
| 6,562,617 B1 | 5/2003 | Anderson et al. |
| 6,602,684 B1 | 8/2003 | Umana et al. |
| 2005/0054832 A1 | 3/2005 | Lazar et al. |
| 2005/0244403 A1 | 11/2005 | Lazar et al. |
| 2005/0255548 A1* | 11/2005 | Lipovsek et al. ............ 435/69.1 |
| 2005/0266000 A1 | 12/2005 | Bond et al. |

FOREIGN PATENT DOCUMENTS

| | | |
|---|---|---|
| EP | 0640130 B1 | 4/1998 |
| EP | 1752471 | 2/2007 |
| WO | WO 9308278 | 4/1993 |
| WO | WO93/23537 A1 | 11/1993 |
| WO | WO 9323537 | 11/1993 |
| WO | WO 9622377 | 7/1996 |
| WO | WO 9734631 | 9/1997 |
| WO | WO 00/42561 | 7/2000 |
| WO | WO 01/70947 | 9/2001 |
| WO | WO 0188159 | 11/2001 |
| WO | WO 0244215 A1 | 6/2002 |
| WO | WO 02060919 | 8/2002 |
| WO | WO 03012100 | 2/2003 |
| WO | WO 2004018674 | 3/2004 |
| WO | WO 2004041862 | 5/2004 |
| WO | WO 2006036834 A2 * | 4/2006 |
| WO | WO2006/072620 A1 | 7/2006 |
| WO | WO 2006072620 A1 | 7/2006 |

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin-binding and mitogenic activities of heparin-binding (acidic fibroblast) growth factor 1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activites. Molecular and Cellular Biology, 1988. vol. 8, pp. 1247-1252.*

Salfeld. Isotype selection in antibody engineering. Nature Biotechnology, 2007. vol. 25, pp. 1369-1372.*

(Continued)

*Primary Examiner* — Brad Duffy
(74) *Attorney, Agent, or Firm* — Sunstein Kann Murphy & Timbers LLP

(57) ABSTRACT

A method for engineering an immunoglobulin having a variable domain and at least one modification in at least two structural loops of the immunoglobulin and determining the binding of the immunoglobulin to an epitope of an antigen, where the unmodified immunoglobulin does not significantly bind to said epitope, comprising the steps of providing a nucleic acid encoding an immunoglobulin having at least two structural loops, modifying at least one nucleotide residue of each of the structural loops, transferring the modified nucleic acid in an expression system, expressing the modified immunoglobulin, contacting the expressed modified immunoglobulin with an epitope, and determining whether the modified immunoglobulin binds to the epitope.

38 Claims, 8 Drawing Sheets

(56) References Cited

OTHER PUBLICATIONS

Dall'Acqua, Cook, Damschroder, Woods, and Wu. Modulating the effector functions of a human IgG1 through engineering of its hinge region. Journal of Immunology, 2006. vol. 177, pp. 1129-1138.*
Bork et al.(1994) J. Mol. Biol. 242:309-320.
Halaby et al. (1999) Protein Engineering 12: 563-571.
Carter et al. Biotechnology (N Y). Feb. 1992;10(2):163-167.
Nygren PA, Uhlen M., Curr Opin Struct Biol. (1997) 7:463-469.
Binz HK, Amstutz P, Kohl A, Stumpp MT, Briand C, Forrer P, Grutter MG, Pluckthun A. Nat Biotechnol. (2004) 22:575-582.
Vogt M, Skerra A. Chembiochem. (2004) 5:191-199.
Hufton et al. FEBS Letters (2000) 475: 225.
Binz et al. Nat Biotechnol. (2005) 23:1257-1268.
Hosse et al. Protein Sci. (2006)15:14-27.
Holliger & Hudson, Nat. Biotechnol. (2005) 23:1126-1136.
Hoogenboom, Nat. Biotechnol. (2005)23:1105-1116.
Jones et al. Nature (1986) 321: 522-525.
Kashmiri et al. Methods (2005) 36:25-34.
Ewert et al. Methods (2004) 34:184-199.
Conrath et al. J Mol Biol. (2005) 350:112-125.
Dottorini et al. Biochemistry (2004) 43:622-628.
Masuda et al. FEBS J. (2006) 273:2184-2194.
Foote & Winter (1992) J. Mol. Biol. 224: 487-499.
Kettleborough et al. Protein Eng. (1991) 4:773-783.
Wu et al. J. Mol. Biol. (1999) 294:151-162.
Simon & Rajwesky, Protein Eng. (1992) 5:229-234.
Laffly et al (2005) Hum Antibodies. 2005;14(1-2):33-55.
Lefranc et al., 1999, Nucleic Acids Res. 27: 209-212.
Ruiz et al., 2000 Nucleic Acids Res. 28: 219-221.
Lefranc et al., 2001, Nucleic Acids Res. 29: 207-209.
Lefranc et al., 2003, Nucleic Acids Res. 31: 307-310.
Lefranc et al., 2005, Dev Comp Immunol 29:185-203.
Altschul et al., Methods in Enzymology 266:460-480 (1996).
Yanez et al. Nucleic Acids Res. (2004) 32:e158.
Virnekas et al. Nucleic Acids Res. (1994) 22:5600-5607.
Lea & Stewart (1995) FASEB J. 9:87-93.
Fellhouse et al. (2006) J. Mol. Biol. 357:100-114.
Adib-Conquuy et al. (1998) International Immunology 10:341-346.
Lo Conte et al. (1999) J. Mol. Biol. 285:2177-2198.
Zemlin et al. (2003) J. Mol. Biol. 334:733-749.
Hayhurst & Georgiou, 2001, Curr Opin Chem Biol 5:683-689.
Maynard & Georgiou, 2000, Annu Rev Biomed Eng 2:339-376.
Lowman et al., 1991, Biochemistry 30:10832-10838.
Smith, 1985, Science 228:1315-1317.
Malmborg et al., 1997, J Mol Biol 273:544-551.
Krebber et al., 1997, J Mol Biol 268:619-630.
Benhar et al., 2000, J Mol Biol 301:893-904.
Witrrup, 2001, Curr Opin Biotechnol, 12:395-399.
Boder Eric T., et al; "Directed Evolution of Antibody Fragments with Monovalent Femtomolar Antigen-binding Affinity", Proceedings of the National Academy of Sciences of USA, National Academy of Science, Washington, DC, US, vol. 97, No. 20, Sep. 26, 2000, pp. 10701-10705; XP002185398 ISSN: 0027-8424.
Simon T. et al.; "A Functional Antibody Mutant With an Insertion in the Framework Region 3 Loop of the V-H Domain Implications for Antibody Engineering", Protein Engineering, Oxford University Press, Surrey, GB, vol. 5, No. 3, 1992, pp. 229-234, XP008083103 ISSN: 0269-2139.
PCT/AT2007/000343, International Filing Date: Jul. 5, 2007; Priority Date: Jul. 5, 2006; International Preliminary Report on Patentability dated Jan. 15, 2009.
Dirk Saerens, et al., Identification of a Universal VHH Framework to Graft Non-canonical Antigen-binding Loops of Camel Single-domain Antibodies, J. Mol. Biol. (2005), 352, 597-607.
Katja Conrath, et al., Antigen Binding and Solubility Effects upon the Veneering of a Camel VHH in Framework-2 to Mimic a VH, J. Mol. Biol. (2005) 350, 112-125.
Jefferson Foote and Greg Winter, Antibody Framework Residues Affecting the Conformation of the Hypervariable Loops, J. Mol. Biol. (1992) 224, 487-490.
Boder & Wittrup, 1997, Nat Biotechnol 15:553-557.
Whitehorn et al., 1995, Biotechnology 13:1215-1219.
Boder & Wittrup, 2000, Methods Enzymol 328:430-44.
Jung et al., 1998, Nat Biotechnol 16:576-80.
Lee et al., 2000, Nat Biotechnol 18:645-648.
Georgiou et al., 1993, Trends Biotechnol 11:6-10.
Georgiou et al., 1997, Nat Biotechnol 15:29-34.
Amstutz et al., 2001, Curr Opin Biotechnol 12:400-405.
Mattheakis et al., 1994, Proc Natl Acad Sci USA 91:9022-9026.
Hanes et al., 1997, Proc Natl Acad Sci USA 94:4937-4942.
Roberts & Szostak, 1997, Proc Natl Acad Sci USA 94:12297-12302.
Nemoto et al., 1997, FEBS Lett 414:405-408.
Zhou et al., 2002, J Am Chem Soc 124, 538-543.
Chen et al., 2001, Nat Biotechnol 19:537-542.
Johnsson & Varshavsky, 1994, Proc Natl Acad Sci USA 91:10340-10344.
Pelletier et al., 1998, Proc Natl Acad Sci USA 95:12141-12146.
Fields & Song, 1989, Nature 340:245-246.
Visintin et al., 1999, Proc Natl Acad Sci USA 96:11723-11728.
Kolkman & Stemmer, 2001, Nat Biotechnol 19:423-428.
Crameri et al., 1998, Nature 391:288-291.
Coco et al., 2001, Nat Biotechnol 19:354-359.
Zhao et al., 1998, Nat Biotechnol 16:258-261.
Shao et al., 1998, Nucleic Acids Res 26:681-683.
Lutz et al., 2001, Proc Natl Acad Sci USA 98:11248-11253.
Kikuchi et al., 2000, Gene 243:133-137.
Auf der Maur, 2004, Methods, 34:215-224.
Koren et al., 2002, Current Pharmaceutical Biotechnology 3:349-360.
Chirino et al., 2004, Drug Discovery Today 9:82-90.
Tangri et al., 2005, J. Immunol. 174:3187-3196.
Hermeling et al., 2004, Pharm. Res. 21:897-903.
de Jager et al., Clin. Diagn. Lab. Immunol., 2003, 10:133-139.
Schmittel et. al., 2000, J. Immunol. Meth., 24: 17-24.
Kufer et al. (2004) Trends in Biotechnology vol. 22 pp. 238-244.
Carter (2001) Journal of Immunological Methods, vol. 248, pp. 7-15.
LeGall et al. (2004) Protein Engineering, Design & Selection vol. 17 pp. 357-366.
Cabilly et al. Proc. Natl. Acad. Sci. USA 81:3273-3277 (1984).
Berntzen et al., 2006, Protein Eng Des Sel. 19(3):121-128.
Berntzen et al., 2005, J Immunol Methods. 298(1-2):93-104.
Lauvrak et al. 1997 Biol Chem. 378(12):1509-1519.
Dall' Acqua et al. Journal of Immunology, 2002, 169: 5171-5180.
Hoover DM, Lubkowski J., Nucleic Acids Res. May 15, 2002;30(10):e43.
Hoogenboom HR, Griffiths AD, Johnson KS, Chiswell DJ, Hudson P, Winter G. Multi-subunit proteins on the surface of filamentous phage: methodologies for displaying antibody (Fab) heavy and light chains. Nucleic Acids Res. Aug. 11, 1991;19(15):4133-4137.
Huston et al. (1988) Proc Natl Acad Sci U S A. 85:5879-5883.
Schaffitzel et al. (1999) J Immunol Methods 231:119-135.
Kang et al., Proc Natl Acad Sci U S A. May 15, 1991;88(10):4363-4366.
Kang et al., Clin Vaccine Immunol. Aug. 2006;13(8):953-957.
Weaver-Feldhaus et al., FEBS Lett. Apr. 23, 2004;564(1-2):24-34.
Cho et al., Nature. Feb. 13, 2003;421(6924):756-760.
Boder et al., Proceedings of the National Academy of Science; vol. 97, No. 20, Sep. 2000, p. 10701-10705.
Saerens et al., Journal of Molecular Biology, 2005, vol. 352, No. 3, p. 597-607.

* cited by examiner

```
Query   2    VQLQESGGGLVQPGGSLRLSCAASGRTFSDHSGYTYTIGWFRQAPGKEREEVARIYWSSG  61
             VQL ESGGG VQ GGSLRLSCAASG         S +   +GWFRQAPGKERE VA + + G
Sbjct   2    VQLVESGGGSVQAGGSLRLSCAASGYIASINY-----LGWFRQAPGKEREGVAAVSPAGG  56

Query   62   NTYYADSVKGRFAISRDIAKNTVDLTMNNLEPEDTAVYYC-AARDGIPTSRSVESYNYWG  120
              + +S  D A+NTV L MN+L+PEDTA+YYC AAR G      +     YNYWG
Sbjct   57   TPYYADSVKGRFTVSLDNAENTVYLQMNSLKPEDTALYYCAAAARQGWYIPLNSYGYNYWG  116

Query   121  QGTQVTVSS  129
             QGTQVTVSS
Sbjct   117  QGTQVTVSS  125
```

Figure 1

```
     P  W  Q  V  Q  L  Q  E  S  G  G  G  L  V  Q  P  G  G  S  L  R  L  S  C  A  A  S  G  R  T  F  S  D
  1 CCATGGCAAG TTCAGCTGCA GGAAAGCGGT GGCGGCCTGG TCCAGCCTGG CGGCAGCCTG CGTCTGAGCT GTGCGGCCAG CGGCCGTACC TTTAGCGACC
    GGTACCGTTC AAGTCGACGT CCTTTCGCCA CCGCCGGACC AGGTCGGACC GCCGTCGGAC GCAGACTCGA CACGCCGGTC GCCGGCATGG AAATCGCTGG

H  S  G  Y  T  Y  T  I  G  W  F  R  Q  A  P  G  K  E  R  E  F  V  A  R  I  Y  W  S  S  G  N  T  Y  Y
 101 ATAGCGGCTA CACCTATACC ATTGGCTGGT TTCGTCAGGC GCCAGGAAAA GAACGTGAAT TTGTGGCGCG TATTTACTGG AGCAGCGGCA ATACCTATTA
     TATCGCCGAT GTGGATATGG TAACCGACCA AAGCAGTCCG CGGTCCTTTT CTTGCACTTA AACACCGCGC ATAAATGACC TCGTCGCCGT TATGGATAAT

A  D  S  V  K  G  R  F  A  I  S  R  D  I  A  K  N  T  V  D  L  T  M  N  N  L  E  P  E  D  T  A  V
 201 TGCGGATAGC GTGAAAGGCC GTTTCGCGAT TAGCCGCGAC ATTGCCAAGA ACACGGTAGA TCTTACGATG AACAACCTGG AGCCCGAAGA CACAGCCGTG
     ACGCCTATCG CACTTTCCGG CAAAGCGCTA ATCGGCGCTG TAACGGTTCT TGTGCCATCT AGAATGCTAC TTGTTGGACC TCGGGCTTCT GTGTCGGCAC

Y  Y  C  A  A  R  D  G  I  P  T  S  R  S  V  E  S  Y  N  Y  W  G  Q  G  T  Q  V  T  V  S  S  A  A
 301 TATTATTGCG CGGCTCGGGA TGGCATTCCG ACCAGCCGTA GCGTGGAAAG CTACAATTAC TGGGGCCAGG GCACCCAGGT GACCGTCAGC TCTGCGGCCG
     ATAATAACGC GCCGAGCCCT ACCGTAAGGC TGGTCGGCAT CGCACCTTTC GATGTTAATG ACCCCGGTCC CGTGGGTCCA CTGGCAGTCG AGACGCCGGC

SEQ ID NO. 55 and SEQ ID NO. 56

```
     P  W  R  I  T  L  K  E  S  G  P  P  L  V  K  P  T  Q  T  L  T  L  T  C  S  F  S  G  F  S  L  S  D
+3   CCATGGGGA TCACCCTGAA AGAGAGTGGA CCCCCCCTGG TGAAACCTAC CCAGACCCTG ACTCTGACTT GCTCATTTAG CGGCTTTAGC CTGAGCGATT
  1  GGTACCCCCT AGTGGGACTT TCTCTCACCT GGGGGGGACC ACTTTGGATG GGTCTGGGAC TGAGACTGAA CGAGTAAATC GCCGAAATCG GACTCGCTAA

F  G  V  G  V  G  W  I  R  Q  P  P  G  K  A  L  E  W  L  A  I  I  Y  S  D  D  D  K  R  Y  S  P  X  X
+3   TTGGCGTCGG CGTTGGTTGG ATTCGCCAGC CTCCCGGCAA AGCCCTGGAA TGGCTGGCCA TCATCTACTC CGATGATGAC AAGCGTTATA GCCCCNNSNN
101  AACCGCAGCC GCAACCAACC TAAGCGGTCG GAGGGCCGTT TCGGGACCTT ACCGACCGGT AGTAGATGAG GCTACTACTG TTCGCAATAT CGGGAGCGA

X  X  X  L  T  I  T  K  D  T  S  K  N  Q  V  V  L  V  M  X  X  V  S  P  V  D  T  A  T  Y  F  C  A
+3   SNNSNNSNNS CTGACCATCA CCAAAGATAC GAGCAAGAAC CAGGTGGTTT TGGTAATGNN SNNSGTGAGC CCCGTCGACA CCGCGACTTA TTTCTGTGCC
201  SNNSNNSNNS GACTGGTAGT GGTTTCTATG CTCGTTCTTG GTCCACCAAA ACCATTACTG GCCACACTCG GGGCAGCTGT GGCGCTGAAT AAAGACACGG

H  R  R  G  P  T  T  L  F  G  V  P  I  A  R  G  P  V  N  A  M  D  V  W  G  Q  G  I  T  V  T  I  S
+3   CATCGTCGTG CCTGTTTGGT GTCCACCAC CTTGTTCGGT GTGCCGATTG CACGCGGTCC CGTGAATGCG ATGGATGTGT GGGGGCCAGG GATTACCGTG ACCATTTCAT
301  GTAGCAGCAC GGACAAACCA CAGGCTGGTG GAACAAACCA CACGGCTAAC GTGCGCCAGG GCACTTACGC TACCTACACA CCCCGGTCCC CTAATGGCAC TGGTAAAGTA

S  G  G  G  G  S  G  G  G  G  S  G  G  G  G  S  A  L  Q  L  T  Q  S  P  S  S  L  S  A  S  V  G  D  R
+3   CCGGTGGAGG TGGTAGTGGA GGGGGTGGGT CAGGCGGTGG GGGTGGTTCG CGGCTCCGCC TTACAACTGA CCAGAGCCC GTCTAGTTTG AGCGCAAGCG TGGGCGATCG
401  GGCCACCTCC ACCATCACCT CCCCCACCCA GTCCGCCACC GCCGAGGCGG AATGTTGACT GGTCTCGGG CAGATCAAAC TCGCGTTCGC ACCCGCTAGC

I  T  I  T  C  R  A  S  Q  G  V  T  S  A  L  A  W  Y  R  Q  Q  L  L  I  Y  D  A
+3   TATTACAATT ACCTGTCGGG CGAGCCAAGG TGTTACCTCC GCCCTGGCCT GGTATCCTCA GAAACCCGGG AGTTGTGAT CTACGATGCG
501  ATAATGTTAA TGGACAGCCC GCTCGGTTCC ACAATGGAGG CGGGACCGGA CCATAGCAGT CTTTGGGCCC TCAACAACTA GATGCTACGC

S  S  L  E  S  G  V  P  S  R  F  S  G  S  G  S  G  T  E  F  T  L  T  I  S  T  L  R  P  E  D  F  A
+3   TCCTCACTGG AATCAGGGGT CCCTAGCCGC TTTTCCGGGT CCGGCAGCGG SGGCAGCGGG ACGGAATTT ACATTGACCA TAAGCACCCT GCGTCCGGAA GATTTTGCCA
601  AGGAGTGACC TTAGTCCCCA GGGATCGGCG AAAAGGCCCA GGCCGTCGCC GCCGTCGCC TGCCTTAAA TGTAACTGGT ATTCGTGGGA CGCAGGCCTT CTAAAACGGT

T  Y  Y  C  Q  Q  L  H  F  Y  P  H  T  F  G  G  G  T  R  V  D  V  R  R  T  V  A  A  A  A
+3   CCTATTATTG CACTTTTATC CCCATACCTT CGGTGGGGGG ACGCGGGTTG ACGTGCGTCG TACCTAGCT GCTGCGGCCG
701  GGATAATAAC GTGAAATAG GGGTATGGAA GCCACCCCCC TGCGCCCAAC TGCACGCAGC ATGGCATCGA CGACGCCGGC
```

Figure 5

SEQ ID NO. 57 and SEQ ID NO. 58

```
       P   W   R     I   T   L   K     E   S   G     P   P   X     X   X   P   X     X   X   X   L     T   L   T     C   S   F   S     G   F   S     L   S   D
 +3    CCATGGCGGA  TCACCCTGAA  AGAGAGTGGA  CCCCCCNNSN  NSNNSCCTNN  SNNSNNSCTG  ACTCTGACTT  GCTCATTTAG  CGGCTTTAGC  CTGAGCGATT
   1   GGTACCGCCT  AGTGGGACTT  TCTCTCACCT  GGGGGGNNSN  ACTTTGGATG  GGTCTGGGAC  TGAGACTGAA  CGAGTAAATC  GCCGAAATCG  GACTCGCTAA

F   G   V   G     V   G   W     I   R   Q     P   P   G   K     A   L   E     W   L   A     I   I   Y   S     K   R   Y     S   P   S   L
 +3    TTGGCGTCGG  CGTTGGTTGG  ATTCGCCAGC  CTCCCGGCAA  AGCCCTGGAA  TGGCTGGCCA  TCATCTACTC  CGATGATGAC  AAGCGTTATA  GCCCCTCGCT
 101   AACCGCAGCC  GCAACCAACC  TAAGCGGTCG  GAGGGCCGTT  TCGGGACCTT  ACCGACCGGT  AGTAGATGAG  GCTACTACTG  TTCGCAATAT  CGGGGAGCGA

N   T   R     L   T   I     T   K   D   T     S   K   N     Q   V   V     L   V   M   X     X   V   S     T   A   T   Y     F   C   A
 +3    GAATACCCGT  CTGACCATCA  CCAAAGATAC  GAGCAAGAAC  CAGGTGGTTT  TGGTAATGNN  SNNSGTGAGC  CCCGTCGACA  TTTCTGTGCC
 201   CTTATGGGCA  GACTGGTAGT  GGTTTCTATG  CTCGTTCTTG  GTCCACCAAA  ACCATTACTG  SNNSCACTCG  GGGCAGCTGT  AAAGACACGG

H   R   R     G   P   T   I     L   F   G     V   P   I     A   R   G   P     V   N   A     M   D   V     I   T   V     T   I   S
 +3    CATCGTCGTG  GTCCGACCAC  CCTGTTTGGT  GTGCCGATTG  CACGCGGTCC  CGTGAATGCC  ATGGATGTGT  GATTACCGTG  ACCATTTCAT
 301   GTAGCAGCAC  CAGGCTGGTG  GGACARAACCA  CACGGCTAAC  GTGCGCCAGG  GCACTTACGG  TACCTACACA  CCCCCGTCCC  CTAATGGCAC  TGGTAAAGTA

S   G   G   G     G   S   G     G   G   G     S   G   G   G     S   A     L   Q   L     T   Q   S   P     S   S   L     S   A   S     V   G   D   R
 +3    TCCGGTGGAG  TGGTAGTGGA  GGGGGGTGGG  CAGGGTGGGT  CGGCTCCGCC  CGGCAGTGA  TTACAACTGA  CGCAGAGCCC  GTCTAGTTTG  AGCGCAAGCG  TGGGCGATCG
 401   AGGCCACCTC  ACCATCACCT  CCCCCACCCA  GTCCGACCAC  GCCGAGGCCG  AATGTTGACT  GCGTCTCGGG  CAGATCAAAC  TCCGGTTCGC  ACCGCTAGC

I   T   I     T   C   R     A   S   Q   G     V   T   S     Q   G     A   L   A     W   Y   R   Q     K   P   G     S   P   P     Q   L   L   I     Y   D   A
 +3    TATTACAATT  ACCTGTCGGG  CGAGCCAAGG  TGTTACCTCC  CAATGA  GCCCTGGCCT  GGTATCGTCA  GAAACCCGGG  AGCCCGCCAC  AGTTGTTGAT  CTACGATGCG
 501   ATAATGTTAA  TGGACAGCCC  GCTCGGTTCC  ACAATGGAGG  GTTACT  CGGGACCGGA  CCATAGCAGT  CTTTGGGCCC  TCGGGCGGTG  TCAACAACTA  GATGCTACGC

S   S   L     E   S   G   V     P   S   R     F   S   G     S   G   S   G     T   E   F     T   L   T     I   S   T   L     R   P   E     D   F   A
 +3    TCCTCACTGG  AATCAGGGGT  CCCTAGCCGC  TTTTCCGGGT  CCGGCAGCGG  CACGGAATTT  ACATTGACCA  TAAGCACCCT  CGTCCGGAA  GATTTTGCCA
 601   AGGAGTGACC  TTAGTCCCCA  GGGATCGGCG  AAAAGGCCCA  GGCCGTCGCC  GTGCCTTAAA  TGTAACTGGT  ATTCGTGGGA  CGCAGGCCTT  CTAAAACGGT

T   Y   Y   C     Q   Q   L     P   H   T   F     G   G   G     T   R   V     D   V   R   R     T   V   A     A   A   A
 +3    CCTATTATTG  CCAACAGCTG  CACTTTTATC  CCCATACCTT  CGGTGGGGGG  ACCCGGGTTG  ACGTGCGTCG  TACCGTAGCT  GCTGCGGCCG  C
 701   GGATAATAAC  GGTTGTCGAC  GTGAAAATAG  GGGTATGGAA  GCCACCCCCC  TGGGCCCAAC  TGCACGCAGC  ATGGCATCGA  CGACGCCGGC  G
```

Figure 6

SEQ ID NO. 59 and SEQ ID NO. 60

```
+3    P  W  R    I  T  L  K    E  S  G    P  P  X    X  X  P  X    X  X  L    T  L  T    C  S  F  S    G  F  S    L  S  D
  1   CCATGGCGGA TCACCCTGAA AGAGAGTGGA CCCCCCNNSN NSNNSCCTNN SNNSNNSCTG ACTCTGACTT GCTCATTTAG CGGCTTTAGC CTGAGCGATT
      GGTACCGCCT AGTGGGACTT TCTCTCACCT GGGGGGACCC ACTTTGGATG GTTCTGGGAC TGAGACTGAA CGAGTAAATC GCCGAAATCG GACTCGCTAA

+3    F  G  V  G    V  G  W    I  R  Q    P  P  G  K    A  L  E  W    L  A    I  I  Y  S    D  D  D    K  R  Y    S  P  X  X
101   TTGGCGTCGG CGTTGGTTGG ATTCGCCAGC CTCCCGGCAA AGCCCTGGAA TGGCTGGCCA TCATCTACTC CGATGATGAC AAGCGTTATA GCCCCNNSNN
      AACCGCAGCC GCAACCAACC TAAGCGGTCG GAGGGCCGTT TCGGGACCTT ACCGACCGGT AGTAGATGAG GCTACTACTG TTCGCAATAT CGGGGAGCGA

+3    X  X  X    L  T  I    T  K  D  T    S  K  N    Q  V  V    L  V  M  X    X  V  S    S  N  N  S  G  T  G  A  G  C    P  V  D    T  A  T  Y    F  C  A
201   SNMSNMSNNS CTGACCATCA CCAAAGATAC GAGCAAGAAC CAGGTGGTTT TGGTAATGNN SNNSGTGAGC CCCGTCGACA CCGCGACTTA TTTCTGTGCC
      CTTATGGGCA GACTGGTAGT GGTTTCTATG CTCGTTCTTG GTCCACCAAA ACCATTACTG GGCACACTCG GGGCAGCTGT GGCGCTGAAT AAAGACACGG

+3    H  R  R    G  P  T  T    L  F  G    V  P  I    A  R  G  P    V  N  A    M  D  V    W  G  Q  Q    I  T  V    T  I  S
301   CATCGTCGTG GTCCGACCAC CCTGTTTGGT GTCCCGATTG CACGCGGTCC CGTGAATGCG ATGGATGTGT GGGGGCAGGG GATTACCGTG ACCATTTCAT
      GTAGCAGCAC CAGGCTGGTG GGACAAACCA CAGGGCTAAC GTGCGCCAGG GCACTTACGC TACCTACACA CCCCCGTCCC CTAATGGCAC TGGTAAAGTA

+3    S  G  G  G    G  S  G    G  G  G  S    G  G  G    S  G  A    L  Q  L  T    Q  S  P    S  S  L    S  A  S    V  G  D  R
401   CCGGTGGAGG TGGTAGTGGA GGGGGTGGGT CAGGGCGGTGG CGGCTCCGCC TTACAACTGA CCCAGAGCCC GTCTAGTTTG AGCGCAAGCG TGGGCGATCG
      GGCCACCTCC ACCATCACCT CCCCCACCCA GTCCGCCACC GCCGAGGCGG AATGTTGACT GGGTCTCGGG CAGATCAAAC TCGCGTTCGC ACCCGCTAGC

+3    I  T  I    T  C  R    A  S  Q  G    V  T  S    A  L  A    W  Y  R  Q    K  P  G    Q  L  L  I    Y  D  A
501   TATTACAATT ACCTGTCCGG CCAGCCAAGC TGTTACCTCC GCCCTGGCCT GGTATCGCCA GAAACCCGGC AGTTGTTGAT CTACGATGCG
      ATAATGTTAA TGGACAGGCC GGTCGGTTCG ACAATGGAGG CGGGACCGGA CCATAGCAGT CTTTGGGCCG TCAACAACTA GATGCTACGC

+3    S  S  L    E  S  G  V    P  S  R    F  S  G    S  G  S  G    T  E  F    T  L  T    I  S  T  L    R  P  E    D  F  A
601   TCCTCACTCG AATCAGGGGT CCCTAGCCGC TTTTCCGGGT CCGGCAGCGG CACGGAATTT ACATTGACCA TAAGCACCCT GCGTCCGGAA GATTTTGCCA
      AGGAGTGACC TTAGTCCCCA GGGATCGGCG AAAAGGCCCA GGCCGTCGCC GTGCCTTAAA TGTAACTGGT ATTCGTGGGA CGCAGGCCTT CTAAAACGGT

+3    T  Y  Y  C    Q  Q  L    H  F  Y    P  H  T  F    G  G  G    T  R  V    D  V  R  R    T  V  A    A  A  A
701   CCTATTATTG CCAACAGCTG CACTTTTATC CCCATACCTT CGGTGGGGGG ACGCGGGTTG ACGTGCGTCG TACCGTAGCT GCTGCGGCCC C
      GGATAATAAC GGTTGTCGAC GTGAAAATAG GGGTATGGAA GCCACCCCCC TGCGCCCAAC TGCACGCAGC ATGGCATCGA CGACGCCGGG G
```

Figure 7

SEQ ID NO. 61 and SEQ ID NO. 62

```
+3       P   W   R   I   T   L   K   E   S   G   P   P   L   V   K   P   T   Q   T   L   T   C   S   F   S   G   F   S   L   S   D
  1   CCATGGCGGA TCACCCTGAA AGAGAGTGGA CCCCCCCTGG TGAAACCTAC CCAGACCCTG ACTCTGACTT GCTCATTTAG CGGCTTTAGC CTGAGCGATT
      GGTACCGCCT AGTGGGACTT TCTCTCACCT GGGGGGGACC ACTTTGGATG GGTCTGGGAC TGAGACTGAA CGAGTAAATC GCCGAAATCG GACTCGCTAA

+3       F   G   V   G   V   G   W   I   R   Q   P   P   G   K   A   L   E   W   L   A   I   L   Y   S   D   D   D   K   R   Y   S   P   S   L
101   TTGGCCGTCGG CGTTGGTTGG ATTCGCCAGC CTCCCGGCAA AGCCCTGGAA TGGCTGGCCA TCATCTACTC CGATGATGAC AAGGTTATA GCCCCTCGCT
      AACCGGCAGCC GCAACCAACC TAAGCGGTCG GAGGGCCGTT TCGGGACCTT ACCGACCGGT AGTAGATGAG GCTACTACTG TTCGCAATAT CGGGGAGCGA

+3       N   T   R   L   T   I   I   T   K   D   T   S   K   N   Q   V   V   L   V   M   T   R   V   S   T   A   T   Y   F   C   A
201   GAATACCCGT CTGACCATCA CCAAAGATAC GAGCAAGAAC CAGGTGGTTT TGGTAATGAC CCGTGTGAGC ACCGCGACTTA TTTCTGTGCC
      CTTATGGGCA GACTGGTAGT GGTTTCTATG CTCGTTCTTG GTCCACCAAA ACCATTACTG GGCACACTCG TGGCGCTGAAT AAAGACACGG

+3       H   R   R   G   P   T   L   F   G   V   P   I   A   R   G   P   V   N   A   M   D   V   W   G   Q   G   I   T   V   T   I   S
301   CATCGTCGTG GTCCGACCAC CCTGTTTGGT GTGCCGATTG CACGCGGTCC CGTGAATGCG ATGGATGTGT GGGGGCAGGG GATTACCGTG ACCATTTCAT
      GTAGCAGCAC CAGGCTGGTG GGACAAACCA CACGGCTAAC GTGCGCCAGG GCACTTACGC TACCTACACA CCCCCGTCCC CTAATGGCAC TGGTAAAGTA

+3       S   G   G   G   G   S   G   G   G   G   S   G   G   G   G   S   L   T   Q   S   P   S   A   S   V   G   D   R
401   CCGGTGGAGG TGGTAGTGGA GGGGGTGGGT CAGGCGGTGG CGGCGGTTCC CTGACTGA CGCAGAGCCC GTCTAGTTTG AGCGCAAGCG TGGGCGATCG
      GGCCACCTCC ACCATCACCT CCCCCACCCA GTCCGCCACC GCCGCCAAGG GACTGACT GCGTCTCGGG CAGATCAAAC TCGCGTTCGC ACCCGCTAGC

+3       V   T   I   T   C   R   A   S   Q   G   V   T   S   A   L   A   W   Y   R   Q   K   P   G   S   P   P   Q   L   L   I   Y   D   A
501   TATTACAATT ACCTGTCGGG CGAGCCAAGG TGTTACCTCC GCCCTGGCCT GGTATCGTCA GAAACCCGGG AGCCCGCCAC AGTTGTTGAT CTACGATGCG
      ATAATGTTAA TGGACAGCCC GCTCGGTTCC ACAATGGAGG CGGGACCGGA CCATAGCAGT CTTTGGGCCC TCGGGCGGTG TCAACAACTA GATGCTACGC

+3       S   S   L   E   S   G   V   P   S   R   F   S   G   S   G   S   G   T   E   F   T   L   T   I   S   T   L   R   P   E   D   F   A
601   TCCTCACTGG AATCAGGGGT CCCTAGCCGC TTTTCCGGGT CCGGCAGCGG CACGGAATTT ACATTGACCA TAAGCACCCT GCGTCCGGAA GATTTGCCA
      AGGAGTGACC TTAGTCCCCA GGGATCGGCG AAAAGGCCCA GGCCGTCGCC GTGCCTTAAA TGTAACTGGT ATTCGTGGGA CGCAGGCCTT CTAAACGGT

+3       T   Y   Y   C   Q   Q   L   H   F   Y   P   H   T   F   G   G   G   T   V   A   A   A   A
701   CCTATTATTG CCAACAGCTG CACTTTTATC CCCATACCTT CGGTGGGGGG ACGGGGTTG ACGCGGTCG TACCGTAGCT GCTGCGGCCG C
      GGATAATAAC GGTTGTCGAC GTGAAATAG GGGTATGGAA GCCACCCCCC TGCCCCAAC TGCACGCAGC ATGGCATCGA CGACGCCGGC G
```

Figure 8

METHOD FOR ENGINEERING IMMUNOGLOBULINS

CROSS-REFERENCE TO RELATED APPLICATIONS

This application is the U.S. national stage of International Application No. PCT/AT2007/000343, filed Jul. 5, 2007 and entitled "METHOD FOR ENGINEERING IMMUNOGLOBULINS," which claims the benefit of priority from Austrian Patent Application No. A 1145/2006, filed Jul. 5, 2006 and also entitled "METHOD FOR ENGINEERING IMMUNOGLOBULINS."

The entire content of a Sequence Listing titled "F10640_Sequence_Listing_ST25.txt," created on Sep. 18, 2009 and having a size of 82 kilobytes, which has been submitted in electronic form in connection with the present application, is hereby incorporated by reference herein in its entirety.

FIELD OF INVENTION

The present invention relates to a method for engineering and manufacturing of a molecule comprising a modified immunoglobulin variable domain polypeptide.

The general field is the engineering of proteins with the aim to impart them with specific binding properties. More specifically, the engineered proteins of relevance here are immunoglobulins (antibodies), and even more specifically, single variable domains or pairs or combinations of single variable domains of immunoglobulins or combinations with other immunoglobulin domains. The specific binding properties of immunoglobulins are important features since they control the interaction with other molecules such as antigens, and render immunoglobulins useful for diagnostic and therapeutic applications.

BACKGROUND

Structure of Antibodies

The basic structure of antibodies is similar for various classes of antibodies and for various species and will be explained here using as example an intact IgG1 immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch. Disulfide bonds in the hinge region connect the two heavy chains. The light chains are coupled to the heavy chains by additional disulfide bonds.

The variable regions of both the heavy and light chains (VH) and (VL) lie at the "tips" of the Y, where they are positioned to react with antigen. This tip of the molecule is the side on which the N-termini of the amino acid sequences are located.

The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Immunoglobulin Variable Domains (V Domains)

Each domain in an antibody molecule has a similar structure of two beta sheets packed tightly against each other in a compressed antiparallel beta barrel. This conserved structure is termed the immunoglobulin fold. For reference see Bork et al. (1994) J. Mol. Biol. 242:309-320; Halaby et al. (1999) Protein Engineering 12: 563-571; Immunobiology. 5th ed. Janeway, Charles A.; Travers, Paul; Walport, Mark; Shlomchik, Mark. New York and London: Garland Publishing; 2001.

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B—C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B—C, C'-C", and F-G of the light chain variable domain and strands B—C, C'-C", and F-G of the heavy chain variable domain.

Scaffolds for Protein Engineering

Using the 3D structure of a protein as an aid for design, amino acid residues located on the surface of many proteins have been randomized using the core structure of the protein as scaffold. Examples for this strategy are described or reviewed in the following references and incorporated herein by reference: Nygren P A, Uhlen M., Curr Opin Struct Biol. (1997) 7:463-9; Binz H K, Amstutz P, Kohl A, Stumpp M T, Briand C, Forrer P, Grutter M G, Pluckthun A. Nat. Biotechnol. (2004) 22:575-82; Vogt M, Skerra A. Chembiochem. (2004) 5:191-9; U.S. Pat. No. 6,562,617; Hufton et al. FEBS Letters (2000) 475: 225; Binz et al. Nat. Biotechnol. (2005) 23:1257-68; Hosse et al. Protein Sci. (2006)15:14-27.

The basic principle of this technique is based on the observation that many proteins have a stable core, formed by specific arrangements of secondary structure elements such as beta sheets or alpha helices, which are interconnected by structures such as loops, turns, or random coils. Typically, these latter three structure elements are less crucial for the overall structure of the protein, and amino acid residues in these structure elements can be exchanged often without destroying the general fold of the protein. Naturally occurring examples for this design principle are the CDRs of immunoglobulin-like domains as can be found in antibodies, T-cell receptors and other molecules of the immunoglobulin superfamily. Artificial examples include lipocalins, ankyrins, kunitz domain inhibitor, knottin and other protein scaffolds.

Manipulation of the CDR-Loops of Immunoglobulin Variable Domains

A multitude of prior art documents show that the immunoglobulin like scaffold has been employed for the purpose of manipulating the existing antigen- or ligand-binding site, thereby introducing novel binding properties. More precisely, mainly the CDR regions have been engineered for antigen binding, in other words, in the case of the immunoglobulin fold, the natural antigen binding site has been modified in order to change its binding affinity or specificity. A vast body of literature exist which describes different formats of such manipulated immunoglobulins, frequently expressed in the form of complete antibodies, fusion products and/or fragments such as single-chain Fv fragments (scFv), diabodies, minibodies, single domains or Fab fragments and the like, either displayed on the surface of phage particles or other viruses and cells or solubly expressed in various prokaryotic or eukaryotic expression systems. The techniques are reviewed e.g. in Holliger & Hudson, Nat. Biotechnol. (2005) 23:1126-36 and Hoogenboom, Nat. Biotechnol. (2005)23: 1105-16.

Framework or Non-CDR-Regions of Immunoglobulin Variable Domains

The CDR-loops of an immunoglobulin variable domain define the antigen specificity. The rest of the molecule is termed framework (FR). These framework regions however are composed of beta-strand and loop structures.

The loops which are not CDR-loops in a native immunoglobulin variable domain do not have antigen-binding or epitope-binding specificity but contribute to the correct overall folding of the immunoglobulin domain and consequently also to the correct positioning of the CDRs and to interaction between domains. These loops are named structural loops for the purpose of this invention.

Antibody variable domains in general have been manipulated for very many different reasons, such as the construction of various antibody formats, CDR grafting (i.e. grafting of specificity of a particular antibody into another framework; e.g. Jones et al. Nature (1986) 321: 522-525; Kashmiri et al. Methods (2005) 36:25-34), changing the surface of variable domains in order to make it more soluble and stable (e.g. Ewert et al. Methods (2004) 34:184-99; Conrath et al. J Mol Biol. (2005) 350:112-125), to render it monomeric (e.g. Dottorini et al. Biochemistry (2004) 43:622-628)) or to study the interaction between variable domains (e.g. Masuda et al. FEBS J. (2006) 273:2184-94). Many of those manipulations have involved changes in the framework region of the molecule; some amino acid mutations within structural loops of the variable domain have been performed.

The influence of remote framework regions on CDR-loop positioning is evident from CDR grafting results which show that mutation of framework amino acids frequently is necessary to regain antigen binding after grafting of CDRs from one framework to another (e.g. Foote & Winter (1992) J. Mol. Biol. 224: 487-499; Kettleborough et al. Protein Eng. (1991) 4:773-783; Wu et al. J. Mol. Biol. (1999) 294:151-162).

Simon & Rajwesky (Protein Sci. (1992) 5:229-234) have studied the effects of a four residue insertion into the FR3 loop of the heavy chain variable region from the anti-NP antibody B1-8. The insertion mutant was obtained as secreted antibody without major defects in biosynthesis, indicating that antibody variable domains can accommodate length variation not only in complementarity determining regions (CDRs), but also in framework region (FR) loops. In this case the original antigen binding site formed by the CDR-loops was not affected by the modification in a neighbouring structural loop.

Grafting of CDR-Loops into Structural Loop Regions

EP0640130B1 describes chimeric immunoglobulin superfamily protein analogues (chi-proteins) having more than one biological binding site (single V domains or Fvs). The binding sites on these proteins are comprised of hypervariable regions derived from molecules related to the immunoglobulin superfamily of molecules, including immunoglobulins, cell surface antigens (such as T-cell antigens) and cell receptors (such as Fc-receptor). The hypervariable regions are called "CDR-like regions" and define ligand binding sites. Additionally, the chi-protein has at least one more ligand binding site segment, also a CDR-like region, spliced into the FR-like regions of the beta-barrel domain.

Each ligand binding site of the chi-protein therefore is comprised of a CDR-like region derived from molecules of the immunoglobulin superfamily. For example, a ligand binding site is comprised of the CDRs derived from an immunoglobulin molecule whose ligand is an antigen.

EP0640130B1 thus teaches how to splice CDR-like regions with a given specificity from a molecule of the immunoglobulin superfamily into the structural loops of a variable domain. It is postulated that functional bispecific antibodies can be prepared by this technique. There is a requirement for this technique that the relative orientations of the CDR-like loops (CDR loop symmetry) for a variable domain be reproduced to a reasonable approximation in the relative orientation of the structural loops. EP0640130B1 claims that such an approximation of the CDR-like loop symmetry does exist for the structural loops. However, it is doubtful that the relative orientation of the CDR-loops and the structural loops is similar in sufficient detail and resolution; consequently it has not been described to date that it is actually possible to develop bispecific molecules by this technique.

EP0640130B1 exemplifies that R19.9 (a monoclonal murine antibody specific for the p-azobenzenearsonate) and 26-10 (monoclonal murine antibody specific for ouabain) were used as the framework providing the primary CDR loops respectively, and the CDR-loops of murine anti-lysozyme antibody D1.3 were grafted into the structural loop regions. However, functional specificity after grafting is not described.

Another example describes that the single chain antibody 26-10 specific for ouabain could retain its ouabain-specificity after grafting two CDRs from the lysozyme-specific antibody into the structural loops of the ouabain-specific single-chain Fv antibody fragment. However, it is not described that the antibody fragment which was made according to this method had also lysozyme-binding specificity.

Grafting of Peptides into the Structural Loop Region

WO00244215A2 describes binding molecules comprising a specific target binding site and an Fc effector peptide. The Fc effector peptide is a peptide of up to 100 amino acids which interacts with effector molecules. The effector peptide may, e.g. be inserted into the loop regions of an antibody provided that the ability to bind an antigen is not adversely affected. The insertion of an effector peptide into a non-CDR loop of a CH1-domain of an immunoglobulin fragment is exemplified. The same insertion is not described for a variable domain. Every peptide grafted into a non-CDR loop according to this disclosure has a high chance of being inactive due to the different structural environment in which it has been placed. In addition, it may be difficult to retain a specific CDR-loop conformation in a parent immunoglobulin if a peptide is grafted into a structural loop of a variable domain. Consequently, it is not described that an effector peptide can be grafted into a variable domain without loss of either antigen binding or effector molecule binding.

PCT/EP2006/050059 describes a method of engineering an immunoglobulin which comprises a modification in a structural loop region to obtain a new antigen binding sites. This method is broadly applicable to immunoglobulins and may be used to produce a series of immunoglobulins targeting a variety of antigens.

US2005/266000A1 describes polypeptides comprising a variant heavy chain variable framework domain (VFR). A VFR is part of the antigen binding pocket or groove that may contact antigen. VFRs are part of the CDR loop region, herein also called CDR region, and located at a variable domain at the side of the CDR loops to support the antigen binding via the CDR loop region. Framework loops other than VFR have not been mutated for the purpose of engineering an antigen binding site.

It is an object of the present invention to provide immunoglobulins and variable immunoglobulin domains with improved antigen binding properties and methods for engineering and manufacturing immunoglobulins with the improved variable domains.

DESCRIPTION OF THE INVENTION

The object is met by the subject matter of the present invention.

The present invention relates to a method for engineering an immunoglobulin comprising a variable domain and at least one modification in at least two structural loops of said immunoglobulin and determining the binding of said immunoglobulin to an epitope of an antigen, wherein the unmodified immunoglobulin does not significantly bind to said epitope, comprising the steps of:

- providing a nucleic acid encoding an immunoglobulin comprising at least two structural loops,
- modifying at least one nucleotide residue of each of said structural loops,
- transferring said modified nucleic acid in an expression system,
- expressing said modified immunoglobulin,
- contacting the expressed modified immunoglobulin with an epitope, and
- determining whether said modified immunoglobulin binds to said epitope.

The structural loops engineered according to the invention are preferably located within one or two structural loop regions, in some cases the modifications are placed in even more than 2 structural loop regions.

In order to overcome the shortcomings of the state of the art as described in WO00244215A2 and EP0640130B1 in engineering a binding site into a structural loop region of an antibody variable domain, the present invention provides methods to select specific binding of a polypeptide (i.e. a variable domain peptide comprising modified structural loop regions) in its natural context (i.e. antibody variable domain). In order to increase the number of potential structures of variant immunoglobulin domains which can be selected for antigen-binding at least two structural loops or loop regions are modified according to the invention. Thus it is possible to introduce and select for many different modifications with minimal disturbance of the overall domain structure. Another advantage of modifying at least two loops or loop regions is the enlarged surface area potentially able to interact with a specific binding partner. The thus modified immunoglobulin variable domains are selected for specific functions or binding. The invention enables to engineer a modified immunoglobulin variable domain and a modified immunoglobulin binding with its modified structural loops or loop regions with high affinity binding and/or high specificity to a binding partner. The method allows selection of specific binding molecules with minimal modifications and without destruction of the overall structure of the variable immunoglobulin domain.

To overcome the difficulty to retain a specific CDR-loop conformation in a parent immunoglobulin a structural loop of a variable domain is modified according to the invention. It is thus the first time possible to add to the antigen binding properties of an immunoglobulin without significant loss of antigen binding or even effector molecule binding of a parent antibody. It is surprisingly possible to engineer the immunoglobulin according to the invention without significantly interfering with the binding properties of a specific CDR-loop conformation, such as binding affinity, avidity and specificity, of the parent immunoglobulin.

A specific CDR-loop conformation provides for antigen-binding by CDR loops or a CDR loop region. Any immunoglobulin that is antigen binding through such a CDR-loop conformation may be modified according to the invention to obtain an additional binding site in a structural loop of the immunoglobulin, preferably while the specific CDR-loop conformation and the original antigen binding properties of the parent molecule may be retained or unchanged. Preferably the binding properties of the CDR-loop conformation may be maintained to the extend that the binding affinity of the parent molecule is not significantly reduced, for instance, the dissociation constant Kd is not significantly increased, meaning that the difference in Kd is a factor preferably less than $10^4$, more preferably less than $10^3$, even more preferred less than $10^2$, or less than 10.

In accordance with the present invention, one of the key features of the present invention is that the engineering of the immunoglobulin or immunoglobulin variable domains takes place in regions which are not normally-involved in antigen binding, in other words, in regions other than the CDRs of an antibody variable domain. It was observed that the specific fold of immunoglobulin domains allows the introduction of random mutations in regions which are structurally analogous to the CDRs but different in position in sequence and structure. The regions identified for modification according to the present invention are, like CDRs, loop regions connecting the beta strands of the immunoglobulin fold. These structural loops or loop regions can be mutated as described in the present invention without affecting the binding of the variable domains of the immunoglobulin that is mediated through the CDR loops. By mutating said structural loops or loop regions, a new molecular binding surface or binding pocket is generated that is similar in size and shape to the binding surface or binding pocket formed by the CDR loops of the natural antigen binding site of an antibody. Since the structural loops can also be extended by the insertion of additional amino acids, the architecture of the newly generated binding site can be voluntarily adjusted to the target to which it should bind. For example, deep binding pockets which are especially suitable for the binding of small molecules can be preferentially formed by long loops, i.e. structural loops with additional amino acids inserted in their sequence, whereas rather flat binding surfaces, which are well suited to bind to targets with a large, flat molecular surface are preferentially formed when the residues in the structural loops are mutated without the insertion of additional residues More specifically, it is described herein that by introducing random mutations in the loops connecting beta strands A-B, C'-D and E-F of a human or humanized heavy chain variable domain, mutated domains can be selected that bind specifically to either human serum albumin or to Fcgamma receptor III, which are not normally recognized and bound by human or humanized immunoglobulin variable domains. The mutations introduced include mutations in which selected amino acid residues in the wild-type sequence were replaced by randomly chosen residues, and they also include insertions of extra amino acid residues in the loops mentioned above. Thus, preferably modified immunoglobulins are provided according to the invention that are obtainable and produced according to the above described methods, and have a binding site specific for an antigen, in particular specific for a serum albumin, cell receptors and complement factors, more specifically human serum albumin and Fc receptors.

In particular, the present invention relates to a method for engineering an immunoglobulin variable domain and an immunoglobulin containing such a domain that is binding specifically to an epitope of an antigen.

Specifically the method according to the invention comprises the steps of:
 providing a nucleic acid encoding an immunoglobulin binding specifically to at least one first epitope and is comprising at least two structural loops or loop regions,
 modifying at least one nucleotide residue of each of said structural loops or loop regions encoded by said nucleic acid,
 transferring said modified nucleic acid in an expression system,
 expressing said modified immunoglobulin,
 contacting the expressed modified immunoglobulin variable domain with said at least one second epitope, and
 determining whether said modified immunoglobulin variable domain binds specifically to the second epitope.

This method preferably applies to immunoglobulin variable domain peptides. More preferably the method according to this embodiment of the invention relates to immunoglobulins that bind to said first epitope through their CDR-regions or specific CDR-loop conformation.

The method according to the invention refers further to at least one modification in each of at least two structural loops or loop regions of said immunoglobulin variable domain and determining the specific binding of said structural loops or loop regions to at least one antigen, wherein the immunoglobulin variable domain containing an unmodified structural loop or loop region does not specifically bind to such an antigen.

The term "immunoglobulin" as used herein is including immunoglobulins or parts, fragments or derivatives of immunoglobulins. Thus it includes an "immunoglobulin variable domain peptide" to be modified according to the present invention (as used herein the terms immunoglobulin and antibody are interchangeable) as well as immunoglobulin variable domains or parts thereof that contain a structural loop, such as a minidomain, or a structural loop of such domains. The immunoglobulins can be used as isolated peptides or as combination molecules with other peptides. In some cases it is preferable to use a defined modified structural loop or a structural loop region, or parts thereof, as isolated molecules for binding or combination purposes. The "immunoglobulin variable domain" as defined herein contains such immunoglobulin variable domain peptides or polypeptides that may have specific binding characteristics upon modifying and engineering. The peptides are homologous to immunoglobulin variable domain sequences, and are preferably at least 5 amino acids long, more preferably at least 10 or even at least 50 or 100 amino acids long, and constitute at least partially the structural loop region or the non-CDR loop region of the variable domain. Preferably the peptides exclude those insertions that are considered non-functional amino acids, hybrid or chimeric CDR-regions or CDR-like regions and/or canonical structures of CDR regions. The binding characteristics relate to specific epitope binding, affinity and avidity.

A derivative of an immunoglobulin according to the invention is any combination of one or more immunoglobulins of the invention and or a fusion protein in which any domain or minidomain of the immunoglobulin of the invention may be fused at any position of one or more other proteins (such as other immunoglobulins, ligands, scaffold proteins, enzymes, toxins and the like). A derivative of the immunoglobulin of the invention may also be obtained by recombination techniques or binding to other substances by various chemical techniques such as covalent coupling, electrostatic interaction, disulphide bonding etc.

The other substances bound to the immunoglobulins may be lipids, carbohydrates, nucleic acids, organic and anorganic molecules or any combination thereof (e.g. PEG, prodrugs or drugs). A derivative is also an immunoglobulin with the same amino acid sequence but made completely or partly from non-natural or chemically modified amino acids.

The engineered molecules according to the present invention will be useful as stand-alone proteins as well as fusion proteins or derivatives, most typically fused in such a way as to be part of larger antibody structures or complete antibody molecules, or parts thereof such as Fab fragments, Fc fragments, Fv fragments and others. It will be possible to use the engineered proteins to produce molecules which are bispecific, trispecific, and maybe even carry more specificities at the same time, and it will be possible at the same time to control and preselect the valency of binding at the same time according to the requirements of the planned use of such molecules.

Another aspect of the present invention relates to an immunoglobulin with at least one loop region besides the CDR-loop conformation of the variable domain, characterised in that said at least one loop region comprises at least one amino acid modification forming at least one modified loop region, wherein said at least one modified loop region binds specifically to at least one epitope of an antigen.

It is preferred to molecularly combine at least one modified antibody domain, which is binding to the specific partner via the non-variable sequences or a structural loop, with at least one other binding molecule, which can be an antibody, antibody fragment, a soluble receptor, a ligand or another modified antibody domain.

The molecule that functions as a part of a binding pair that is specifically recognized by the immunoglobulin according to the invention is preferably selected from the group consisting of proteinaceous molecules, nucleic acids and carbohydrates.

The modified loops or loop regions of the immunoglobulins according to the invention may specifically bind to any kind of binding molecules or structures, in particular to antigens, proteinaceous molecules, proteins, peptides, polypeptides, nucleic acids, glycans, carbohydrates, lipids, small organic molecules, anorganic molecules, or combinations or fusions thereof. Of course, the modified immunoglobulins may comprise at least two loops or loop regions whereby each of the loops or loop regions may specifically bind to different molecules or epitopes.

According to the present invention, binding regions to antigens or antigen binding sites of all kinds of cell surface antigens, may be introduced into a structural loop of a given antibody structure.

Binding of the immunoglobulins according to the invention is preferably on the one hand through CDR-regions, if the immunoglobulin contains such a CDR-region, and on the other hand through an additional binding site that is formed by modifying at least two structural loops. Those structural loops are either placed on one or at least two variable domains having one or more modified structural loops. Thus, an immunoglobulin according to the invention contains at least two modifications in the structural loops of variable domains either through at least one modification of at least two variable domains or at least two modifications of at least one variable domain. Preferably the modified immunoglobulin thus exhibits a binding site either by changing the primary structure of the protein or by changing the tertiary structure to obtain a conformation specific binding site.

By analogy the immunoglobulin variable domains from any class of immunoglobulins and from immunoglobulins from any species are amenable to this type of engineering. Furthermore not only the specific loops targeted in the examples of the present invention can be manipulated, but any loop connecting beta strands in immunoglobulin variable domains can be manipulated in the same way.

Engineered immunoglobulins or immunoglobulin variable domains from any organism and from any class of immunoglobulin can be used according to the present invention either as such (as single domains), or as part of a larger molecule. For example, they can be part of an intact immunoglobulin, which accordingly would have its "normal" antigen binding region formed by at least one of the 6 CDRs and the new, engineered antigen binding site. Like this, a multi-specific, e.g. bispecific, or trispecific immunoglobulin could be generated. The engineered immunoglobulin domains can also be part of any fusion protein.

Immunoglobulins or immunoglobulin variable domains according to the invention may be complete antibody molecules or part of antibodies, such as IgG, IgA, IgM, IgD, IgE and the like. The immunoglobulins or immunoglobulin variable domains of the invention may also contain or consist of a functional antibody fragment such as Fab, Fab2, scFv, Fv, or parts thereof, or other derivatives or combinations of the immunoglobulins such as minibodies, domains of the heavy and light chains of the variable region (such as Fd, VL, including Vlambda and Vkappa, VH, VHH) as well as mini-domains consisting of two beta-strands of an immunoglobulin domain connected by at least two structural loops (see for example Laffly et al (2005) Hum Antibodies. 2005; 14:33-55), as isolated domains or in the context of naturally associated molecules.

The modified immunoglobulin according to the invention is possibly further combined with one or more modified immunoglobulins or with unmodified immunoglobulins, or parts thereof, to obtain a combination immunoglobulin. Combinations are preferably obtained by recombination techniques, but also by association through adsorption, electrostatic interactions or the like, or else through chemical binding with or without a linker. The preferred linker sequence is either a natural linker sequence or a functionally suitable artificial sequence.

It is understood that the term "immunoglobulin", "immunoglobulin variable domain peptide" and "immunoglobulin variable domain" includes derivatives as well. A derivative is any part or combination of one or more immunoglobulins and/or a fusion protein in which any domain or minidomain of the immunoglobulin as obtained according to the invention may be combined or fused at any position with one or more other peptides or proteins (including but not limited to other immunoglobulins, immunoglobulin domains, Fc parts, ligands, scaffold proteins, enzymes, toxins, serum proteins and the like). A derivative of the immunoglobulin of the invention may also be obtained by binding the unmodified or modified immunoglobulin or immunoglobulin variable domain of the invention to other substances by various chemical techniques such as covalent coupling, electrostatic interaction, disulphide bonding etc.

The other substances bound to the immunoglobulin or immunoglobulin variable domain may be lipids, carbohydrates, nucleic acids, organic and anorganic molecules or any combination thereof (e.g. PEG, pro-drugs or drugs). A derivative is also an immunoglobulin or immunoglobulin variable domain with the same amino acid sequence but made completely or partly from non-natural, artificial or chemically modified amino acids.

The engineered molecules according to the present invention will be useful as stand-alone proteins as well as fusion proteins or derivatives, most typically fused before or after modification in such a way as to be part of larger antibody structures or complete antibody molecules, or parts thereof. Immunoglobulins according to the invention may thus also consist of or comprise Fab fragments, Fc fragments, Fv fragments, single chain antibodies, in particular single-chain Fv fragments, bi- or multispecific scFv, diabodies, multibodies, multivalent or multimers of immunoglobulin domains and others. It will be possible to use the engineered proteins to produce molecules which are monospecific, bispecific, trispecific, and molecules that may even carry more specificities. By the invention it is possible to control and preselect the valency of binding at the same time according to the requirements of the planned use of such molecules.

According to the present invention, one or more binding sites to antigens or antigen binding sites to one or more antigens may be introduced into a structural loop or loop region of a given antibody variable domain structure. The antigens may be naturally occurring molecules or chemically synthesized molecules or recombinant molecules, either in solution or in suspension, e.g. located on or in particles such as solid phases, on or in cells or on viral surfaces. It was surprising that the binding of an immunoglobulin to an antigen could be achieved according to the invention, even when the antigen is still adhered or bound to molecules and structures that would hinder its binding. By employing the target antigen in its selected or natural context and structure for selecting the modified and designed immunoglobulin, it is possible to identify and obtain those modified immunoglobulins that are best suitable for the purpose of diagnostic or therapeutic use.

The term "antigen" as used herein shall comprise molecules selected from the group consisting of allergens, tumor associated antigens, self antigens including albumin, T cell receptors, FcRn, cell surface receptors, enzymes, Fc-receptors, proteins of the complement system, serum molecules, bacterial antigens, fungal antigens, protozoan antigen and viral antigens, also molecules responsible for transmissible spongiform encephalitis (TSE), such as prions, infective or not, and markers or molecules that relate to Alzheimer disease. Antigens can be targeted and bound by the immunoglobulins or immunoglobulin variable domains as engineered according to the invention through at least part of a modified structural loop.

In a preferred embodiment the immunoglobulin is binding with its modified structural loops specifically to at least two such epitopes that are identical or differ from each other, either of the same antigen or of different antigens.

For example, the method according to the invention refers to engineering an immunoglobulin or immunoglobulin variable domain that is binding specifically to at least one first epitope and comprising at least one modification in each of at least two structural loops or loop regions of said immunoglobulin, and determining the specific binding of said loops or loop regions to at least one second epitope, the epitope being selected from the group of antigens as mentioned above, wherein the unmodified structural loop or loop region (non-CDR region) does not specifically bind to said at least one second epitope.

The term antigen as used according to the present invention shall in particular include all antigens and target molecules capable of being recognised by a binding site of an immunoglobulin or an antibody structure, as a whole target molecule or as a fragment of such molecule (especially substructures of targets, generally referred to as "epitopes").

Preferred antigens as targeted by the immunoglobulins according to the invention are those antigens or molecules, which have already been proven to be or are capable of being immunogenic, bound by immune response factors, or else immunologically or therapeutically relevant, especially those, for which a clinical efficacy has been tested.

The term "antigen" according to the present invention shall mean molecules or structures known to interact or capable of interacting with the CDR-loop region of immunoglobulins. Structural loop regions of the prior art referring to native antibodies, do not interact with antigens but rather contribute to the overall structure and/or to the binding to effector molecules. Only upon engineering according to the invention structural loops may form antigen binding pockets without involvement of CDR loops or the CDR region.

According to a preferred embodiment the antigen bound by the immunoglobulin according to the invention is a cell surface antigen. The term "cell surface antigens" shall include all antigens or capable of being recognised by an antibody structure on the surface of a cell, and fragments of such molecules. Preferred "cell surface antigens" are those antigens, which have already been proven to be or which are capable of being immunologically or therapeutically relevant, especially those, for which a preclinical or clinical efficacy has been tested. Those cell surface molecules are specifically relevant for the purpose of the present invention, which mediate cell killing activity. Upon binding of the immunoglobulin according to the invention to at least two of those cell surface molecules the immune system provides for cytolysis or cell death, thus a potent means for attacking human cells may be provided.

Preferably the antigen is selected from cell surface antigens, including receptors, in particular from the group consisting of erbB receptor tyrosine kinases (such as EGFR, HER2, HER3 and HER4, but not limited to these), molecules of the TNF-receptor superfamily, such as Apo-1 receptor, TNFR1, TNFR2, nerve growth factor receptor NGFR, CD40, T-cell surface molecules, T-cell receptors, T-cell antigen OX40, TACI-receptor, BCMA, Apo-3, DR4, DR5, DR6, decoy receptors, such as DcR1, DcR2, CAR1, HVEM, GITR, ZTNFR-5, NTR-1, TNFL1 but not limited to these molecules, B-cell surface antigens, such as CD10, CD19, CD20, CD21, CD22, antigens or markers of solid tumors or hematologic cancer cells, cells of lymphoma or leukaemia, other blood cells including blood platelets, but not limited to these molecules.

According to a further preferred embodiment of the present invention the antigen or the molecule binding to the modified structural loop or loop region is selected from the group consisting of tumor associated antigens, in particular EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, allergy related molecules IgE, cKIT and Fc-epsilon-receptorI, IRp60, IL-5 receptor, CCR3, red blood cell receptor (CR1), human serum albumin, mouse serum albumin, rat serum albumin, neonatal Fc-gamma-receptor FcRn, Fc-gamma-receptors Fc-gamma RI, Fc-gamma-RII, Fc-gamma RIII, Fc-alpha-receptors, Fc-epsilon-receptors, fluorescein, lysozyme, toll-like receptor 9, erythropoietin, CD2, CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD64, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNFbeta2, TNFalpha, TNFalphabeta, TNF-R1, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF—R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLA-DR, CTLA-4, T cell receptor, B7-1, B7-2, VNRintegrin, TGFbeta1, TGFbeta2, eotaxin1, BLyS (B-lymphocyte Stimulator), complement C5, IgE, IgA, IgD, IgM, IgG, factor VII, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrates such as blood group antigens and related carbohydrates, Galili-Glycosylation, Gastrin, Gastrin receptors, tumor associated carbohydrates, Hapten NP-cap or NIP-cap, T cell receptor alpha/beta, E-selectin, P-glycoprotein, MRP3, MRP5, glutathione-S-transferase pi (multi drug resistance proteins), alpha-granule membrane protein(GMP) 140, digoxin, placental alkaline phosphatase (PLAP) and testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNRintegrin, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof.

Preferably, the antigen is selected from the group consisting of pathogen antigen, tumor associated antigen, enzyme, substrate, self antigen, organic molecule or allergen. More preferred antigens are selected from the group consisting of viral antigens, bacterial antigens or antigens from pathogens of eukaryots or phages. Preferred viral antigens include HAV-, HBV-, HCV-, HIV I-, HIV II-, Parvovirus-, Influenza-, HSV-, Hepatitis Viruses, Flaviviruses, Westnile Virus, Ebola Virus, Pox-Virus, Smallpox Virus, Measles Virus, Herpes Virus, Adenovirus, Papilloma Virus, Polyoma Virus, Parvovirus, Rhinovirus, Coxsackie virus, Polio Virus, Echovirus, Japanese Encephalitis virus, Dengue Virus, Tick Borne Encephalitis Virus, Yellow Fever Virus, Coronavirus, respiratory syncytial virus, parainfluenza virus, La Crosse Virus, Lassa Virus, Rabies Viruse, Rotavirus antigens; preferred bacterial antigens include *Pseudomonas-, Mycobacterium-, Staphylococcus-, Salmonella-, Meningococcal-, Borellia-, Listeria, Neisseria-, Clostridium-, Escherichia-, Legionella-, Bacillus-, Lactobacillus-, Streptococcus-, Enterococcus-, Corynebacterium-, Nocardia-, Rhodococcus-, Moraxella-, Brucella, Campylobacter-, Cardiobacterium-, Francisella-,*

*Helicobacter-, Haemophilus-, Klebsiella-, Shigella-, Yersinia-, Vibrio-, Chlamydia-, Leptospira-, Rickettsia-, Mycobacterium-, Treponema-, Bartonella*-antigens. Preferred eukaryotic antigens of pathogenic eukaryotes include antigens from *Giardia, Toxoplasma, Cyclospora, Cryptosporidium, Trichinella, Yeasts, Candida, Aspergillus, Cryptococcus, Blastomyces, Histoplasma, Coccidioides.*

The modified immunoglobulin according to the present invention may preferably bind to one of the molecules disclosed above. These molecules comprise also allergens and haptens.

Substructures of antigens are generally referred to as "epitopes" (e.g. B-cell epitopes, T-cell epitopes), as long as they are immunologically relevant, i.e. are also recognisable by natural or monoclonal antibodies. The term "epitope" according to the present invention shall mean a molecular structure which may completely make up a specific binding partner or be part of a specific binding partner to the binding domain or the immunoglobulin of the present invention.

Chemically, an epitope may either be composed of a carbohydrate, a peptide, a fatty acid, an anorganic substance or derivatives thereof and any combinations thereof. If an epitope is a peptide or polypeptide, there will usually be at least 3 amino acids, preferably 8 to 50 amino acids, and more preferably between about 10-20 amino acids included in the peptide. There is no critical upper limit to the length of the peptide, which could comprise nearly the full length of the polypeptide sequence. Epitopes can either be linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence.

Specifically, epitopes are at least part of diagnostically relevant molecules, i.e. the absence or presence of an epitope in a sample is qualitatively or quantitatively correlated to either a disease or to the health status or to a process status in manufacturing or to environmental and food status. Epitopes may also be at least part of therapeutically relevant molecules, i.e. molecules which can be targeted by the specific binding domain which changes the course of the disease.

Besides the antigen binding sites of the immunoglobulin as engineered according to the invention further binding capacities may be introduced aside from or into the structural loop regions of variable domains, e.g. binding capacities for other antigens, small molecules, for drugs or enzymes, catalytic sites of enzymes or enzyme substrates or the binding to a transition state analogue of an enzyme substrate.

Preferably the new antigen binding site in the structural loops is foreign to the unmodified immunoglobulin variable domain. Thus foreign targets like effector molecules, serum proteins or Fc-receptors or cell surface receptors, which are not bound by variable domains by nature, are preferred as antigens or binding molecules bound by the immunoglobulin variable domains according to the invention.

In this contact the term "foreign" means that the antigen is not recognized by the specific CDR binding region or other natural or intrinsic binding regions of the immunoglobulin. A foreign binding partner, but not the natural binding partner of an immunoglobulin, may thus be bound by the newly formed antigen binding site of a structural loop. This means that a natural binding partner, such as an Fc-receptor or an effector of the immune system, is not considered to be bound by the antigen binding site foreign to the unmodified immunoglobulin.

As used herein, the term "specifically binds" or "specific binding" refers to a binding reaction which is determinative of the cognate ligand of interest in a heterogeneous population of molecules. Thus, under designated conditions (e.g. immunoassay conditions), the specified antibody variable domain binds to its particular "target" and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may then also be integrated into the host chromosome. Alternatively, an expression system can be used for in vitro transcription/translation.

A "structural loop" or "non-CDR-loop" according to the present invention is to be understood in the following manner: immunoglobulins are made of domains with a so called immunoglobulin fold. In essence, anti-parallel beta sheets are connected by loops to form a compressed antiparallel beta barrel. In the variable region, some of the loops of the domains contribute essentially to the specificity of the antibody, i.e. the binding to an antigen. These loops are called CDR-loops.

The CDR loops are located within the CDR loop region, which may in some cases also the variable framework region (called "VFR") adjacent to the CDR loops. It is known that VFRs may contribute to the antigen binding pocket of an antibody, which generally is mainly determined by the CDR loops. Thus, those VFRs are considered as part of the CDR loop region, and would not be appropriately used for the purpose of the invention. Contrary to those VFRs within the CDR loop region or located proximal to the CDR loops, other VFRs of variable domains would be particularly suitable to be used according to the invention. Those are the structural loops of the VFRs located opposite to the CDR loop region, or at the C-terminal side of a variable immunoglobulin domain.

All loops of antibody variable domains outside the CDR loop region are rather contributing to the structure of the molecule. These loops are defined herein as structural loops or non-CDR-loops.

All numbering of the amino acid sequences of the immunoglobulins is according to the IMGT numbering scheme (IMGT, the international ImMunoGeneTics information system; Lefranc et al., 1999, Nucleic Acids Res. 27:209-212; Ruiz et al., 2000 Nucleic Acids Res. 28:219-221; Lefranc et al., 2001, Nucleic Acids Res. 29:207-209; Lefranc et al., 2003, Nucleic Acids Res. 31:307-310; Lefranc et al., 2005, Dev Comp Immunol 29:185-203).

According to a preferred embodiment of the present invention the immunoglobulin variable domain is of human, camelid, rabbit, chicken, rat, dog, horse, sheep or murine origin.

Since the modified immunoglobulin may be employed for various purposes, in particular in pharmaceutical compositions, the immunoglobulin is preferably of human, camelid or murine origin. Of course, the modified immunoglobulin may also be a humanized or a chimeric immunoglobulin. In the most preferred embodiment of the invention the modified variable domain is of human origin or a humanized version of a variable domain of any species.

A humanized immunoglobulin variable domain has at least about 50% amino acid sequence identity, preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity, more preferably at least about 95% amino acid sequence identity to a native human immunoglobulin variable domain sequence.

A humanized immunoglobulin variable domain has furthermore at least about 50% amino acid sequence identity, preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity, more preferably at least about 95% amino acid sequence identity when comparing all surface accessible amino acids to the surface accessible amino acids of a native human immunoglobulin variable domain sequence.

The preferred homology or sequence identities specifically relates to those sequences of the framework region.

The preferred immunoglobulin according to the invention comprises a domain that has at least 50% homology with the unmodified domain.

The term "homology" indicates that polypeptides have the same or conserved residues at a corresponding position in their primary, secondary or tertiary structure. The term also extends to two or more nucleotide sequences encoding the homologous polypeptides.

"Homologous immunoglobulin domain" means an immunoglobulin domain according to the invention having at least about 50% amino acid sequence identity with regard to a full-length native sequence immunoglobulin domain sequence or any other fragment of a full-length immunoglobulin domain sequence as disclosed herein. Preferably, a homologous immunoglobulin domain will have at least about 50% amino acid sequence identity, preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity, more preferably at least about 95% amino acid sequence identity to a native immunoglobulin domain sequence, or any other specifically defined fragment of a full-length immunoglobulin domain sequence as disclosed herein.

"Percent (%) amino acid sequence identity" with respect to the immunoglobulin domain sequences identified herein is defined as the percentage of amino acid residues in a candidate sequence that are identical with the amino acid residues in the specific immunoglobulin variable domain sequence, after aligning the sequence and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

% amino acid sequence identity values may be obtained as described below by using the WU-BLAST-2 computer program (Altschul et al., Methods in Enzymology 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the immunoglobulin variable domain of interest having a sequence derived from the native immunoglobulin variable domain and the comparison amino acid sequence of interest (i.e., the sequence against which the immunoglobulin variable domain of interest is being compared which may be the unmodified immunoglobulin variable domain) as determined by WU-BLAST-2 by (b) the total number of amino acid residues of the non-randomized parts of the immunoglobulin variable domain of interest. For example, in the statement "a polypeptide comprising an amino acid sequence X which has or having at least 80% amino acid sequence identity to the amino acid sequence Y", the amino acid sequence A is the comparison amino acid sequence of interest and the amino acid sequence B is the amino acid sequence of the immunoglobulin variable domain of interest.

In a preferred embodiment the polypeptide according to the invention is a bispecific antibody or a bispecific single chain antibody or a bispecific Fab or a bispecific sdAb. Further preferred is that the polypeptide comprises a bispecific domain or a part thereof. Specific examples refer to Fab or dAb molecules with additional functionality through the new binding site at the opposite side of the CDR region. The preferred immunoglobulin according to the invention, which is a Fab molecule, may, for example, contain one or two additional binding sites at the C-terminal loop side of a CH1 and/or a CL domain. The preferred immunoglobulin according to the invention, which is a dAb molecule, may, for example, contain an additional binding site at the C-terminal loop side of a Vh, Vhh or Vl domain. By such additional binding sites additional functionalities, like prolonged half life (e.g. through binding to an FcRn or serum proteins, such as albumin or IgG), or effector function (e.g. through binding to T cell receptors, C1q or CD64) can be added to the molecules. According to such examples the dedicated Fab or dAb libraries, would be prepared with an appropriate size to enable selection of the specific binders to the specific binding partners.

The preferred variable domain according to the invention is selected from the group of VH, VL, including Vkappa and Vlambda, VHH and combinations thereof. It turned out that those modifications are of specific advantage when brought into the loops or loop regions of a VH, a Vkappa, a Vlambda or a VHH, and the modified loops or loop regions comprise at least one modification within amino acids 7 to 21, amino acids 25 to 39, amino acids 41 to 81, amino acids 83 to 85, amino acids 89 to 103 or amino acids 106 to 117.

The structural loops or loop regions of the immunoglobulin or variable domain of the immunoglobulin of human or humanized origin as modified according to the invention are selected preferably from the structural loops that comprise amino acids 8 to 20, amino acids 44 to 50, amino acids 67 to 76 and amino acids 89 to 101, most preferably amino acid positions 12 to 17, amino acid positions 45 to 50, amino acid positions 69 to 75 and amino acid positions 93 to 98.

In another preferred embodiment a modification in the structural loops or loop regions comprising amino acids 93 to 98 is combined with a modification in the structural loops or loop regions comprising amino acids 8 to 20.

The above identified amino acid regions of the respective immunoglobulins are loops or loop regions specified to be suitable for modification purposes according to the invention. Preferably combinations of such modifications, e.g. in at least two of the specified loops or loop regions, are engineered into the immunoglobulin according to the invention.

Preferably, a modification in the structural loop or loop region comprising amino acids 93 to 98 is combined with a modification in one or more of the other structural loops.

In a preferred embodiment a modification in the structural loop or loop region comprising amino acids 93 to 98 is combined with a modification in the structural loop region comprising amino acids 69 to 75.

Most preferably each of the structural loops comprising amino acids 93 to 98, amino acids 69 to 75 and amino acids 8 to 20 contain at least one amino acid modification.

In another preferred embodiment each of the structural loops comprising amino acids 93 to 98, amino acids 69 to 75, amino acids 44 to 50 and amino acids 8 to 20 contain at least one amino acid modification.

According to a preferred embodiment of the present invention the structural loops or loop regions of an immunoglobulin or the variable domain of the immunoglobulin of murine origin, e.g. a VH, comprise amino acids 6 to 20, amino acids 44 to 52, amino acids 67 to 76 and amino acids 92 to 101.

According to another preferred embodiment of the present invention the structural loops or loop regions of an immunoglobulins or the variable domain of the immunoglobulin of camelid origin, e.g. VHH, comprise amino acids 7 to 18, amino acids 43 to 55, amino acids 68 to 75 and amino acids 91 to 101.

The variable domains of camelid origin or humanized variants of camelid origin, have the advantage that they could easily be combined with other variable domains, for instance with other VHH of camelid origin, modified or native. The possible combination of VHH of camelid origin is the basis for multivalent immunoglobulins. Thus, according to the invention specific modified variable domains of camelid origin are multivalent combinations, preferably with at least 3, more preferably with at least 4 or 5 valencies or VHHs.

Preferably, the new antigen binding sites in the structural loops are introduced into the immunoglobulin encoded by the selected nucleic acid by substitution, deletion and/or insertion of at least one nucleotide.

According to another preferred embodiment of the present invention the modification of at least one nucleotide in each of at least two structural loops or loop regions result in a substitution, deletion and/or insertion in the immunoglobulin or immunoglobulin variable domain encoded by said nucleic acid.

The modification of the at least two loops or loop regions of an immunoglobulin or antibody variable domain may result in a substitution, deletion and/or insertion of 2 or more amino acids, preferably point mutations, change of amino acids of whole loops, more preferred the change of at least 2, 3, 4, 5, 6, 7, 8, 9, 10, 11, 12, 13, 14, up to 30 amino acids. However, the maximum number of amino acids inserted into a structural loops or loop regions of an immunoglobulin or immunoglobulin variable domain may in specific cases not exceed the number of 30, preferably 25, more preferably 20, amino acids.

Thereby the modified sequence comprises amino acids not included in the conserved regions of the structural loops, the newly introduced amino acids being naturally occurring, but foreign to the site of modification, or substitutes of naturally occurring amino acids. When the foreign amino acid is selected from a specific group of amino acids, such as amino acids with specific polarity, or hydrophobicity, a library enriched in the specific group of amino acids at the randomized positions can be obtained according to the invention. Such libraries are also called "focused" libraries.

The at least two loops or loop regions are preferably mutated or modified by random, semi-random or, in particular, by site-directed random mutagenesis methods.

A preferred method to introduce modifications is site directed random mutation. With this method two or more specific amino acid residues of the loops are exchanged or introduced using randomly generated inserts into such structural loops. Alternatively preferred is the use of combinatorial approaches.

In another preferred embodiment at least three structural loops or loop regions of an immunoglobulin or immunoglobulin variable domain are mutated or modified by random, semi-random or, in particular, by site-directed random mutagenesis methods.

These methods may be used to make amino acid modifications at desired positions of the immunoglobulins or immunoglobulin variable domain of the present invention. In these cases positions are chosen randomly, or amino acid changes are made using certain rules. For example certain residues may be mutated to any amino acids, whereas other residues may be mutated to a restricted set of amino acids. This can be achieved in a stepwise fashion by alternating of cycles of mutation and selection or simultaneously.

The randomly modified nucleic acid molecule may comprise the herein identified repeating units, which code for all known naturally occurring amino acids or a subset thereof. Those libraries that contain modified sequences wherein a specific subset of amino acids are used for modification purposes are called "focused" libraries. The member of such libraries have an increased probability of an amino acid of such a subset at the modified position, which is at least two times higher than usual, preferably at least 3 times or even at least 4 times higher. Such libraries have also a limited or lower number of library members, so that the number of actual library members reaches the number of theoretical library members. In some cases the number of library members of a focused library is not less than $10^3$ times the theoretical number, preferably not less than $10^2$ times, most preferably not less than 10 times.

A library according to the invention may be designed as a library containing or consisting of library members of a specific immunoglobulin format. Those libraries that are consisting of specific immunoglobulin molecular format are called dedicated library for the purpose of this invention. Dedicated libraries preferably contain a majority of the specific formats, at least 50%, preferably at least 60%, more preferred at least 70%, more preferred at least 80%, more preferred at least 90%, or those that essentially consist of specific antibody formats. Specific antibody formats are preferred, such that the preferred library according to the invention it is selected from the group consisting of a VH library, VHH library, Vkappa library, Vlambda library, Fab library, a CH1/CL library and a CH3 library. Libraries characterized by the content of composite molecules containing more than one antibody domains, such as an IgG library or Fc library are specially preferred. Other preferred libraries are those/containing T-cell receptors, forming T-cell receptor libraries. Further preferred libraries are epitope libraries, wherein the fusion protein comprises a molecule with a variant of an epitope, also enabling the selection of competitive molecules having similar binding function, but different functionality. Exemplary is a TNFalpha library, wherein trimers of the TNFalpha fusion protein are displayed by a single genetic package.

However, the maximum number of amino acids inserted into a loop or loop region of an immunoglobulin preferably may not exceed the number of 30, preferably 25, more preferably 20 amino acids at a maximum. The substitution and the insertion of the amino acids occurs preferably randomly or semi-randomly using all possible amino acids or a selection of preferred amino acids for randomization purposes, by methods known in the art and as disclosed in the present patent application.

The site of modification may be at a specific single structural loop or a structural loop region. A loop region usually is composed of at least two, preferably at least 3 or at least 4 loops that are adjacent to each other, and which may contribute to the binding of an antigen through forming an antigen binding site or antigen binding pocket. It is preferred that the one or more sites of modification are located within the area of 10 amino acids, more preferably within 20, 30, 40, 50, 60, 70, 80, 90 up to 100 amino acids, in particular within a structural loop region to form a surface or pocket where the antigen can sterically access the loop regions.

The at least one loop or loop region is preferably mutated or modified to produce libraries, preferably by random, semi-random or, in particular, by site-directed random mutagenesis methods, in particular to delete, exchange or introduce randomly generated inserts into structural loops. Alternatively preferred is the use of combinatorial approaches. Any of the known mutagenesis methods may be employed, among them cassette mutagenesis. These methods may be used to make amino acid modifications at desired positions of the immunoglobulin of the present invention. In some cases positions are chosen randomly, e.g. with either any of the possible amino acids or a selection of preferred amino acids to randomize loop sequences, or amino acid changes are made using simplistic rules. For example all residues may be mutated preferably to specific amino acids, such as alanine, referred to as amino acid or alanine scanning. Such methods may be coupled with more sophisticated engineering approaches that employ selection methods to screen higher levels of sequence diversity.

A preferred method according to the invention refers to a randomly modified nucleic acid molecule coding for an immunoglobulin, immunoglobulin domain or a part thereof which comprises at least one nucleotide repeating unit within a structural loop coding region having the sequence 5'-NNS-3', 5'-NNN-3',5'-NNB-3' or 5'-NNK-3'. In some embodiments the modified nucleic acid comprises nucleotide codons selected from the group of TMT, WMT, BMT, RMC, RMG, MRT, SRC, KMT, RST, YMT, MKC, RSA, RRC, NNK, NNS, NNN or any combination thereof (the coding is according to IUPAC).

The randomly modified nucleic acid molecule may comprise the above identified repeating units, which code for all known naturally occurring amino acids or a subset thereof.

The modification of the nucleic acid molecule may be performed by introducing synthetic oligonucleotides into a larger segment of nucleic acid or by de novo synthesis of a complete nucleic acid molecule. Synthesis of nucleic acid may be performed with tri-nucleotide building blocks which would reduce the number of nonsense sequence combinations if a subset of amino acids is to be encoded (e.g. Yanez et al. Nucleic Acids Res. (2004) 32:e158; Virnekas et al. Nucleic Acids Res. (1994) 22:5600-5607).

Preferably the positions to be modified are surface exposed amino acids. Surface exposition of amino acids of structural loops can be judged from known protein structures of antibody variable domains and by analogy or homology for such amino acid sequences for which no experimentally determined structure is available.

In a preferred embodiment of the invention the modifications introduced into the at least two structural loops comprise at least 1, 2, 3, 4, 5 or 6 foreign amino acids or amino acids not naturally occurring at the respective site of the structural loop of the non-modified immunoglobulin or immunoglobulin variable domain.

The modification of amino acids may preferentially be biased in order to introduce into structural loops or loop regions amino acids which are known to be frequently involved in protein-protein interactions (e.g. Lea & Stewart (1995) FASEB J. 9:87-93; Fellhouse et al. (2006) J. Mol. Biol. 357:100-114; Adib-Conquuy et al. (1998) International Immunology 10:341-346; Lo Conte et al. (1999) J. Mol. Biol. 285:2177-2198; Zemlin et al. (2003) J. Mol. Biol. 334:733-749).

According to one embodiment of the invention an immunoglobulin obtainable by the method according to the invention is used for the preparation of a library with library members displaying or encoding the immunoglobulins according to the invention, specifically a library of proteins, fusion proteins, cells, in particular microbial cells, like bacterial or yeast cells, phages, viruses, nucleic acids or ribosomes.

The following specification not only refers to libraries of polypeptide or protein variants, but, of course, also to the alternative libraries used for expressing the immunoglobulins according to the invention, e.g. as mentioned above.

In one preferred embodiment, a library of polypeptide variants comprising immunoglobulins or immunoglobulin variable domains of the invention is used as a pool for selection wherein the modifications contain or introduce at least one, more preferably at least two amino acids per modified structural loop out of the group of amino acids tryptophane, tyrosine, phenylalanine, histidine, isoleucine, serine, methionine, alanine and asparagine.

It turned out that according to the invention a variant variable domain polypeptide can be provided with specific mutations that are foreign to the native polypeptides. Any of the amino acids tryptophane, tyrosine, phenylalanine, histidine, isoleucine, serine, methionine, alanine and asparagines are not present in the structural loops of human native immunoglobulins, thus are considered as "foreign". A variant polypeptide according to the invention may contain at least two of said foreign amino acids in the structural loops, by modification of at least one structural loop and to make up a binding site.

If the modified immunoglobulin or immunoglobulin variable domain is of human origin or a humanized immunoglobulin variable domain, preferred modifications are the incorporation of least one tyrosine in any one of the positions 12 to 17, 45 to 50, 69 to 75 and 93 to 98, and/or at least one tryptophane in any one of the positions 12 to 17, 45 to 50, 69, 71 to 75, 93 to 94 and 96 to 98, and/or at least one histidine in any one of the positions 12 to 17, 46, 47, 49, 50, 69 to 74 and 93 to 98, and/or at least one asparagine in any one of the positions 12 to 17, 45 to 47, 49, 50, 70 to 73, 75, 94 to 96 and 98, and/or at least one methionine in any one of the positions 12 to 17, 46 to 50, 69 to 71, 73 to 75, 93, 95, 96 and 98, and/or at least one serine in any one of the positions 13, 71, 75, 94, 95 and 98, and/or at least one isoleucine in any one of the positions 12, 14 to 17, 45 to 50, 69, 70, 72 to 75, 93 and 96 to 98, and/or at least one phenylalanine in any one of the positions 15, 46, 48, 70 to 73, 75, 93, 95 and 98.

According to another preferred embodiment of the present invention at least two amino acid residues in positions 15 to 17, 29 to 34, 85.4 to 85.3, 92 to 94, 97 to 98 and/or 108 to 110 of a human or humanized single domain antibody are modified.

The nucleic acid molecules encoding the modified immunoglobulins or immunoglobulin variable domains (and always included throughout the whole specification: immunoglobulins and immunoglobulin fragments comprising a modified immunoglobulin variable domain) may be cloned into host cells, expressed and assayed for their binding specificities. These practices are carried out using well-known procedures, and a variety of methods that may find use in the present invention are described in Molecular Cloning-A Laboratory Manual, 3.sup.rd Ed. (Maniatis, Cold Spring Harbor Laboratory Press, New York, 2001), and Current Protocols in Molecular Biology (John Wiley & Sons). The nucleic acids that encode the modified immunoglobulins or immunoglobulin variable domains of the present invention may be incorporated into an expression vector in order to express said immunoglobulins. Expression vectors typically comprise an immunoglobulin operably linked—that is placed in a functional relationship—with control or regulatory sequences, selectable markers, any fusion partners, and/or additional elements. The modified immunoglobulins of the present invention may be produced by culturing a host cell transformed with nucleic acid, preferably an expression vector, containing nucleic acid encoding the modified immunoglobulins, under the appropriate conditions to induce or cause expression of the modified immunoglobulins. The methods of introducing exogenous nucleic acid molecules into a host are well known in the art, and will vary with the host used. Of course, also non-cellular or cell-free expression systems for the expression of modified immunoglobulins may be employed.

In a preferred embodiment of the present invention, the modified immunoglobulins are purified or isolated after expression. Modified immunoglobulins may be isolated or purified in a variety of ways known to those skilled in the art. Standard purification methods include chromatographic techniques, electrophoretic, immunological, precipitation, dialysis, filtration, concentration, and chromatofocusing techniques. Purification can often be enabled by a particular fusion partner. For example, antibodies may be purified using glutathione resin if a GST fusion is employed, $Ni^{2+}$-affinity chromatography if a His-tag is employed or immobilized anti-flag antibody if a flag-tag is used. For general guidance in suitable purification techniques, see e.g. Scopes, "Protein Purification: Principles and Practice", 1994, $3^{rd}$ ed., Springer-Science and Business Media Inc., NY or Roe, "Protein Purification Techniques: A Practical Approach", 2001, Oxford University Press. Of course, it is also possible to express the modified immunoglobulins according to the present invention on the surface of a host, in particular on the surface of a bacterial, insect or yeast cell or on the surface of phages or viruses.

Modified immunoglobulins of the invention may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an enzyme, an immune label, isotopic label, or small molecule label such as a fluorescent or calorimetric dye or a luminogenic molecule.

In a preferred embodiment, the functional and/or biophysical properties of the immunoglobulins are screened in an in vitro assay. In a preferred embodiment, the antibody is screened for functionality, for example its ability to catalyze a reaction or its binding specificity, cross reactivity and/or affinity to its target.

In another preferred embodiment, the favourable modified immunoglobulin domains may be selected in vivo, e.g. by introducing it into a cell or an organism. The specifically binding variants may be isolated either from body fluid such as blood or lymphatic liquid or from specific organs, depending on the required properties of the modified domains.

Assays may employ a variety of detection methods including but not limited to chromogenic, fluorescent, luminescent, or isotopic labels.

As is well known in the art, there are a variety of selection technologies that may be used for the identification and isolation of proteins with certain binding characteristics and affinities, including, for example, display technologies such as phage display, ribosome display, cell surface display, and the like, as described below. Methods for production and screening of antibody variants are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76.

As is known in the art, some screening methods select for favourable members of a library. The methods are herein referred to as "selection methods", and these methods find use in the present invention for screening modified immunoglobulins. When variant immunoglobulin variable domain libraries are screened using a selection method, only those members of a library that are favourable, that is which meet some selection criteria, are propagated, isolated, and/or observed. As will be appreciated, because only the fittest variants are observed, such methods enable the screening of libraries that are larger than those screenable by methods that assay the fitness of library members individually. Selection is enabled by any method, technique, or fusion partner that links, covalently or non-covalently, the phenotype of immunoglobulins with its genotype that is the function of an antibody with the nucleic acid that encodes it. For example the use of phage display as a selection method is enabled by the fusion of library members to a phage coat protein (most frequently used is the filamentous bacteriophage gene III protein, however also other coat proteins such as protein VIII, protein VII, protein VI and protein IX can be used). In this way, selection or isolation of modified immunoglobulins that meet some criteria, for example binding affinity to the immunoglobulin's target, also selects for or isolates the nucleic acid that encodes it. Once isolated, the gene or genes encoding modified immunoglobulins may then be amplified. This process of isolation and amplification, referred to as panning, may be repeated, allowing favourable antibody variable domain variants in the library to be enriched. Nucleic acid sequencing of the attached nucleic acid ultimately allows for gene identification.

A variety of selection methods are known in the art that may find use in the present invention for screening immunoglobulin or immunoglobulin variable domain libraries. These include but are not limited to phage display (Phage display of peptides and antibodies: a laboratory manual, Kay et al., 1996, Academic Press, San Diego, Calif., 1996; Lowman et al., 1991, Biochemistry 30:10832-10838; Smith, 1985, Science 228:1315-1317) and its derivatives such as selective phage infection (Malmborg et al., 1997, J Mol Biol 273:544-551), selectively infective phage (Krebber et al., 1997, J Mol Biol 268:619-630), and delayed infectivity panning (Benhar et al., 2000, J Mol Biol 301:893-904), cell surface display (Witrrup, 2001, Curr Opin Biotechnol, 12:395-399) such as display on bacteria (Georgiou et al., 1997, Nat Biotechnol 15:29-34; Georgiou et al., 1993, Trends Biotechnol 11:6-10; Lee et al., 2000, Nat Biotechnol 18:645-648; Jun et al., 1998, Nat Biotechnol 16:576-80), yeast (Boder & Wittrup, 2000, Methods Enzymol 328:430-44; Boder & Wittrup, 1997, Nat Biotechnol 15:553-557), and mammalian cells (Whitehorn et al., 1995, Bio/technology 13:1215-1219), as well as in vitro display technologies (Amstutz et al., 2001, Curr Opin Biotechnol 12:400-405) such as polysome display (Mattheakis et al., 1994, Proc Natl Acad Sci USA 91:9022-9026), ribosome display (Hanes et al., 1997, Proc Natl Acad Sci USA 94:4937-4942), mRNA display (Roberts & Szostak, 1997, Proc Natl Acad Sci USA 94:12297-12302; Nemoto et al., 1997, FEBS Lett 414:405-408), and ribosome-inactivation display system (Zhou et al., 2002, J Am Chem Soc 124, 538-543).

Other selection methods that may find use in the present invention include methods that do not rely on display, such as in vivo methods including but not limited to periplasmic expression and cytometric screening (Chen et al., 2001, Nat Biotechnol 19:537-542), the antibody fragment complementation assay (Johnsson & Varshavsky, 1994, Proc Natl Acad Sci USA 91:10340-10344; Pelletier et al., 1998, Proc Natl Acad Sci USA 95:12141-12146), and the yeast two hybrid screen (Fields & Song, 1989, Nature 340:245-246) used in selection mode (Visintin et al., 1999, Proc Natl Acad Sci USA 96:11723-11728). In an alternate embodiment, selection is enabled by a fusion partner that binds to a specific sequence on the expression vector, thus linking covalently or noncovalently the fusion partner and associated immunoglobulin library member with the nucleic acid that encodes them. For example, WO9308278 describe such a fusion partner and technique that may find use in the present invention. In an alternative embodiment, in vivo selection can occur if expression of the antibody imparts some growth, reproduction, or survival advantage to the cell.

Some selection methods are referred to as "directed evolution" methods. Those methods include the mating or breeding of favourable sequences during selection, sometimes with the incorporation of new mutations. As will be appreciated by those skilled in the art, directed evolution methods can facilitate identification of the most favourable sequences in a plurality of polypeptides, and can increase the diversity of sequences that are screened. A variety of directed evolution methods are known in the art that may find use in the present invention for generating and screening antibody variable domain variants, including but not limited to DNA shuffling (PCT WO00/42561; PCT WO 01/70947), exon shuffling (Kolkman & Stemmer, 2001, Nat Biotechnol 19:423-428), family shuffling (Crameri et al., 1998, Nature 391:288-291), selective combinatorial randomization (WO03012100, WO04018674A1), Random Chimerageneis on Transient Templates (Coco et al., 2001, Nat Biotechnol 19:354-359), molecular evolution by staggered extension process (StEP) in vitro recombination (Zhao et al., 1998, Nat Biotechnol 16:258-261; Shao et al., 1998, Nucleic Acids Res 26:681-683), exonuclease mediated gene assembly (U.S. Pat. No. 6,352,842; U.S. Pat. No. 6,361,974), Gene Site Saturation Mutagenesis (U.S. Pat. No. 6,358,709), Gene Reassembly (U.S. Pat. No. 6,358,709), SCRATCHY (Lutz et al., 2001, Proc Natl Acad Sci USA 98:11248-11253), DNA fragmentation methods (Kikuchi et al., Gene 236:159-167), single-stranded DNA shuffling (Kikuchi et al., 2000, Gene 243:133-137), and directed evolution antibody engineering technology (Applied Molecular Evolution) (U.S. Pat. No. 5,824,514; U.S. Pat. No. 5,817,483; U.S. Pat. No. 5,814,476; U.S. Pat. No. 5,763,192; U.S. Pat. No. 5,723,323).

In a preferred embodiment, immunoglobulins or antibody variable domain variants are screened using one or more cell-based or in vivo assays. For such assays, purified or non-purified modified immunoglobulins or immunoglobulin variable domains are typically added exogenously such that cells are exposed to individual immunoglobulins or modified immunoglobulin variable domains or pools of modified immunoglobulin variable domains belonging to a library. These assays are typically, but not always, based on the desired function of the immunoglobulin or immunoglobulin variable domain; that is, the ability of the antibody or antibody variable domain modified according to the invention to bind to its target and to mediate some biochemical event, for example effector function, ligand/receptor binding inhibition, apoptosis, and the like. Such assays often involve monitoring the response of cells to the antibody variable domain, for example cell survival, cell death, change in cellular morphology, or transcriptional activation such as cellular expression of a natural gene or reporter gene. For example, such assays may measure the ability of variable immunoglobulin domain variants to elicit ADCC, ADCP or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Immunoglobulins may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable to measure apoptosis, and uptake or release of radioactive substrates or fluorescent dyes may enable cell growth or activation to be monitored.

Alternatively, dead or damaged target cells may be monitored by measuring the release of one or more natural intracellular components, e.g. lactate dehydrogenase. Transcriptional activation may also serve as a method for assaying function in cell-based assays. In this case, response may be monitored by assaying for natural genes which may be upregulated, for example the release of certain interleukins may be measured, or alternatively readout may be via a reporter system. Cell-based assays may also involve the measure of morphological changes of cells as a response to the presence of modified immunoglobulin variable domains. Cell types for such assays may be prokaryotic or eukaryotic, and a variety of cell lines that are known in the art may be employed.

Alternatively, cell-based screens may be performed using cells that have been transformed or transfected with nucleic acids encoding the variant immunoglobulin variable domains. In this case, antibody variable domain variants of the invention are not added exogenously to the cells (e.g. Auf der Maur, 2004, Methods, 34:215-224). In another alternative method, the cell-based screen utilizes cell surface display. A fusion partner can be employed that enables display of modified immunoglobulin variable domains on the surface of cells (Witrrup, 2001, Curr Opin Biotechnol, 12:395-399).

In a preferred embodiment, the immunogenicity of the modified immunoglobulins may be changed and determined experimentally using one or more immunological or cell based assays (e.g. Koren et al., 2002, Current Pharmaceutical Biotechnology 3:349-360; Chirino et al., 2004, Drug Discovery Today 9:82-90; Tangri et al., 2005, J. Immunol. 174:3187-3196; Hermeling et al., 2004, Pharm. Res. 21:897-903). In a preferred embodiment, ex vivo T-cell activation assays are used to experimentally quantitate immunogenicity. In this method, antigen-presenting cells and naive T-cells from matched donors are challenged with a peptide or whole antibody or immunoglobulin of interest one or more times. T-cell activation can be detected using a number of methods, e.g. by monitoring of cytokine release or measuring uptake of tritiated thymidine. In preferred embodiments, LUMINEX technology is used to measure cytokine release (e.g. de Jager et al., Clin. Diagn. Lab. Immunol., 2003, 10:133-139) or interferon gamma production is monitored using Elispot assays (Schmittel et. al., 2000, J. Immunol. Meth., 24: 17-24).

The biological or functional properties of the modified immunoglobulins or immunoglobulin variable domains of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including genetic knock-in and knock-out mutants). Such experimentation may provide meaningful data for determination of the potential of the polypeptide variant to be used as a therapeutic. Any organism, preferably mammals, may be used for testing. Because of their genetic similarity to humans, monkeys can be suitable therapeutic models, and thus may be used to test the efficacy, toxicity, pharmacokinetics, or other property of the modified immunoglobulins of the present invention. Testing drug candidates in humans are mostly required for approval as therapeutics, and thus of course these experiments are contemplated. Thus the modified immunoglobulins or immunoglobulin variable domains of the present invention may be tested in humans to determine their therapeutic efficacy, toxicity, immunogenicity, pharmacokinetics, pharmacodynamics and/or other clinical properties.

The immunoglobulin according to the present invention may be used for any purpose known in the art for immunoglobulins but also enables applications which are depending on the combination of specificities introduced by the present invention.

In one embodiment the antibody variant of the present invention is used for therapy or prophylaxis, for preparative or analytic use, as a diagnostic, an industrial compound or a research reagent, preferably a therapeutic. The antibody variant may find use in an antibody composition that is monoclonal, oligoclonal or polyclonal. In a preferred embodiment, the modified immunoglobulins or immunoglobulin variable domains of the present invention are used to kill target cells that bear the target antigen, for example cancer cells. In an alternate embodiment, the modified immunoglobulins of the present invention are used to block, antagonize, or agonize the target antigen, for example by antagonizing a cytokine or cytokine receptor. In an alternately preferred embodiment, the modified immunoglobulins of the present invention are used to block, antagonize, or agonize the target antigen and kill the target cells that bear the target antigen.

In an alternately preferred embodiment, the modified immunoglobulins of the present invention are used to block, antagonize, or agonize growth factors or growth factor receptors and kill the target cells that bear or need the target antigen. In an alternately preferred embodiment, the modified immunoglobulins of the present invention are used to block, antagonize, or agonize enzymes and substrate of enzymes. In another alternatively preferred embodiment, the modified immunoglobulin variable domains of the present invention are used to neutralize infectious agents such as viruses, small viruses, prions, bacteria or fungi.

The modified immunoglobulins or immunoglobulins variable domains of the present invention may be used for various therapeutic purposes. In a preferred embodiment, an antibody comprising the modified immunoglobulin or immunoglobulin variable domain is administered to a patient to treat a specific disorder. A "patient" for the purposes of the present invention includes both, humans and other animals, preferably mammals and most preferably humans. By "specific disorder" herein is meant a disorder that may be ameliorated by the administration of a pharmaceutical composition comprising a modified immunoglobulin or immunoglobulin variable domain of the present invention.

In one embodiment, a modified immunoglobulin or immunoglobulin variable domain according to the present invention is the only therapeutically active agent administered to a patient. Alternatively, the modified immunoglobulin or immunoglobulin variable domain according the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The modified immunoglobulin or immunoglobulin variable domain may be administered concomitantly with one or more other therapeutic regimens. For example, an antibody variant of the present invention may be formulated and administered to the patient along with chemotherapy, radiation therapy, or both chemotherapy and radiation therapy. In one embodiment, the modified immunoglobulin or immunoglobulin variable domain of the present invention may be administered in conjunction with one or more antibodies, which may or may not comprise an antibody variant of the present invention. In accordance with another embodiment of the invention, the modified immunoglobulin or immunoglobulin variable domain of the present invention and one or more other anti-cancer therapies are employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the modified immunoglobulins of the present invention. In one embodiment, the modified immunoglobulin is administered with an anti-angiogenic agent, which is a compound that blocks, or interferes to some degree with the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the modified immunoglobulin is administered with a therapeutic agent that induces or enhances adaptive immune response, for example an antibody that targets CTLA-4. In an alternate embodiment, the modified immunoglobulin is administered with a tyrosine kinase inhibitor, which is a molecule that inhibits to some extent tyrosine kinase activity of a tyrosine kinase. In an alternate embodiment, the modified immunoglobulins of the present invention are administered with a cytokine. By "cytokine" as used herein is meant a generic term for proteins released by one cell population that act on another cell as intercellular mediators including chemokines.

Pharmaceutical compositions are contemplated wherein modified immunoglobulins of the present invention and one or more therapeutically active agents are formulated. Formulations of the polypeptide variants of the present invention are prepared for storage by mixing said modified immunoglobulin or immunoglobulin variable domain having the desired degree of purity with optional pharmaceutically acceptable carriers, excipients or stabilizers (Remington's Pharmaceutical Sciences, 1980, 16$^{th}$ edition, Osol, A. Ed.,), in the form of lyophilized formulations or aqueous solutions. The formulations to be used for in vivo administration are preferably sterile. This is readily accomplished by filtration through sterile filtration membranes or other methods. The modified immunoglobulins and other therapeutically active agents disclosed herein may also be formulated as immunoliposomes, and/or entrapped in microcapsules.

Administration of the pharmaceutical composition comprising a modified immunoglobulin or immunoglobulin variable domain of the present invention, preferably in the form of a sterile aqueous solution, may be performed in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly.

Another aspect of the present invention relates to a method for manufacturing a molecule comprised of an immunoglobulin or immunoglobulin variable domain or a pharmaceutical preparation thereof comprising at least one modification in each of two structural loops or loop regions of said immunoglobulin or immunoglobulin variable domain and determining the binding of said molecule to an epitope of an antigen, wherein the unmodified molecule does not significantly bind to said epitope, comprising the steps of:
providing a nucleic acid encoding an immunoglobulin variable domain comprising at least two structural loops or loop regions,
modifying at least one nucleotide residue in each of said structural loops or loop regions,
transferring said modified nucleic acid in an expression system,
expressing said modified immunoglobulin,
contacting the expressed modified immunoglobulin with an epitope,
determining whether said modified immunoglobulin binds to said epitope, and
providing the modified immunoglobulin binding to said epitope and optionally finishing it to a pharmaceutical preparation.

In particular the present invention relates to a method for manufacturing a multi-specific molecule binding specifically to at least one first molecule or a pharmaceutical preparation thereof comprising at least one modification in each of at least two structural loops or loop regions of an immunoglobulin or immunoglobulin variable domain and determining the specific binding of said at least two loops or loop regions to at least one second molecule selected from antigens. The immunoglobulin or immunoglobulin variable domain containing an unmodified structural loops or loop regions does not specifically bind to said at least one second molecule.

The method specifically comprises the steps of:

providing a nucleic acid encoding an immunoglobulin binding specifically to at least one first molecule comprising at least one structural loops or loop regions,
modifying at least one nucleotide residue of at least one of said loops or loop regions encoded by said nucleic acid,
transferring said modified nucleic acid in an expression system,
expressing said modified immunoglobulin,
contacting the expressed modified immunoglobulin with said at least one second molecule, and
determining whether said modified immunoglobulin binds specifically to the second molecule and
providing the modified immunoglobulin binding specifically to said at least one second molecule and optionally finishing it to a pharmaceutical preparation.

The engineering of more than one binding site or at least two specificities into a member of a specific binding pair is preferred (Kufer et al. (2004) Trends in Biotechnology vol. 22 pages 238-244).

Numerous attempts have been made to produce multispecific, e.g. bispecific, monoclonal antibodies or antibody fragments. One problem in the production of bispecific antibodies made of two different polypeptide chains (heavy and light chain) is the necessity to express four different chains (two heavy and two light chains) in one cell resulting in a number of various combinations of molecules which have to be separated from the desired bispecific molecule in the mixture. Due to their similarity the separation of these molecules is difficult and expensive. A number of techniques have been employed to minimize the occurrence of such unwanted pairings (Carter (2001) Journal of Immunological Methods, vol 248, pages 7-15)

One solution to the problem is the production of one polypeptide chain with two specificities, like e.g. two scFvs linked to each other or the production of so-called diabodies. Such molecules have been shown to be far away from the fold of a natural molecule and are notoriously difficult to produce (LeGall et al. (2004) Protein Engineering, Design & Selection vol 17 pages 357-366).

According to a preferred embodiment of the present invention the expression system comprises a vector. Any expression vector known in the art may be used for this purpose as appropriate.

The modified immunoglobulin is preferably expressed in a host, preferably in a bacterium, in yeast, in a plant cell, in an insect cell, in an animal cell or mammalian cell or in an organ of a plant or animal or in a complete plant or animal.

A wide variety of appropriate host cells may be used to express the modified polypeptide of the invention, including but not limited to mammalian cells (animal cells) plant cells, bacteria (e.g. *Bacillus subtilis, Escherichia coli*), insect cells, and yeast (e.g. *Pichia pastoris, Saccharomyces cerevisiae*). For example, a variety of cell lines that may find use in the present invention are described in the ATCC cell line catalog, available from the American Type Culture Collection. Furthermore, also plants and animals may be used as hosts for the expression of the immunoglobulin according to the present invention. The expression as well as the transfection vectors or cassettes may be selected according to the host used.

Of course also non-cellular or cell-free protein expression systems may be used. In vitro transcription/translation protein expression platforms, that produce sufficient amounts of protein offer many advantages of a cell-free protein expression, eliminating the need for laborious up- and down-stream steps (e.g. host cell transformation, culturing, or lysis) typically associated with cell-based expression systems.

Another problem of the current design of bispecific antibodies is the fact that even if the parent antibodies are bivalently binding to their respective binding partner (e.g. IgG), the resulting bispecific antibody is monovalent for each of the respective binding partner.

The preferred multi-specific molecules of the present invention solve these problems:

Expression of a bispecific molecule as one polypeptide chain is possible (a modified immunoglobulin variable domain with two binding specificities, see example section), which is easier to accomplish than the expression of two antibody polypeptide chains (Cabilly et al. Proc. Natl. Acad. Sci. USA 81:3273-3277 (1984).

It can also be produced as an antibody like molecule (i.e. made of 2 polypeptide chains). Due to the fact that the second specificity is located in the non-CDR part of the variable domains there is no need for two different heavy chains or different light chains. Thus, there is no possibility of wrong pairing of the two chains.

An antibody of the present invention may consist of a heavy chain and a light chain, which form together a variable CDR loop region binding to a specific binding partner, i.e. a specific CDR loop conformation, and the second specificity may be formed by modified structural loops or loop regions contained in the immunoglobulin molecule, e.g. the structural loops of either the heavy chain or the light chain variable domain, while maintaining the specific CDR loop conformation. The binding site may also be formed by at least one or more than one non-CDR loops on two variable domains (e.g. a heavy chain variable domain and a light chain variable domain which may be structurally neighbored).

The modified antibody may be a complete antibody or an antibody fragment (e.g. Fab, scFv, Fv, minibody, dAb) comprising at least one immunoglobulin variable domain and modifications in the structural loops or loop regions, or derivatives thereof.

It may bind mono- or multivalently to binding partners or even with different valency for the different binding partners, depending on the design. For example, an Fab fragment or, equivalently an scFv may be engineered in such a way that the structural loops of the VH and the VL domains are separately engineered to bind to the same epitope as the binding site formed by the CDRs, resulting in a trivalent Fab fragment or scFv respectively. In another embodiment, a complete immunoglobulin containing the same engineered VH and VL domains will bind hexavalently to its target epitope. If for example the natural binding site formed by the CDRs recognizes a different target epitope than the engineered Vh and Vl domains then the resulting Fab fragment or scFv will bind monovalently to the first target, and bivalently to the second target which is bound independently by the modified structural loops of the VH and the VL domain respectively. This modular design principle can be applied in numerous different ways as will be obvious to those skilled in the art.

As there are a number of various structural loops available for selection and design of a specific binding site in the non-CDR regions of heavy and light domains it is possible to design antibody derivatives with even more than two specificities. For example, VH and VL domains recognizing a first target by their CDRs can be engineered separately to bind specifically to different (second and third) targets through interactions mediated by the modified structural loops. Thus, a trispecific Fab fragment or scFv, which binds monovalenty to each of its target can be generated. If the modified variable domains of this Fab are engineered in the form of a full size IgG, an engineered IgG is generated which is trispecific and, to each if its three specificities, binds bivalently.

The specific binding domains within one polypeptide chain may be connected with or without a peptide linker.

Some antibody classes can be regarded as multi-specific, in particular bispecific, by nature: They bind to an antigen (which is typically e.g. either a foreign structure or a cancer associated structure) with the variable region and they bind to Fc-effector molecules with the Fc part (e.g. Fc receptors on various immune cells or complement protein) thus enabling effects such as ADCC, ADCP or CDC.

The Fc-effector molecules are bound by the Fc-part of an immunoglobulin molecule (for IgG1 it consists of domains CH2 and CH3) and a number of methods have been described to optimize effector function by improvement of binding of the Fc-part of an antibody molecule either by glycoengineering techniques (U.S. Pat. No. 6,602,684) or by protein engineering either directly at the Fc (US 2005/0054832) or indirectly by engineering outside the Fc (US 2005/02444403). Both, binding of the Fc region to Fc receptor and/or binding to complement proteins such Cq1 has been altered by such techniques. Usually one tries to improve the binding affinity to such Fc-effector molecules as this correlates with improved effector functions.

With the current invention it is possible to design an antibody binding to Fc-effector molecules outside the natural Fc binding region. Modified loops in antibody variable domains other than the loops involved in "natural" Fc-effector molecule binding can be selected from a library of modified loop structures or designed to bind to one or more Fc-effector molecules. An antibody with such additional Fc-effector molecule binding sites would either have stronger avidity to a certain Fc-effector molecule or effector-cell displaying an Fc-effector molecule and therefore may have an even stronger effect than glycoengineered antibodies or otherwise improved Fc regions.

Antibody fragments have certain advantages as compared to whole antibodies. Fragments have usually good biodistribution properties and can more easily be produced. However, most of the antibody fragment designs lack effector functions and have short in vivo half life (Holliger P, et al. Nat Biotechnol. (2005) 23:1126-36.). Neither CH1 nor Cκ or Cλ domains are able to mediate effector functions, which is the reason why Fab molecules usually do not show ADCC, ADCP or CDC.

WO 02/44215 describes binding molecules which consist of the antigen binding site of an antibody and a peptide binding Fc-effector molecules. In such a way an antibody fragment displaying effector functions can be constructed. The peptide is being incorporated into the binding molecule at a position that does neither destroy the antigen binding nor the ability of the peptide to bind to an Fc-effector molecule.

According to the present invention however, the binding to Fc-effector molecules may be performed with modified immunoglobulins or immunoglobulin variable domains which have been selected for Fc-effector molecule binding from libraries of two, three or four randomized structural loop sequences within a fixed scaffold of an immunoglobulin or immunoglobulin variable domain. Therefore, it is possible to select for specific loop sequences which would not bind to Fc-effector molecules if isolated from the Ig-domain scaffold. The polypeptides resulting from the present invention may therefore preferably consist of more than 100 amino acids and may comprise one or more immunoglobulin variable domains.

In order to select for potential effector function of such variable domains according to the present invention, antibody- or antibody fragment libraries comprising mutant variable domains may be selected for binding to Fc-receptors and/or complement factors such as C1q. Fcgamma receptors for selection may be provided either on the surface of cells expressing naturally the respective receptors or by expression and purification of the extracellular part of the respective receptor. IFN-g stimulated U937 cells (CRL-1503, American Type Culture Collection) can be used as target cells for the isolation of phage displayed modified immunoglobulin variable domains that bind specifically to the high-affinity IgG receptor, FcgammaRI (Berntzen et al., 2006, Protein Eng Des Sel. 19(3):121-8). Binding to the Fc receptor can be tested for by FACS using U937 cells as target, which cells are stained specifically with selected modified immunoglobulin variable domains. Furthermore, the extracellular domains of human Fcgamma receptors can be cloned and expressed as soluble proteins or fusion proteins and used for analysis of the specific binding of potential binding partners (e.g. as in Berntzen et al., 2005, J Immunol Methods. 298(1-2):93-104). The identification and characterisation of modified immunoglobulin variable domains specifically binding to complement factor C1q can be performed essentially similarly (e.g. as in Lauvrak et al. 1997 Biol Chem. 378(12):1509-19).

In order to increase in vivo half life of a molecule consisting of or containing such a variable domain binding to FcRn or serum albumin may be selected for with libraries of mutant variable domains according to the present invention. Those modified structural loops responsible for extending the half life of a molecule through its specific binding to serum proteins or complement proteins can be used as isolated structural loops or in the context of an immunoglobulin or parts thereof, for combination with those molecules that are to be designed as molecules with increased half life in vivo.

FcRn receptors or other cell receptors for selection may be provided either on the surface of cells expressing naturally the respective receptors or by expression and purification of the extracellular part of the respective receptor. For the purpose of this invention a first screening on FcRn may select for mutant variable domains (or molecules comprising such mutant variable domains) which can further be tested in vitro and even further characterized in FACS experiments by binding to cells expressing FcRn receptor. Screening and selection may also consider pH dependencies in binding to FcRn (as described in PCT WO02/060919; PCT WO97/34631). It can be further characterized by affinity ranking of binding to various recombinant FcRn, isoforms and allotypes e.g. with surface plasmon resonance techniques (e.g. as in Dall' Acqua et al. Journal of Immunology, 2002, 169: 5171-5180).

The modified immunoglobulin according to the invention may comprise a heavy and/or light chain, or parts thereof, and at least one variable domain.

The immunoglobulin according to the present invention comprises preferably at least one constant and/or at least one variable domain of the immunoglobulin, or a part thereof.

A variable domain usually is considered an immunoglobulin fold unit of the variable part of an immunoglobulin, also referred to as a domain of the variable region (e.g. VH, Vk, Vl, Vd)

Another preferred immunoglobulin according to the invention consists of a variable domain of a heavy or light chain, or a part thereof, with at least two structural loops or loop regions, and is characterised in that said at least two structural loops or loop regions comprise at least two amino acid modifications forming at least two modified structural loops or loop regions, wherein said at least two modified structural loops or loop regions bind specifically to at least one epitope of an antigen. In such a preferred immunoglobulin according to the invention the at least two amino acid modifications may be located in one or two structural loops or loop regions or at one or two structural loops so to make up a binding site for an antigen.

According to a preferred embodiment of the present invention the specific binding of the modified polypeptide to a molecule is determined by a binding assay selected from the group consisting of immunological assays, preferably enzyme linked immunosorbent assays (ELISA), surface plasmon resonance assays, saturation transfer difference nuclear magnetic resonance spectroscopy, transfer NOE (trNOE) nuclear magnetic resonance spectroscopy, competitive assays, tissue binding assays, live cell binding assays and cellular extract assays.

Binding assays can be carried out using a variety of methods known in the art, including but not limited to FRET (Fluorescence Resonance Energy Transfer) and BRET (Bioluminescence Resonance Energy Transfer)-based assays, Amplified Luminescent Proximity Homogeneous Assay, Scintillation Proximity Assay, ELISA (Enzyme-Linked Immunosorbent Assay), SPR (Surface Plasmon Resonance), isothermal titration calorimetry, differential scanning calorimetry, gel electrophoresis, and chromatography including gel filtration.

The modified polypeptide of the invention is preferably conjugated to a label selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof.

Modified polypeptides conjugated to labels as specified above may be used, for instance, in diagnostic methods.

The modified immunoglobulin may be conjugated to other molecules which allow the simple detection of said conjugate in, for instance, binding assays (e.g. ELISA) and binding studies.

Another aspect of the present invention relates to a polypeptide comprising a variable domain of a light or heavy chain or combinations thereof, with at least two loops or loop regions, characterised in that said at least two structural loops or loop regions each comprise at least one amino acid modification forming at least two modified structural loops or loop regions, wherein said at least two modified structural loops or loop regions bind specifically to at least one epitope of an antigen.

It is preferred to combine molecularly at least one modified antibody variable domain (=binding to the specific partner via the non-variable sequences or structural loops) with at least one other binding molecule which can be an antibody, antibody fragment, a soluble receptor, a ligand or another modified antibody domain.

The other binding molecule combined with the at least one modified antibody variable domain of the invention is selected from the group consisting of proteinaceous molecules, nucleic acids, and carbohydrates.

The structural loops or loop regions of the modified immunoglobulin according to the invention may specifically bind to any kind of binding molecules, in particular to proteinaceous molecules, proteins, peptides, polypeptides, nucleic acids, glycans, carbohydrates, lipids, small and large organic molecules, inorganic molecules. Of course, the modified immunoglobulin according to the invention may comprise at least two loops or loop regions whereby each of the loops or loop regions may specifically bind to different molecules or epitopes.

Another aspect of the present invention relates to the use of an immunoglobulin or immunoglobulin variable domain according to the present invention or obtainable by a method according to the present invention for the preparation of a vaccine for active immunization. Hereby the immunoglobulin is either used as antigenic drug substance to formulate a vaccine or used for fishing or capturing antigenic structures for use in a vaccine formulation.

Another aspect of the present invention relates to the use of an immunoglobulin according to the present invention or obtainable by a method according to the present invention for the preparation of a library of polypeptides comprising modified immunoglobulin variable domains.

Yet another aspect of the present invention relates to a method for specifically binding and/or detecting a target molecule comprising the steps of:
 (a) contacting a molecule comprising a modified immunoglobulin or immunoglobulin variable domain according to the present invention or a molecule comprising a modified immunoglobulin variable domain obtainable by a method according to the present invention with a test sample containing or suspected to contain said target molecule, and optionally
 (b) detecting the potential formation of a specific immunoglobulin/molecule or immunoglobulin variable domain/molecule complex.

A preferred method according to the invention is for specifically binding and/or detecting a molecule comprising the steps of:
 (a) contacting a library of modified immunoglobulins or a modified immunoglobulin according to the present invention with a test sample containing said molecule, and optionally
 (b) detecting the potential formation of a specific immunoglobulin/molecule complex.

Test samples may be human or animal sample, such as blood samples or other body fluids and cell suspensions, which sample possibly contains a target molecule to be specifically bound by immunoglobulins for capturing and/or detecting purposes.

Another aspect of the present invention relates to a method for specifically isolating a target molecule comprising the steps of:
 (a) contacting a molecule comprising a modified immunoglobulin or immunoglobulin variable domain according to the present invention or a molecule comprising a modified immunoglobulin variable domain obtainable by a method according to the present invention with a sample containing said target molecule,
 (b) separating the specific immunoglobulin variable domain/target molecule complex formed, and
 (c) optionally isolating the target molecule from said complex.

A preferred method according to the invention is for specifically isolating a modified immunoglobulin binding to a molecule comprising the steps of:
 (a) contacting a library of modified immunoglobulins according to the present invention with a sample containing said molecule,
 (b) separating the specific modified immunoglobulin/molecule complex formed, and
 (c) optionally isolating the modified immunoglobulin from said complex.

Those samples are usually considered sources for preparative isolating those molecules, for instance complex natural sources, like animal, human or plant sources or microbial derived sources or cell suspensions and cultures.

The immunoglobulins or immunoglobulin variable domains according to the present invention may be used to isolate specifically target molecules from a sample. If multi-specific immunoglobulins or immunoglobulin variable domains are used more than one target molecule may be isolated from a sample. It is especially advantageous using immunoglobulins or modified immunoglobulin variable domains in such methods because it allows, e.g., to generate a matrix having a homogeneous surface with defined amounts of binding partners (i.e. modified immunoglobulin variable domains) immobilised thereon which are able to bind to the target molecules to be isolated. In contrast thereto, if monospecific binding partners are used no homogeneous matrix can be generated because the single binding partners do not bind with the same efficiency to the matrix.

Another aspect of the present invention relates to a method for targeting a compound to a target comprising the steps of:
 (a) contacting a molecule comprising a modified immunoglobulin variable domain according to the present invention or a molecule comprising a modified immunoglobulin variable domain obtainable by a method according to the present invention capable to specifically bind to said compound,
 (b) delivering the molecule comprising an immunoglobulin variable domain/compound complex to the target.

Modified immunoglobulins or immunoglobulin variable domains according to the present invention may be used to deliver at least one compound bound to the CDRs by a specific CDR loop conformation to a target by binding to the modified structural loop region. Such immunoglobulins may be used to target therapeutic substances to a preferred site of action in the course of the treatment of a disease.

Another aspect of the present invention relates to a molecule library comprising, expressing or encoding an immunoglobulin or immunoglobulin variable domain according to the present invention or obtainable by the method according to the present invention.

The preferred library of immunoglobulins or immunoglobulin variable domains according to the invention comprises at least 10 immunoglobulins or immunoglobulin variable domains, preferably 100, more preferably 1000, more preferably 10000, more preferably 100000, most preferably more than 1000000 variant immunoglobulins or variable domains, with a modification in at least two structural loops or loop regions.

Usually libraries according to the invention comprise at least 10 fusion proteins or binding agents, preferably at least 100, more preferred at least 1000, more preferred at least $10^4$, more preferred at least $10^5$, more preferred at least $10^6$, more preferred at least $10^7$, more preferred at least $10^8$, more preferred at least $10^9$, more preferred at least $10^{10}$, more preferred at least $10^{11}$, up to $10^{12}$, in cases of ribosomal display even higher number are feasible.

It turned out that most preferred members of a library have mutations of at least 4, or even at least 5 or 6 amino acid positions in at least two structural loops or loop regions. Thus, the particularly preferred libraries according to the invention consist of members that have mutations of at least 2, 3 or 4 amino acid positions in at least two structural loops.

A library according to the invention may also comprises or consist of one of or a mixture of immunoglobulin variable domains selected from the group of VH, Vkappa, Vlambda and VHH, as suitable for the purpose of defining binding partners for commercial reasons.

Preferred methods for constructing said library can be found above and in the examples. The library according to the present invention may be used to identify immunoglobulins or immunoglobulin variable domains binding to a distinct molecule.

In particular the present invention relates to the use of a protein library of polypeptides comprising an immunoglobulins or immunoglobulin variable domain according to the present invention or obtainable by the method according to the present invention for the design of immunoglobulin derivatives. An existing immunoglobulin can be changed to introduce antigen binding sites into an immunoglobulin or a variable domain by using a protein library of the respective immunoglobulin or variable domain of at least 10, preferably 100, more preferably 1000, more preferably 10000, more preferably 100000, most preferably more than 1000000 immunoglobulins or variant variable domains each with at least two modified structural loops. The library is then screened for binding to the specific antigen. After molecular characterization for the desired properties the selected immunoglobulin or variable domain is cloned into the original immunoglobulin by genetic engineering techniques so that it replaces the wild type region. Alternatively, only the DNA coding for the modified loops or coding for the mutated amino acids may be exchanged to obtain an immunoglobulin with the additional binding site for the specific antigen. Alternatively, the modification in the structural loops of the variable domains may be performed with the variable domain in its natural context, e.g. in the form of a Fab, scFv, or complete immunoglobulin molecule. Except when single domain immunoglobulins, a chain of single immunoglobulin domains or single chain immunoglobulins, such as scFv or unibodies (monovalent immunoglobulin fragments) are produced, usually the immunoglobulin according to the invention is provided as a dimer, preferably as a heterodimer.

The choice of the site for the mutated, antigen-specific structural loop is dependent on the structure of the original immunoglobulin and on the purpose of the additional binding site. If, for example, the original or parent immunoglobulin is a Fab or scFv, modification of at least two structural loops in the variable domains of the light chain and/or the heavy chain is possible, but also modification of at least two structural loops in the CH1/CL is preferred to produce an immunoglobulin according to the invention. Thus, the Fab molecule according to the invention may contain the new binding site through a modified loop region in the CH1 and or the CL domain. In this context it is usually of primary importance to maintain the specific CDR loop conformation and natural binding properties of the parent immunoglobulin, scFv or Fab.

To generate a library one may prepare libraries of mutant original molecules which have mutations in two or more structural loops of one or more variable domains. The selection with complete mutated original molecules may have some advantages as the selection for antigen binding with a modified structural loop will deliver the sterically advantageous modifications. For example, if the complete molecule is a scFv, it may be advantageous to screen the library of mutated original scFv for binding to an antigen, followed by screening the specific binders for binding to the antigen which is recognized by the CDR loops (original specificity). In an alternative selection procedure the original—the first— antigen may be bound to the CDR-loops during the screening for binding to an antigen with the modified structural loops. This simultaneous screening may allow for rescuing of clones that would be lost during a sequential selection procedure if the binding to the antigen is influenced by the binding to the first antigen.

A preferred embodiment of the invention is a library of variant immunoglobulins containing or consisting of variable domains with at least one variant amino acid position in each of at least two of the structural loops. The library may comprise immunoglobulin domains of the heavy and the light chain or mixtures and molecular combinations thereof.

Another preferred embodiment is a library containing or consisting of VHH domains or humanized forms of such camelid domains with at least one variant amino acid position in each of at least two structural loops or loop regions.

Another preferred embodiment of the invention is a library containing or consisting of single chain antibodies, such as a scFv library with at least one variant amino acid position in each of at least two of the structural loops or loop regions of any of the variable domains of the single chain antibody or scFv.

Another preferred embodiment of the invention is a diabody library containing or consisting of at least one variant amino acid position in each of at least two of the structural loops or loop regions of any of the variable domains of the diabody.

Another preferred embodiment of the invention is a minibody library containing or consisting of at least one variant amino acid position in each of at least two of the structural loops or loop regions of any of the variable domains of the minibody.

Yet another preferred embodiment of the invention is a Fab library containing or consisting of at least one variant amino acid position in each of at least two of the structural loops or loop regions of any of the variable domains of the Fab.

Yet another preferred embodiment of the invention is an antibody or IgG library, preferably a human antibody library, containing or consisting of at least one variant amino acid position in each of at least two of the structural loops or loop regions of any of the variable domains of the antibody or IgG domains.

The size requirement (i.e. the number of variants) of a library according to the invention, comprising differently mutated immunoglobulins or immunoglobulin variable domains or fusion molecules of mutated variable antibody domains is dependent on the task. In general, a library to generate an antigen binding site de novo needs to be larger than a library used to further modify an already existing engineered antigen binding site formed by a modified structural loop or loop region (e.g. for enhancing affinity or changing fine specificity to the antigen).

The present invention also relates to a polypeptide library or a nucleic acid library comprising a plurality of polypeptides comprising immunoglobulins or immunoglobulin variable domains or at least two structural loops or loop regions contained in a minidomain, or nucleic acid molecules encoding the same. The library contains members with different modifications, wherein the plurality is defined by the modifications in the at least two structural loops or loop regions. The nucleic acid library preferably includes at least 10 different members (with at least two potential amino acid modifications) and more preferably includes at least 100, more preferably 1000 or 10000 different members (e.g. designed by randomization strategies or combinatory techniques). Even more diversified individual member numbers, such as at least 1000000 or at least 10000000 are also preferred, more preferred at least $10^8$, more preferred at least $10^9$, more preferred at least $10^{10}$, more preferred at least $10^{11}$, up to $10^{12}$, in cases of ribosomal display even higher number are feasible.

A further aspect of the invention is the combination of two different immunoglobulins or immunoglobulin variable domains selected from at least two libraries according to the invention in order to generate multispecific immunoglobulins. These selected specific immunoglobulin variable domains may be combined with each other and with other molecules, similar to building blocks, to design the optimal arrangement of the domains to get the desired properties such as combinations of specificities and/or valencies.

Furthermore, one or more modified immunoglobulins or immunoglobulin variable domains according to the invention may be introduced at various or all the different sites of a protein without destruction of the structure of the protein. By such a "domain shuffling" technique new libraries are created which can again be selected for the desired properties.

The preferred library contains immunoglobulins or immunoglobulin variable domains according to the invention or derivatives thereof.

A preferred embodiment of the present invention is a binding molecule for an antigen (antigen binding molecule) comprising at least one immunoglobulin or immunoglobulin variable domain and at least two structural loops or loop regions being modified according to the present invention to bind to the antigen, wherein said binding molecule has no relevant and/or specific binding activity with its CDR-loops. It may comprise other parts useable for antibody activities (e.g. such as natural or modified effector regions (sequences); however, it lacks the "natural" binding region of antibodies, i.e. active CDR-loops in their naturally occurring position. These antigen binding molecules according to the present invention have the advantages described above for the present molecules, yet without the specific binding activity of antibodies; however with a newly introduced specific binding activity in the structural loop or loop region.

Also for the antigen binding molecules according to the present invention it is preferred that the new antigen binding sites in the structural loops are introduced by randomizing technologies, i.e. by modifying one or more amino acid residues of at least two structural loops by randomization techniques or by introducing randomly generated inserts into such structural loops. Alternatively preferred is the use of combinatorial approaches.

According to another aspect, the present invention relates to a modified immunoglobulin having an antigen binding site foreign to the unmodified immunoglobulin and incorporated in one, two, three or more structural loops of the immunoglobulin or immunoglobulin variable domain. In this contact the term "foreign" means that the antigen binding site is not naturally formed by the specific structural loop or loop region of the variable immunoglobulin domain.

According to yet another aspect, the present invention relates to a modified immunoglobulin having an antigen binding site foreign to the unmodified immunoglobulin and incorporated in one, two, three or more structural loops of the variable domain, wherein said modified immunoglobulin binds to said antigen with an affinity of at least $10^3$ mol$^{-1}$, at least $10^4$ mol$^{-1}$, at least $10^5$ mol$^{-1}$, at least $10^6$ mol$^{-1}$, at least $10^7$ mol$^{-1}$, at least $10^8$ mol$^{-1}$, or at least $10^9$ mol$^{-1}$.

Usually binders with medium or high affinity are provided according to the invention. Those with medium affinity preferably exert a dissociation rate Kd in the range of $10^{-5}$ to $10^{-7}$, those with high affinity have a proven Kd in the range of $10^{-8}$ to $10^{-10}$, those having a Kd less than $10^{-9}$ being most preferred as a high affinity binder. In some cases it will be appropriate to select binders with even lower Kd, e.g. less than $10^{-11}$, usually as low as $10^{-12}$.

Preferred immunoglobulins or immunoglobulin variable domains according to the present invention comprise at least two antigen binding sites, the first site binding to a first epitope, and the second site binding to a second epitope.

According to a preferred embodiment, the present immunoglobulin or immunoglobulin variable domain comprises at least three loops or loop regions, the first loop or loop region binding to a first epitope, and the second and third loop or loop region binding to a second epitope. Either the at least first or at least second and third loop or loop region or both may contain a structural loop. The immunoglobulin or immunoglobulin variable domains according to the present inventions include the fragments thereof known in the art to be functional which contain the essential elements according to the present invention: the structural loops or loop regions modified according to the present invention.

Preferably, the immunoglobulin according to the present invention is composed of at least two immunoglobulin domains, or a part thereof including a minidomain, and each domain contains at least one antigen binding site. One of the preferred pairs of immunoglobulin domains is a CL/CH1 pair, which may be engineered in the structural loop region that is located at the C-terminus of the CL/CH1 pair. Thereby one or two new binding sites are engineered. Upon selection of the specific CL/CH1 binding domain pair, it may be recombined with the variable domains VL and VH to obtain a Fab molecule according to the invention with one "natural" binding site in the CDR region and one or two additional binding sites opposite thereto, i.e. in the C-terminal structural loop region of the CH1/CL domains.

Thus, the immunoglobulin according to the invention may be obtained by modifying an immunoglobulin parent molecule that contains the variable domain. Alternatively, a constant immunoglobulin domain may be engineered to obtain a binding site in the structural loop region, which domain can then be used as a building block to produce combinations with variable immunoglobulin domains and optionally with other constant domains, resulting in an immunoglobulin according to the invention that contains both a variable domain and a new binding site formed by structural loops or structural loop regions.

According to such preferred embodiment of the invention there is provided an immunoglobulin, which comprises at least one domain of the variable region of an immunoglobulin and at least one domain of the constant region of an immunoglobulin; for example, a variable domain, which is modified in at least two structural loops linked to a CH1 domain.

Another aspect of the present invention relates to a kit of binding partners containing (a) a polypeptide comprising a modified immunoglobulin variable domain having an antigen binding site incorporated in two or more structural loops, and (b) a binding molecule containing an epitope of said antigen.

Preferably a kit of binding partners according to the invention is containing (a) a library of modified immunoglobulins according to the present invention, and (b) a binding molecule containing an epitope of an antigen.

Such a binding molecule of this kit according to the present invention may be used for selecting and distinguishing a native or modified immunoglobulin according to the present invention in a sample or from a library. It may further be used for identifying the binding specificity of polypeptides comprising a modified immunoglobulin or immunoglobulin variable domain according to the present invention. By using the binding molecule of this kit according to the present invention, the potency of the modified polypeptide according to the present invention may be determined.

Potency as defined here is the binding property of the modified molecule of the invention to its antigen. The binding can be determined quantitatively and/or qualitatively in terms of specificity and/or affinity and/or avidity by assay methods as known in the art for quality control purposes.

Moreover, the binding molecule of a kit according to the present invention may be used for selecting the polypeptide comprising a modified immunoglobulin or immunoglobulin variable domain according to the present invention from a library as specified above, preferably consisting of at least 10, preferably at least 100, more preferably at least 1000, more preferred at least 10000, especially at least 100000 polypeptides with different modifications in the structural loops.

The present invention is further illustrated by the following examples.

Example 1

Design of the VHH Library

The crystal structure of the camel VHH domain D2-L24 in complex with Hen Egg White Lysozyme, which is published in the Brookhaven Database as entry 1ZVH.pdb was used to aid in the design of the mutated VHH domain. The sequence of chain A of the structure file 1ZVH.pdb is given in SEQ ID No. 1.

```
                                                SEQ ID No. 1
PREPQVYTLPPSRDELTKNQVSLTCLVKGFYPSDIAVEWESNGQPENNYKTTPPVLDSDGSFFL

YSKLTVDKSRWQQGNVFSCSVMHEALHNHYTQKSLSLSPGKAAA
```

The sequence which was used as the basis for construction of the VHH library is the sequence of the anti-TNF-alpha VHH domain from patent WO04041862A2[1], clone 3E and is given in SEQ ID No. 2.

```
                                     SEQ ID No. 2
ccatggcccc ccgagaacca caggtgtaca ccctgccccc atcccgtgac gagctcnnsn nsnnscaagt cagcctgacc tgcctggtca aaggcttcta tcccagcgac atcgccgtgg agtgggagag caatgggcagccggagaaca actacaagac cacgcctccc gtgctggact ccgacggctc cttcttcctc tacagcaagc ttaccgtgnn snnsnnsagg tggnnsnnsg ggaacgtctt ctcatgctcc gtgatgcatg aggctctgca caaccactac acacagaaga gcctctccct gtctccgggt aaagcggccg ca
```

After detailed analysis of the structure of 1ZVH.pdb and by visual inspection of the residues forming the loops which connect the beta strands, it was decided to randomize residues 13, 15, (i.e. in the loop between beta-strands A and B) 89, 90, 92 and 93 (i.e. in the loop between beta-strands E and F) of SEQ ID No. 2 for the generation of the library. In addition, three randomized positions were decided to be inserted between residues 14 and 15, and three randomized positions were decided to be inserted between residues 92 and 93 of SEQ ID No. 2.

Example 2

Construction of the VHH Library

The engineered gene coding for the VHH sequence is produced in the form of a synthetic gene by PCR assembly. The sequence and its translation are shown in FIG. 2. Amino acid residues to be randomized for library construction are underlined. Restriction sites for cloning are included as follows, and are underlined in the nucleotide sequence as shown in FIG. 2: NcoI, BglII and NotI.

The amino acid sequence encoded by the synthetic gene is given in SEQ ID. No.3.

```
                                                SEQ ID No. 3
MAPREPQVYTLPPSRDELXXXQVSLTCLVKGFYPSDIAVEWESNGQPENNYKTTPPVLDSDGSF

FLYSKLTVXXXRWXXGNVFSCSVMHEALHNHYTQKSLSLSPGKAAA
```

The first two residues and the last two residues are caused by the restriction sites used for cloning. The nucleotide sequence coding for SEQ ID No. 3 is given in SEQ ID No. 4.

```
SEQ ID No. 4:  cttgccatgg cccccgaga accacaggtg tac
```

The first two codons and the last two codons are caused by the restriction sites used for cloning.

The oligonucleotides for PCR assembly of the synthetic gene are designed by use of the publicly available software tool DNAWorks 3.1 (http://helixweb.nih.gov/dnaworks/) and are assembled by PCR following standard protocols from the 18 oligos presented in Table 1 and as SEQ ID No. 5 through SEQ ID No. 22 (Hoover D M, Lubkowski J., DNAWorks: an automated method for designing oligonucleotides for PCR-based gene synthesis, Nucleic Acids Res. 2002 May 15; 30(10):e43).

TABLE 1

Oligonucleotides used for assembly of the synthetic gene coding for the engineered VHH gene.

| | |
|---|---|
| 1. | CCATGGCAAGTTCAGCTGCAGGAAAGCGGTGGCGGCCTG (SEQ ID No. 5) |
| 2. | AGACGCAGGCTGCCGCCAGGCTGGACCAGGCCGCCACCGC (SEQ ID No. 6) |
| 3. | CGGCAGCCTGCGTCTGAGCTGTGCGGCCAGCGGCCGTACC (SEQ ID No. 7) |
| 4. | AGGTGTAGCCGCTATGGTCGCTAAAGGTACGGCCGCTGGC (SEQ ID No. 8) |

TABLE 1-continued

Oligonucleotides used for assembly of the synthetic gene coding for the engineered VHH gene.

5.  ACCATAGCGGCTACACCTATACCATTGGCTGGTTTCGTCA
    (SEQ ID No. 9)

6.  TCACGTTCTTTTCCTGGCGCCTGACGAAACCAGCCAATGG
    (SEQ ID No. 10)

7.  CGCCAGGAAAAGAACGTGAATTTGTGGCGCGTATTTACTG
    (SEQ ID No. 11)

8.  ATAGGTATTGCCGCTGCTCCAGTAAATACGCGCCACAAAT
    (SEQ ID No. 12)

9.  GAGCAGCGGCAATACCTATTATGCGGATAGCGTGAAAGGC
    (SEQ ID No. 13)

10. TGTCGCGGCTAATCGCGAAACGGCCTTTCACGCTATCCGC
    (SEQ ID No. 14)

11. GCGATTAGCCGGGACATTGCCAAGAACACGGTAGATCTTA
    (SEQ ID No. 15)

12. GGCTCCAGGTTGTTCATCGTAAGATCTACCGTGTTCTTGGC
    (SEQ ID No. 16)

13. CGATGAACAACCTGGAGCCCGAAGACACAGCCGTGTATTA
    (SEQ ID No. 17)

14. GCCATCCCGAGCCGCGCAATAATACACGGCTGTGTCTTCG
    (SEQ ID No. 18)

15. GCGGCTCGGGATGGCATTCCGACCAGCCGTAGCGTGGAAA
    (SEQ ID No. 19)

16. CCCTGGCCCCAGTAATTGTAGCTTTCCACGCTACGGCTGG
    (SEQ ID No. 20)

17. CAATTACTGGGGCCAGGGCACCCAGGTGACCGTCAGCTCT
    (SEQ ID No. 21)

18. GCGGCCGCAGAGCTGACGGTCACCTG
    (SEQ ID No. 22)

Briefly, equal volumes of oligonucleotide solutions (each at a concentration of ~1 mg/ml) are mixed together and diluted with water to a final concentration of ~1 ng/µl for each oligonucleotide. The oligonucleotide mixture is diluted 5-fold with the PCR solution. The final concentrations of components are 0.2 ng/µl for each oligonucleotide, 20 mM for Tris-HCl (pH 8.8), 10 mM for KCl, 10 mM for $(NH_4)_2SO_4$, 6 mM for $MgSO_4$, 0.1% (v/v) for Triton X-100, 0.1 mg/ml for bovine serum albumin, 0.2 mM for each dNTP and 2.5 U for Pfu polymerase. The PCR protocol for gene assembly begins with one 5 min denaturation step of 95° C., during which the polymerase is added to avoid any possible mispriming ('hot start' PCR). This step is followed by 25 cycles of a denaturation temperature of 95° C. for 30 s, an annealing temperature of 55° C. for 30 s and an extension temperature of 72° C. for 1.5 min. The last step in this protocol is an incubation cycle at 72° C. for 10 min. For gene amplification, 1 µl of the mixture resulting from the gene assembly reaction are used as the template, with the outermost oligonucleotides (SEQ ID No. 5 and SEQ ID No. 22) used as primers. The PCR protocol for gene amplification is essentially the same as that for gene assembly. The assembled synthetic VHH gene is subsequently cloned via the NcoI and NotI restriction sites in the vector pET27b (available under the trade name Novagen) and the sequence is verified by DNA sequencing.

PCR is then used to construct the randomized library. The template for the first 2 PCR reactions is the cloned synthetic VHH gene as described above. The primer pairs used for the first two PCR reactions are as follows: 3esynmu1 (gactccatgg caagtgcaac tgcaggaaag cggaggcggt ctggttnnsc cannsnnsnn snnsggcagc ctgcgtcga gct (SEQ ID No. 23)) and 3esynmu2 (catgagatct acggtgttct tggcg (SEQ ID No. 24)); 3esynmu3 (catgagatct tacgatgnns nnsttgnnsn nsnnsnnsnn sgaagatacg gcggtgtatt attg (SEQ ID No. 25)) and 3esyn2 (aatagcggcc gcagagctca cggtcacc (SEQ ID No. 26)). The resulting PCR products are digested with BglII, ligated, and the ligation product is used as template for a PCR reaction with primers 3esyn1 (acgtccatgg caagtgcaac tgcag (SEQ ID No. 27)) and 3esyn2 (aatagcggcc gcagagctca cggtcacc (SEQ ID No. 26)). The NNS codons in primers 3esynmu1 (SEQ ID No. 23) and 3esynmu3 (SEQ ID No. 25) introduce the randomized positions in the sequence. The codon NNS (IUPAC code, where S means C or G) is chosen which encodes all 20 naturally occurring amino acids, but avoids 2 out of 3 stop codons. FIG. 3 shows the schematic of the PCR reactions and ligation procedure. Horizontal arrows indicate the positions and directions of the PCR primers, vertical lines indicate the positions of the NcoI, BglII and NotI sites, respectively (from left to right).

This randomized PCR product is subsequently cloned into the phagemid cloning vector pHEN1 (Hoogenboom H R, Griffiths A D, Johnson K S, Chiswell D J, Hudson P, Winter G. Multi-subunit proteins on the surface of filamentous phage: methodologies for displaying antibody (Fab) heavy and light chains. Nucleic Acids Res. 1991 Aug. 11; 19(15):4133-7) in frame with the pelB secretion signal via the NcoI restriction site. The NotI restriction site at the 3' end of the gene inserts the VHH library in frame with the gene coding for the minor coat protein (protein III) of filamentous phage fd contained in the vector pHEN1. The engineered sequence of the randomized VHH library insert is given as a nucleotide sequence in SEQ ID No. 28 and translated as an amino acid sequence in SEQ ID No. 29. The Letter X in SEQ ID No. 29 denotes the randomized amino acid residues.

```
SEQ ID No. 28:
  1 ccatggcaag tgcaactgca ggaaagcgga ggcggtctgg ttnnsccann snnsnnsnns 61 ggcagcctgc gtctgagctg cgcggcgtcc ggccgtacct ttagcgacca ttcgggctat 121 acctatacca ttggctggtt ccgtcaggcg ccagggaaag aacgtgaatt tgtggcgcgt 181 atttactgga gcagcggcaa tacctactat gcggatagcg tgaaaggccg ttttgcgatt 241 agccgcgaca tcgccaagaa caccgtagat cttacgatgn nsnnsttgnn snnsnnsnns 301 nnsgaagata cggcggtgta ttattgcgca gcgcgtgacg gcattccgac ctcccgtagc 361 gtggaaagct acaattactg gggccagggc acccaggtga ccgtgagctc tgcggccgc
```

-continued

SEQ ID No. 29:
PWQVQLQESGGGLVXPXXXXGSLRLSCAASGRTFSDHSGYTYTIGWFRQAPGKEREFVARIYWSSGNTYYADSVKGR

FAISRDIAKNTVDLTMXXLXXXXXEDTAVYYCAARDGIPTSRSVESYNYWGQGTQVTVSSAA

The ligation product is then transformed into *Escherichia coli* TG1, the number of obtained colonies is determined, and a number of selected clones are controlled by restriction analysis and by DNA sequencing. For the following steps of the surface display library phage preparation, standard protocols are followed. Briefly, the ligation mixture is transformed into *E. coli* TG1 cells by electroporation. Subsequently, phage particles are rescued from *E. coli* TG1 cells with helper phage M13-KO7. Phage particles are then precipitated from culture supernatant with PEG/NaCl in 2 steps, dissolved in water and used for selection by panning or, alternatively, they are stored at minus 80° C.

Example 3

Panning of the VHH—Phage Library on Human Serum Albumin (HSA)

3 panning rounds are performed according to standard protocols. (e.g. Phage display of peptides and antibodies: a laboratory manual, Kay et al., 1996, Academic Press, San Diego, Calif.) Briefly, the following method is applied. Maxisorp 96-well plates (Nunc) are coated with HSA. 200 µl of the following solution are added per well: 0.1M Na-carbonate buffer, pH 9.6, with the following concentrations of HSA: $1^{st}$ panning round: 2 mg/ml HSA; 2nd panning round: 1 mg/ml HSA; $3^{rd}$ panning round: 1 mg/ml HSA Incubation is for 1 hour at 37° C., followed by blocking with 2% dry milk (M-PBS) with 200 µl per well for 1 hour at room temperature. The surface display phage library is then allowed to react with the bound HSA by adding 100 µl phage suspension and 100 µl 4% dry milk (M-PBS), followed by incubation for 45 minutes with shaking and for 90 minutes without shaking at room temperature.

Unbound phage particles are washed away as follows.

After the $1^{st}$ panning round: 10×300 µl T-PBS, 5×300 µl PBS; after the $2^{nd}$ panning round: 15×300 µl T-PBS, 10×300 µl PBS; after the $3^{rd}$ panning round: 20×300 µl T-PBS, 20×300 µl PBS.

Elution of bound phage particles is performed by adding 200 µl per well of 0.1 M glycine, pH 2.2, and incubation with shaking for 30 minutes at room temperature. Subsequently, the phage suspension is neutralized by addition of 60 µl 2M Tris-Base, followed by infection into *E. coli* TG1 cells by mixing 10 ml exponentially growing culture with 0.5 ml eluted phage and incubation for 30 minutes at 37° C. Finally, infected bacteria are plated on TYE medium with 1% glucose and 100 µg/ml ampicillin, and incubated at 30° C. overnight.

Example 4

Cloning of Selected Clones of VHH Mutants Selected Against HSA for Soluble Expression Phagemid DNA from the phage selected through the 3 panning rounds is isolated with a midi-prep. DNA encoding mutated VHH domains regions is batch-amplified by PCR and cloned NcoI-NotI into the vector pNOTBAD/Myc-His, which is the *E. coli* expression vector pBAD/Myc-His (Invitrogen) with an inserted NotI restriction site to facilitate cloning. Ligated constructs are transformed into *E. coli* LMG194 cells (Invitrogen) with electroporation, and grown at 30° C. on TYE medium with 1% glucose and ampicillin overnight. Selected clones are inoculated into 200 µl 2×YT medium with ampicillin, grown overnight at 30° C., and induced by adding L-arabinose to an end concentration of 0.1%. After expression at 16° C. overnight, the cells are harvested by centrifugation and treated with 100 µl Na-borate buffer, pH 8.0, at 4° C. overnight for preparation of periplasmic extracts. 50 µl of the periplasmic extracts are used in ELISA (see below).

Example 5

ELISA of VHH Mutants Selected Against HSA

The periplasmatic extracts of the VHH mutants selected for human serum albumin-binding are tested in an ELISA with the following protocol:

Coating: Microtiter plate (NUNC, Maxisorp), 100 µl per well, 100 µg HSA/ml in PBS, overnight at 4° C.
Wash: 3×200 µl PBS
Blocking: 1% Blocker Casein in PBS (Pierce), 1 h at RT
Wash: 3×200 µl PBS
Periplasmic extract binding: 50 µl periplasmic extract (Example 4), 50 µl PBS 0.05% Tween 20, at room temperature overnight
Wash: 3×200 µl PBS
$1^{st}$ antibody: anti-His4 (Qiagen), 1:1000 in PBS 0.05% Tween 20, 90 min at RT, 100 µl per well
Wash: 3×200 µl PBS
$2^{nd}$ antibody: goat anti mouse*HRP (SIGMA), 1:1000 in PBS 0.05% Tween 20, 90 min at RT (room temperature), 100 µl per well
Wash: 3×200 µl PBS
Detection: 3 mg/ml OPD in Na-citrate/phosphate buffer, pH 4.5, 0.4 µl 30% $H_2O_2$
Stopping before background gets too high: 100 ml 3M H2SO4
Absorbance read: 492/620 nm

Example 6

Example of a Library in which Only One Loop is Randomized: the C"D Loop

The synthetic gene coding for the engineered VHH gene described above in example 2 is used as a template for two PCR reactions in which the following primer pairs are used: SEQ ID No. 30 (actgctcgag agacatcgcc aagaacac; esynmu4) together with SEQ ID No. 26 (3esyn2) and SEQ ID No. 31 (cacactcgag atcgcaaasn nsnnsnncac snnsnncgca tagtaggtat tgcc; 3esynmu5) together with SEQ ID No. 27 (3esyn1). The resulting PCR products are digested with XhoI, ligated, and the ligation product is used as template for a PCR reaction with primers 3esyn1 (SEQ ID No. 27) and 3esyn2 (SEQ ID No. 26). The NNS codons in primers 3esynmu4 (SEQ ID No. 30) and 3esynmu5 (SEQ ID No. 31) introduce the randomized positions in the sequence similarity as described in example 2. FIG. 4 shows the schematic of the PCR reactions and ligation procedure. Horizontal arrows indicate the positions and directions of the PCR primers, vertical lines indicate the positions of the NcoI, XhoI and NotI sites, respectively (from left to right).

This randomized PCR product is subsequently cloned into the phagemid cloning vector pHEN1 (Hoogenboom H R, Griffiths A D, Johnson K S, Chiswell D J, Hudson P, Winter G. Multi-subunit proteins on the surface of filamentous phage: methodologies for displaying antibody (Fab) heavy and light chains. Nucleic Acids Res. 1991 Aug. 11; 19(15):4133-7) in frame with the pelB secretion signal and the minor coat protein (protein III) of filamentous phage fd contained in the vector pHEN1 as described in example 2. The engineered sequence of the randomized VHH library insert is given as a nucleotide sequence in SEQ ID No. 32 and translated as an amino acid sequence in SEQ ID No. 33. The Letter X in SEQ ID No. 33 denotes the randomized amino acid residues.

3 panning rounds are performed. Maxisorp 96-well plates (Nunc) are coated with hen egg lysozyme by adding 200 µl of the following solution per well:

PBS, with the following concentrations of dissolved hen egg lysozyme (HEL):
1st panning round: 2 mg/ml HEL
2nd panning round: 1 mg/ml HEL
3rd panning round: 1 mg/ml HEL
Incubation is for 1 hour at 37° C., followed by blocking with 2% dry milk (M-PBS) with 200 µl per well for 1 hour at room temperature.
The surface display phage library is then allowed to react with the bound hen egg lysozyme by adding 100 µl phage suspension and 100 µl 4% dry milk (M-PBS), followed by incubation for 45 minutes with shaking and for 90 minutes without shaking at room temperature.

```
                                                              SEQ ID No. 32
  1 ccatggcaag ttcagctgca ggaaagcggt ggcggcctgg tccagcctgg cggcagcctg 61 cgtctgagct gtgcggccag cggccgtacc tttagcgacc atagcggcta cacctatacc 121 attggctggt tcgtcaggc gccaggaaaa gaacgtgaat ttgtggcgcg tatttactgg 181 agcagcggca atacctatta tgcgnnsnns gtgnnsnnsn nsttcgcgat ctcgagagac 241 attgccaaga acacggtaga tcttacgatg aacaacctgg agcccgaaga cacagccgtg 301 tattattgcg cggctcggga tggcattccg accagccgta gcgtggaaag ctacaattac 361 tggggccagg gcacccaggt gaccgtcagc tctgcggccg c
```
```
                                                              SEQ ID No. 33
PWQVQLQESGGGLVQPGGSLRLSCAASGRTFSDHSGYTYTTGWFRQAPGKEREFVARIYWSSGNTYYAXXVXXX

FAISRDIAKNTVDLTMNNLEPEDTAVYYCAARDGIPTSRSVESYNYWGQGTQVTVSSAA
```

The ligation product is then transformed into *Escherichia coli* TG1, the number of obtained colonies is determined, and a number of selected clones are controlled by restriction analysis and by DNA sequencing. For the following steps of the surface display library phage preparation, standard protocols are followed as described in example 2. The steps of panning, selection and characterization of specifically binding clones are performed essentially as described in examples 3, 4 and 5.

Example 7

Example of a Library in which Three Loops are Randomized: the AB, the EF and the C"D Loop The library with randomized residues in the AB loop and in the EF loop as described in example 2 is used as a template for a PCR in which the same primer pairs as in example 6 are used: SEQ ID No. 30 (esynmu4) together with SEQ ID No. 26 (3esyn2) and SEQ ID No. 31 (3esynmu5) together with SEQ ID No. 27 (3esyn1). The following steps for library construction, cloning, panning, selection and characterization of specifically binding clones are essentially as described in examples 2, 3, 4 and 5.

Example 8

Comparison of Variable Domain Libraries with Randomized Amino Acid Positions in One, Two and Three Structural Loops The libraries are used in panning with various antigens.
hen-egg lysozyme as antigen:

Unbound phage particles were washed away as follows:
1st panning round: 10×300 µl T-PBS, 5×300 µl PBS
2nd panning round: 15×300 µl T-PBS, 10×300 µl PBS
3rd panning round: 20×300 µl T-PBS, 20×300 µl PBS
Elution of bound phage particles is performed by adding 200 µl per well of 0.1 M glycine, pH 2.2, and incubation with shaking for 30 minutes at room temperature. Subsequently, the phage suspension is neutralized by addition of 60 µl 2M Tris-Base, followed by infection into *E. coli* TG1 cells by mixture of 10 ml exponentially growing culture with 0.5 ml eluted phage and incubation for 30 minutes at 37° C. Finally, infected bacteria are plated on TYE medium with 1% glucose and 100 µg/ml Ampicillin, and incubated at 30° C. overnight.

Human serum albumin as antigen:

The libraries of examples 2, 6 and 7 are used in panning rounds as described above. Specifically, the phage libraries are suspended in binding buffer (PBS, 1% ovalbumin, 0.005% Tween 20) and panned against human serum albumin immobilized directly on maxisorp plates (10 micrograms/ml in PBS, overnight at 4° C.; plates are blocked with Blocker Casein (Pierce). After 2 hours, unbound phages are removed by repetitive washing (PBS, 0.05% Tween 20) and bound phage are eluted with 500 mM KCl, 10 mM HCl, pH2.

After each HSA-specific panning round the resulting clones are selected or tested for binding to TNF alpha. Selection and testing for TNF-alpha specificity is performed as described in example 1 of WO2004/041862.

FcRn as antigen:

The panning is performed as described in WO02060919, Example 6.2. In short, phage libraries are resuspended in 5 ml 20 mM MES, pH 6.0/5% skimmed milk/0.05% Tween 20 and added (100 micro-liter of 5×10¹² PFU/ml/well) to 20 wells of a Maxisorp immunoplate (Nunc) previously coated with 1 microgram of murine FcRn and blocked with 5% skimmed milk. After incubation for 2 h at 37° C., wells are washed 10-30 times with 20 mM MES, pH 6.0/0.2% Tween 20/0.3 M NaCl and phage eluted by incubation in 100 microliter PBS, pH 7.4/well for 30 min at 37° C. Phages are used to reinfect exponentially growing *E. coli* TG1, as described in example 3.

After each panning round on FcRn the resulting clones are selected or tested for binding to TNF alpha as described above.

Fc-gamma receptors as antigens:

Panning against recombinant fusion proteins of Fc-gammaRI, Fc-gammaRIIA and Fc-gammaRIIA are performed as described in Berntzen et al (2006) Protein Eng Des Sel 19:121-128 After each panning round on an Fc-receptor the resulting clones are selected or tested for binding to TNF alpha as described above.

Example 9

This example demonstrates the possibility to introduce new functions or additional binding specificities into an antibody fragment. The molecule used as a starting point for modification is the murine single chain antibody fragment sFv 26-10 (Huston et al. (1988) Proc Natl Acad Sci USA. 85:5879-5883). Five different libraries are constructed to modify different structural loop sequences by random amino acid sequences:

```
Library 26-10-1:
                                                       (SEQ ID NO. 34)
EVQLQQSGPELVKPGASVRMSCKSSGYIFTDFYMNWVRQSHGKSLDYIGYISPYSGVTGYNQKF

KGKATLTVDKSSSTAYMELRSLTSEDSAVYYCAGSSGNKWAMDYWGHGASVTVSSGGGGSGGGG

SGGGGSDVVMTQTPLSLPVSLGDQASISCRSSQSLVHSNGNTYLNWYLQKAGQSPKLLIYKVSN

RFSGXXXXFSGSGSGTDFTLKISXXXXXXXXGIYFCSQTTHVPPTFGGGTKLEIKR

Library 26-10-2:
                                                       (SEQ ID NO. 35)
EVQLQQSGPELVKPGASVRMSCKSSGYIFTDFYMNWVRQSHGKSLDYIGYISPYSGVTGYNQKF

KGKATLTVDKSSSTAYMELRSLTSEDSAVYYCAGSSGNKWAMDYWGHGASVTVSSGGGGSGGGG

SGGGGSDVVMTQTPLSLPXXXXXXQASISORSSQSLVHSNGNTYLNWYLQKAGQSPKLLIYKVSN

RFSGXXXXFSGSGSGTDFTLKISXXXXXXXXGIYFCSQTTHVPPTFGGGTKLEIKR

Library 26-10-3:
                                                       (SEQ ID NO. 36)
EVQLQQSGPELVKPGASVRMSCKSSGYIFTDFYMNWVRQSHGKSLDYIGYISPYSGVTGYNQKF

KGKATLTVDKSSSTAYMELRSLTSEDSAVYYCAGSSGNKWAMDYWGHGASVTVSSGGGGSGGGG

SGGGGSDVVMTQTPLSLPXXXXXXQASISCRSSQSLVHSNGNTYLNWYLQKAGQSPKLLIYKVSN

RFSGXVPDRFSGSGSGTDFTLKISXXXXXXXXGIYECSQTTHVPPTFGGGTKLEIKR

Library 26-10-4:
                                                       (SEQ ID NO. 37)
EVQLQQSGPELVKPGASVRMSCKSSCYIFTDFYMNWVRQSHGKSLDYIGYISPYSGVTGYNQKF

KGKATLTVDKSSSTAYMELRSLTSEDSAVYYCAGSSGNKWAMDYWGHGASVTVSSGGGGSGGGG

SGGGGSDVVMTQTPLSLPVSLGDQASISCRSSQSLVHSNGNTYLNWYLQKAGQSPKLLIYKVSN

RFSGXXXXXXXXFSGSGSGTDFTLKISXXXXXXXXGIYFCSQTTHVPPTFGGGTKLEIKR

Library 26-10-5:
                                                       (SEQ ID NO. 38)
EVQLQQSGPELVKPGASVRMSCKSSGYIFTDFYMNWVRQXXXXXXDYIGYISPYSGVTGYNQKF

KGKATLTVDKSSSTAYMELRSLTSEDSAVYYCAGSSGNKWAMDYWGHGASVTVSSGGGGSGGGG

SGGGGSDVVMTQTPLSLPVSLGDQASISCRSSQSLVHSNGNTYLNWYLQXXXXXXXKLLIYKVSN

RFSGVPDRFSGSGSGTDFTLKISRVEAEDLGIYFCSQTTHVPPTFGGGTKLEIKR

The libraries are produced by reverse translation of the
sequences, wherein the randomized amino acid positions are
encoded by the nucleotide triplet NNK.
Library 26-10-1 gene:
                                                       (SEQ ID NO. 39)
GAAGTTCAGCTGCAGCAGTCTGGTCCGGAACTGGTTAAACCGGGTGCTTCTGTTCGTATGTCTT

GCAAATCTTCTGGTTACATCTTCACCGACTTCTACATGAACTGGGTTCGTCAGTCTCACGGTAA

ATCTCTGGACTACATCGGTTACATCTCTCCGTACTCTGGTGTTACCGGTTACAACCAGAAATTC
```

-continued

AAAGGTAAAGCTACCCTGACCGTTGACAAATCTTCTTCTACCGCTTACATGGAACTGCGTTCTC

TGACCTCTGAAGACTCTGCTGTTTACTACTGCGCTGGTTCTTCTGGTAACAAATGGGCTATGGA

CTACTGGGGTCACGGTGCTTCTGTTACCGTTTCTTCTGGTGGTGGTGGTTCTGGTGGTGGTGGT

TCTGGTGGTGGTGGTTCTGACGTTGTTATGACCCAGACCCCGCTGTCTCTGCCGGTTTCTCTGG

GTGACCAGGCTTCTATCTCTTGCCGTTCTTCTCAGTCTCTGGTTCACTCTAACGGTAACACCTA

CCTGAACTGGTACCTGCAGAAAGCTGGTCAGTCTCCGAAACTGCTGATCTACAAAGTTTCTAAC

CGTTTCTCTGGTNNKNNKNNKNNKTTCTCTGGTTCTGGTTCTGGTACCGACTTCACCCTGAAAA

TCTCTNNKNNKNNKNNKNNKNNKGGTATCTACTTCTGCTCTCAGACCACCCACGTTCCGCC

GACCTTCGGTGGTGGTACCAAACTGGAAATCAAACGT

Library 26-10-2 gene:
(SEQ ID NO. 40)
GAAGTTCAGCTGCAGCAGTCTGGTCCGGAACTGGTTAAACCGGGTGCTTCTGTTCGTATGTCTT

GCAAATCTTCTGGTTACATCTTCACCGACTTCTACATGAACTGGGTTCGTCAGTCTCACGGTAA

ATCTCTGGACTACATCGGTTACATCTCTCCGTACTCTGGTGTTACCGGTTACAACCAGAAATTC

AAAGGTAAAGCTACCCTGACCGTTGACAAATCTTCTTCTACCGCTTACATGGAACTGCGTTCTC

TGACCTCTGAAGACTCTGCTGTTTACTACTGCGCTGGTTCTTCTGGTAACAAATGGGCTATGGA

CTACTGGGGTCACGGTGCTTCTGTTACCGTTTCTTCTGGTGGTGGTGGTTCTGGTGGTGGTGGT

TCTGGTGGTGGTGGTTCTGACGTTGTTATGACCCAGACCCCGCTGTCTCTGCCGNNKNNKNNKN

NKNNKCAGGCTTCTATCTCTTGCCGTTCTTCTCAGTCTCTGGTTCACTCTAACGGTAACACCTA

CCTGAACTGGTACCTGCAGAAAGCTGGTCAGTCTCCGAAACTGCTGATCTACAAAGTTTCTAAC

CGTTTCTCTGGTNNKNNKNNKNNKTTCTCTGGTTCTGGTTCTGGTACCGACTTCACCCTGAAAA

TCTCTNNKNNKNNKNNKNNKNNKGGTATCTACTTCTGCTCTCAGACCACCCACGTTCCGCC

GACCTTCGGTGGTGGTACCAAACTGGAAATCAAACGT

Library 26-10-3 gene:
(SEQ ID NO. 41)
GAAGTTCAGCTGCAGCAGTCTGGTCCGGAACTGGTTAAACCGGGTGCTTCTGTTCGTATGTCTT

GCAAATCTTCTGGTTACATCTTCACCGACTTCTACATGAACTGGGTTCGTCAGTCTCACGGTAA

ATCTCTGGACTACATCGGTTACATCTCTCCGTACTCTGGTGTTACCGGTTACAACCAGAAATTC

AAAGGTAAAGCTACCCTGACCGTTGACAAATCTTCTTCTACCGCTTACATGGAACTGCGTTCTC

TGACCTCTGAAGACTCTGCTGTTTACTACTGCGCTGGTTCTTCTGGTAACAAATGGGCTATGGA

CTACTGGGGTCACGGTGCTTCTGTTACCGTTTCTTCTGGTGGTGGTGGTTCTGGTGGTGGTGGT

TCTGGTGGTGGTGGTTCTGACGTTGTTATGACCCAGACCCCGCTGTCTCTGCCGNNKNNKNNKN

NKNNKCAGGCTTCTATCTCTTGCCGTTCTTCTCAGTCTCTGGTTCACTCTAACGGTAACACCTA

CCTGAACTGGTACCTGCAGAAAGCTGGTCAGTCTCCGAAACTGCTGATCTACAAAGTTTCTAAC

CGTTTCTCTGGTGTTCCGGACCGTTTCTCTGGTTCTGGTTCTGGTACCGACTTCACCCTGAAAA

TCTCTNNKNNKNNKNNKNNKNNKGGTATCTACTTCTGCTCTCAGACCACCCACGTTCCGCC

GACCTTCGGTGGTGGTACCAAACTGGAAATCAAACGT

Library 26-10-4 gene:
(SEQ ID NO. 42)
GAAGTTCAGCTGCAGCAGTCTGGTCCGGAACTGGTTAAACCGGGTGCTTCTGTTCGTATGTCTT

GCAAATCTTCTGGTTACATCTTCACCGACTTCTACATGAACTGGGTTCGTCAGTCTCACGGTAA

ATCTCTGGACTACATCGGTTACATCTCTCCGTACTCTGGTGTTACCGGTTACAACCAGAAATTC

AAAGGTAAAGCTACCCTGACCGTTGACAAATCTTCTTCTACCGCTTACATGGAACTGCGTTCTC

TGACCTCTGAAGACTCTGCTGTTTACTACTGCGCTGGTTCTTCTGGTAACAAATGGGCTATGGA

```
-continued
CTACTGGGGTCACGGTGCTTCTGTTACCGTTTCTTCTGGTGGTGGTGGTTCTGGTGGTGGTGGT

TCTGGTGGTGGTGGTTCTGACGTTGTTATGACCCAGACCCCGCTGTCTCTGCCGGTTTCTCTGG

GTGACCAGGCTTCTATCTCTTGCCGTTCTTCTCAGTCTCTGGTTCACTCTAACGGTAACACCTA

CCTGAACTGGTACCTGCAGAAAGCTGGTCACTCTCCGAAACTGCTGATCTACAAAGTTTCTAAC

CGTTTCTCTGGTNNKNNKNNKNNKNNKNNKNNKTTCTCTGGTTCTGGTTCTGGTACCGACTTCA

CCCTGAAAATCTCTNNKNNKNNKNNKNNKNNKNNKGGTATCTACTTCTGCTCTCAGACCACCCA

CGTTCCGCCGACCTTCGGTGGTGGTACCAAACTGGAAATCAAACGT

Library 26-10-5 gene:
                                                        (SEQ ID NO. 43)
GAAGTTCAGCTGCAGCAGTCTGGTCCGGAACTGGTTAAACCGGGTGCTTCTGTTCGTATGTCTT

GCAAATCTTCTGGTTACATCTTCACCGACTTCTACATGAACTGGGTTCGTCAGNNKNNKNNKNN

KNNKNNKGACTACATCGGTTACATCTCTCCGTACTCTGGTGTTACCGGTTACAACCAGAAATTC

AAAGGTAAAGCTACCCTGACCGTTGACAAATCTTCTTCTACCGCTTACATGGAACTGCGTTCTC

TGACCTCTGAAGACTCTGCTGTTTACTACTGCGCTGGTTCTTCTGGTAACAAATGGGCTATGGA

CTACTGGGGTCACGGTGCTTCTGTTACCGTTTCTTCTGGTGGTGGTGGTTCTGGTGGTGGTGGT

TCTGGTGGTGGTGGTTCTGACGTTGTTATGACCCAGACCCCGCTGTCTCTGCCGGTTTCTCTGG

GTGACCAGGCTTCTATCTCTTGCCGTTCTTCTCAGTCTCTGGTTCACTCTAACGGTAACACCTA

CCTGAACTGGTACCTGCAGNNKNNKNNKNNKNNKNNKAAACTGCTGATCTACAAAGTTTCTAAC

CGTTTCTCTGGTGTTCCGGACCGTTTCTCTGGTTCTGGTTCTGGTACCGACTTCACCCTGAAAA

TCTCTCGTGTTGAAGCTGAAGACCTGGGTATCTACTTCTGCTCTCAGACCACCCACGTTCCGCC

GACCTTCGGTGGTGGTACCAAACTGGAAATCAAACGT
```

The respective genes are assembled with chemically synthesized oligonucleotides and cloned in a phage display vector for phage surface display as described above with all necessary adaptions to achieve in-frame translation of a leader peptide, the sFv-variant and the coat protein III of the phage.

The phage displayed displayed libraries are selected for binding to human serum albumine, lysozyme, FcRn and Fc gamma receptors as described in example 8.

Alternatively the genes are ligated with the vector pRDV analog to the method described in Binz et al. (2005) Nat. Biotechnol. 22:575-582 and panned for human serum albumine, Fc-receptors and lysozyme according to the methodology described in Schaffitzel et al. (1999) J Immunol Methods 231:119-135.

Example 10

A human antibody, 2F5, specific for the HIV-peptide ELDKWA is used as a scaffold for randomization of structural loops and expressed as scFv. Expression and Phage display vector construction is performed as described in example 9. Phage selection is performed accordingly.

The wild type scFv sequence and the respective libraries are shown in FIGS. 5 to 8.

Example 11

Fab Library, in which Structural Loops of a Constant Domain are Randomized

For the selection of specifically binding molecules from libraries of immunoglobulin domains, in which residues that are located in structural loops have been randomized, various formats can be applied. Single domains, such as VL, VH, CH1, CH2, CH3, CH4 or CL domains can be used, Fc fragments which consist of CH2 and CH3 domains (including or not including the hinge region or parts thereof) can be used, Fv or single-chain Fv fragments can be used, whole antibodies can be used or other combinations of immunoglobulin domains can be used. One format that is of particular interest for the selection of specifically binding molecules is the Fab fragment, which is a heterodimer of two chains, namely the VL-CL part and the VH—CH1 part of the antibody. Fab fragments have been known for a long time, and can be produced by proteolytic cleavage of an IgG with the protease papain, and they can also be produced recombinantly in a wide range of different expression systems, such as for example *Escherichia coli, Saccharomyces cerevisiae, Pichia pastoris*, insect cells or mammalian cells.

It is well known in the art that surface display systems, such as phage display, yeast display, and other systems such as ribosome display etc. can be used for the enrichment and selection of specifically binding molecules such as Fab fragments from large libraries (See for example Hoogenboom H R, Griffiths A D, Johnson K S, Chiswell D J Hudson P, Winter G. Multi-subunit proteins on the surface of filamentous phage: methodologies for displaying antibody (Fab) heavy and light chains. Nucleic Acids Res. 1991 Aug. 11; 19(15): 4133-7.; Kang A S, Barbas C F, Janda K D, Benkovic S J, Lerner R A. Linkage of recognition and replication functions by assembling combinatorial antibody Fab libraries along phage surfaces. Proc Natl Acad Sci USA. 1991 May 15; 88(10):4363-6.; Kang X, Yang BA, Hu Y, Zhao H, Xiong W, Yang Y, Si B, Zhu Q. Human neutralizing Fab molecules against severe acute respiratory syndrome coronavirus generated by phage display. Clin Vaccine Immunol. 2006 August; 13(8):953-7.; Weaver-Feldhaus J M, Lou J, Coleman J R, Siegel R W, Marks J D, Feldhaus M J. Yeast mating for combinatorial Fab library generation and surface display. FEBS Lett. 2004 Apr. 23; 564(1-2):24-34.).

As an example, if the phage display system is applied for the display of Fab fragments (e.g. libraries of Fab fragments), one chain of the Fab fragment, e.g. the VH—CH1 chain, can be expressed as a fusion protein with e.g. protein III of phage M13, thereby leading to the display of this chain on the phage surface, while the other chain, VL-CL, is expressed in soluble form and forms the natural heterodimer with the surface anchored VH—CH1 chain. In a typical Fab surface display library, different VH and VL sequences are present, which can originate from a donor, typically a mouse or a human, but diversity can also be generated by in vitro methods such as site directed mutagenesis. Different binding sites are thereby generated, and by the use of a suitable display or other enrichment or selection method specifically binding clones can be isolated from such libraries that bind to their binding partner via the binding site that is formed by VH and VL.

Fab fragments can be generated that bind to one target via their natural binding site formed by VH and VL, and to another (or a second time to the same) target via binding sites formed by their structural loops. In order to obtain such engineered Fab fragments, libraries of Fabs are first generated in which residues in the structural loops are replaced by randomized sequences. Insertions of additional residues can also be made. Structural loops that can be engineered by this approach can be either C-terminal loops (the "bottom" loops) of VH or VL, or N-terminal ("top" loops) or C-terminal ("bottom" loops) of the CH1 or of the CL domains. Different combinations of domains with engineered structural loops at any of these positions are also possible. One format that can be used to select specifically binding domains is as single domains, as Fv or single-chain Fv fragments, or, as described in detail below, as Fab fragments.

The genes coding for VH—CH1 and VL-CL respectively of the antibody 4D5 (Cho H S, Mason K, Ramyar K X, Stanley A M, Gabelli S B, Denney D W Jr, Leahy D J. Structure of the extracellular region of HER2 alone and in complex with the Herceptin Fab. Nature. 2003 Feb. 13; 421 (6924):756-60.), which binds to human Her2 are used for this example. A synthetic gene is constructed which consists of the 4D5 VL-CL encoding part of the gene, flanked at its 5' end by an NcoI site for in-frame insertion in the pelB signal sequence contained in the phagemid vector pHEN1 (Hoogenboom H R, Griffiths A D, Johnson K S, Chiswell D J, Hudson P, Winter G. Multi-subunit proteins on the surface of filamentous phage: methodologies for displaying antibody (Fab) heavy and light chains. Nucleic Acids Res. 1991 Aug. 11; 19(15):4133-7) followed by a stop codon. At the transit of the sequence from VL into CL, a unique BsiWI restriction site is included, which is used later on for replacement of the wildtype CL sequence against library inserts containing randomized structural loops in combination with a unique AscI restriction site that is located downstream of the stop codon of the VL-CL encoding gene. It follows a sequence which contains a ribosome binding site (Shine-Dalgarno sequence) taken from Carter et al. (Carter P, Kelley R F, Rodrigues M L, Snedecor B, Covarrubias M, Velligan M D, Wong W L, Rowland A M, Kotts C E, Carver M E, et al. High level *Escherichia coli* expression and production of a bivalent humanized antibody fragment. Biotechnology (N Y). 1992 February; 10(2): 163-7), followed by a gene segment encoding the heat stable enterotoxin II (stII) signal sequence fused in frame to the VH—CH1 encoding part of the antibody 4D5 followed by a NotI site for in-frame insertion in the vector pHEN1. This dicistronic construct leads to the expression of VL-CL (the protein sequence of which is given in SEQ ID No. 44) on the one hand an on the other hand of VH—CH1 fused to protein III of phage M13 (the protein sequence of which is given in SEQ ID No. 45), which is encoded by pHEN1. The complete sequence of the 4D5 Fab display vector as described here is given as a nucleotide sequence in SEQ ID No. 46.

For construction of a library of CL domains in which residues in the structural loops are randomized, a synthetic gene is made which encodes a human kappa constant domain (CL) in which certain codons are replaced by a degenerated codon such as for example NNB (IUPAC code, where N stands for C, G, T and A; B stands for T, C and G). It is also possible to insert additional residues into the sequence. In this example, 3, 4 or 5 residues respectively are inserted between residues 127 and 128, and residues 182-185 and 187-189 are randomized (Kabat numbering). The sequences of the resulting genes are given as nucleotide sequences in SEQ ID No. 47, 48, and 49 (3, 4 or 5 insertions respectively between residues 127 and 128) and as amino acid sequences in SEQ ID No. 50, 51 and 52 (the letter X stands for any of the 20 naturally encoded amino acids). The nucleotide sequences include the BsiWI site on the 5' end and the AscI site at the 3' end for cloning into SEQ ID No. 46.

To construct the phage display library, the Fab 4D5 display vector (SEQ ID No. 46) is cleaved with the restriction enzymes BsiWI and AscI, and the large fragment is prepared by preparative agarose gel electrophoresis. The small fragment, corresponding to the gene encoding the wildtype CL is removed. The mixture of library inserts as described above (SEQ ID Nos. 47-49) and likewise cleaved with BsiWI and AscI and ligated to the purified vector fragment. The ligation mixture is transformed into a suitable *E. coli* strain such as TG1 by e.g. electroporation, and a large number of independent colonies are generated (e.g. 10exp8, 10exp9 or more). The transformed bacteria are pooled and infected with helper phage (such as e.g. M13K07) for rescue of phage particles. The phage particles are produced by standard procedures and used for panning of the library.

Panning of the library against a given target yields Fab fragments that not only bind to Her2 (due to binding site formed by VH and VL of the antibody 4D5) but also to the target against which they were selected.

In this example, the design, preparation and use of a Fab display library, in which structural loops of the CL domain are modified, is described. In an analogous way, libraries with randomization in the structural loops of other domains, such as the CH1, the VH or the VL domain can be prepared and used.

Sequences:

SEQ ID No. 44

```
              5         10        15        20        25        30
  1 M K Y L L P T A A A G L L L L A A Q P A M A D I Q M T Q S P

31 S S L S A S V G D R V T I T C R A S Q D V N T A V A W Y Q Q
```

```
 61 K P G K A P K L L I Y S A S F L Y S G V P S R F S G S R S G

91 T D F T L T I S S L Q P E D F A T Y Y C Q Q H Y T T P P T F

121 G Q G T K V E I K R T V A A P S V F I F P P S D E Q L K S G

151 T A S V V C L L N N F Y P R E A K V Q W K V D N A L Q S G N

181 S Q E S V T E Q D S K D S T Y S L S S T L T L S K A D Y E K

211 H K V Y A C E V T H Q G L S S P V T K S F N R G E C
///
```

SEQ ID No. 45
```
             5           10          15          20          25          30
  1 M K K N I A F L L A S M F V F S I A T N A Y A E V Q L V E S

31 G G G L V Q P G G S L R L S C A A S G F N I K D T Y I H W V

61 R Q A P G K G L E W V A R I Y P T N G Y T R Y A D S V K G R

91 F T I S A D T S K N T A Y L Q M N S L R A E D T A V Y Y C S

121 R W G G D G F Y A M D Y W G Q G T L V T V S S A S T K G P S

151 V F P L A P S S K S T S G G T A A L G C L V K D Y F P E P V

181 T V S W N S G A L T S G V H T F P A V L Q S S G L Y S L S S

211 V V T V P S S S L G T Q T Y I C N V N H K P S N T K V D K K

241 V E P K S C A A A E Q K L I S E E D L N G A A @ T V E S C L

271 A K P H T E N S F T N V W K D D K T L D R Y A N Y E G C L W

301 N A T G V V V C T G D E T Q C Y G T W V P I G L A I P E N E

331 G G G S E G G C S E G G G S E G G G T K P P E Y G D T P I P

361 G Y T Y I N P L D G T Y P P G T E Q N P A N P N P S L E E S

391 Q P L N T F M F Q N N F F R N R Q G A L T V Y T G T V T Q G

421 T D P V K T Y Y Q Y T P V S S K A M Y D A Y W N G K F R D C

451 A F H S G F N E D P F V C E Y Q G Q S S D L P Q P P V N A G

481 G G S G G G S G G G S E G G G S E G G G S E G G G S E G G G

511 S G G G S G S G D F D Y E K M A N A N K G A M T E N A D E N

541 A L Q S D A K G K L D S V A T D Y G A A I D G F I G D V S G

571 L A N G N A T G D F A G S N S Q M A Q V G D G D N S P L M

601 N N F R Q Y L P S L P Q S V E C R P Y V F G A G K P Y E F S

631 I D C D K I N L F R G V F A F L L Y V A T F M Y V F S T F A

661 N I L H K E S
```

SEQ ID No. 46
```
  1 gacgaaaggg cctcgtgata cgcctatttt tataggttaa tgtcatgata ataatggttt 61 cttagacgtc aggtggcact tttcggggaa atgtgcgcgg aacccctatt tgtttatttt 121 tctaaataca ttcaaatatg tatccgctca tgagacaata accctgataa atgcttcaat 181 aatattgaaa aaggaagagt atgagtattc aacatttccg tgtcgccctt attccctttt 241 ttgcggcatt tgccttcct gttttgctc acccagaaac gctggtgaaa gtaaaagatg 301 ctgaagatca gttgggtgca cgagtgggtt acatcgaact ggatctcaac agcggtaaga 361 tccttgagag ttttcgcccc gaagaacgtt ttccaatgat gagcactttt aaagttctgc 421 tatgtggcgc ggtattatcc cgtattgacg ccgggcaaga gcaactcggt cgccgcatac 481 actattctca gaatgacttg gttgagtact caccagtcac agaaaagcat cttacggatg
```

-continued

```
 541 gcatgacagt aagagaatta tgcagtgctg ccataaccat gagtgataac actgcggcca
 601 acttacttct gacaacgatc ggaggaccga aggagctaac cgcttttttg cacaacatgg
 661 gggatcatgt aactcgcctt gatcgttggg aaccggagct gaatgaagcc ataccaaacg
 721 acgagcgtga caccacgatg cctgtagcaa tggcaacaac gttgcgcaaa ctattaactg
 781 gcgaactact tactctagct tcccggcaac aattaataga ctggatggag gcggataaag
 841 ttgcaggacc acttctgcgc tcggcccttc cggctggctg gtttattgct gataaatctg
 901 gagccggtga gcgtgggtct cgcggtatca ttgcagcact ggggccagat ggtaagccct
 961 cccgtatcgt agttatctac acgacgggga gtcaggcaac tatggatgaa cgaaatagac
1021 agatcgctga gataggtgcc tcactgatta agcattggta actgtcagac caagtttact
1081 catatatact ttagattgat ttaaaacttc attttttaatt taaaaggatc taggtgaaga
1141 tcctttttga taatctcatg accaaaatcc cttaacgtga gttttcgttc cactgagcgt
1201 cagaccccgt agaaaagatc aaaggatctt cttgagatcc ttttttttctg cgcgtaatct
1261 gctgcttgca acaaaaaaa ccaccgctac cagcggtggt ttgtttgccg gatcaagagc
1321 taccaactct ttttccgaag gtaactggct tcagcagagc gcagatacca aatactgtcc
1381 ttctagtgta gccgtagtta ggccaccact tcaagaactc tgtagcaccg cctacatacc
1441 tcgctctgct aatcctgtta ccagtggctg ctgccagtgg cgataagtcg tgtcttaccg
1501 ggttggactc aagacgatag ttaccggata aggcgcagcg gtcgggctga acggggggtt
1561 cgtgcacaca gcccagcttg gagcgaacga cctacaccga actgagatac ctacagcgtg
1621 agcattgaga aagcgccacg cttcccgaag ggagaaaggc ggacaggtat ccggtaagcg
1681 gcagggtcgg aacaggagag cgcacgaggg agcttccagg gggaaacgcc tggtatcttt
1741 atagtcctgt cgggtttcgc cacctctgac ttgagcgtcg atttttgtga tgctcgtcag
1801 gggggcggag cctatggaaa aacgccagca acgcggcctt tttacggttc ctggccttttt
1861 gctggccttt tgctcacatg ttctttcctg cgttatcccc tgattctgtg ataaccgta
1921 ttaccgcctt tgagtgagct gataccgctc gccgcagccg aacgaccgag cgcagcgagt
1981 cagtgagcga ggaagcggaa gagcgcccaa tacgcaaacc gcctctcccc gcgcgttggc
2041 cgattcatta atgcagctgg cacgacaggt ttcccgactg gaaagcgggc agtgagcgca
2101 acgcaattaa tgtgagttag ctcactcatt aggcaccccca ggctttacac tttatgcttc
2161 cggctcgtat gttgtgtgga attgtgagcg ataacaatt tcacacagga aacagctatg
2221 accatgatta cgccaagctt gcatgcaaat tctatttcaa ggagacagtc ataatgaaat
2281 acctattgcc tacggcagcc gctggattgt tattactcgc ggcccagccg ccatggccg
2341 atatccagat gacccagtcc ccgagctccc tgtccgcctc tgtgggcgat agggtcacca
2401 tcacctgccg tgccagtcag gatgtgaata ctgctgtagc ctggtatcaa cagaaaccag
2461 gaaaagctcc gaaactactg atttactcgg catccttcct ctactctgga gtcccttctc
2521 gcttctctgg atccagatct gggacggatt tcactctgac catcagcagt ctgcagccgg
2581 aagacttcgc aacttattac tgtcagcaac attatactac tcctcccacg ttcggacagg
2641 gtaccaaggt ggagatcaaa cgtacggtgg cggcgccatc tgtcttcatc ttcccgccat
2701 ctgatgagca gcttaagtct ggaactgcct ctgttgtgtg cctgctgaat aacttctatc
2761 ccagagaggc caaagtacag tggaaggtgg ataacgccct ccaatcgggt aactcccagg
2821 agagtgtcac agagcaggac agcaaggaca gcacctacag cctcagcagc accctgacgc
2881 tgagcaaagc agactacgag aaacacaaag tctacgcctg cgaagtcacc catcagggcc
2941 tgagctcgcc cgtcacaaag agcttcaaca ggggagagtg ttaataaggc gcgccgctga
```

-continued

```
3001 tcctctacgc cggacgcatc gtggccctag tacgcaagtt cacgtaaaaa gggtatctag 3061 aggttgaggt gattttatga aaagaatat cgcatttctt cttgcatcta tgttcgtttt 3121 ttctattgct acaaatgcat acgctgaggt tcaactagtg gagtctggcg gtggcctggt 3181 gcagccaggg ggctcactcc gtttgtcctg tgcagcttct ggcttcaaca ttaaagacac 3241 ctatatacac tgggtgcgtc aggccccggg taagggcctg gaatggggttg caaggattta 3301 tcctacgaat ggttatacta gatatgccga tagcgtcaag ggccgtttca ctataagcgc 3361 agacacatcc aaaaacacag cctacctgca gatgaacagc ctgcgtgctg aggacactgc 3421 cgtctattat tgttctagat ggggagggga cggcttctat gctatggact actggggtca 3481 aggaaccctg gtcaccgtct cctcggcgtc gaccaagggc ccatcggtct tccccctggc 3541 accctcctcc aagagcacct ctgggggcac agcggccctg gctgcctgg tcaaggacta 3601 cttccccgaa ccggtgacgg tgtcgtgaa ctcaggtgcc ctgaccagcg gcgtgcacac 3661 cttcccggct gtcctacagt cctcaggact ctactccctc agcagcgtgg tgaccgtgcc 3721 ctccagcagc ttgggcaccc agacctacat ctgcaacgtg aatcacaagc ccagcaacac 3781 caaggtggac aagaaagttg agcccaaatc ttgtgcggcc gcagaacaaa aactcatctc 3841 agaagaggat ctgaatgggg ccgcatagac tgttgaaagt tgtttagcaa acctcatac 3901 agaaaattca tttactaacg tctggaaaga cgacaaaact ttagatcgtt acgctaacta 3961 tgagggctgt ctgtgaatg ctacaggcgt tgtggtttgt actggtgacg aaactcagtg 4021 ttacggtaca tgggttccta ttgggcttgc tatccctgaa aatgagggtg gtggctctga 4081 gggtggcggt tctgagggtg gcggttctga gggtggcggt actaaacctc ctgagtacgg 4141 tgatacacct attccgggct atacttatat caaccctctc gacggcactt atccgcctgg 4201 tactgagcaa aaccccgcta atcctaatcc ttctcttgag gagtctcagc ctcttaatac 4261 tttcatgttt cagaataata ggttccgaaa taggcagggt gcattaactg tttatacggg 4321 cactgttact caaggcactg acccccgtta aacttattac cagtacactc ctgtatcatc 4381 aaaagccatg tatgacgctt actggaacgg taaattcaga gactgcgctt tccattctgg 4441 ctttaatgag gatccattcg tttgtgaata tcaaggccaa tcgtctgacc tgcctcaacc 4501 tcctgtcaat gctggcggcg gctctggtgg tggttctggt ggcggctctg agggtggcgg 4561 ctctgagggt ggcggttctg agggtggcgg ctctgaggt ggcggttccg gtggcggctc 4621 cggttccggt gattttgatt atgaaaaaat ggcaaacgct aataaggggg ctatgaccga 4681 aaatgccgat gaaaacgcgc tacagtctga cgctaaaggc aaacttgatt ctgtcgctac 4741 tgattacggt gctgctatcg atggtttcat tggtgacgtt tccggccttg ctaatggtaa 4801 tggtgctact ggtgattttg ctggctctaa ttcccaaatg gctcaagtcg gtgacggtga 4861 taattcacct ttaatgaata atttccgtca atatttacct tctttgcctc agtcggttga 4921 atgtcgccct tatgtctttg gcgctggtaa accatatgaa ttttctattg attgtgacaa 4981 aataaactta ttccgtggtg tctttgcgtt ctttttatat gttgccacct ttatgtatgt 5041 attttcgacg tttgctaaca tactgcataa ggagtcttaa taagaattca ctggccgtcg 5101 ttttacaacg tcgtgactgg gaaaaccctg gcgttaccca acttaatcgc cttgcagcac 5161 atccccctt cgccagctgg cgtaatagcg aagaggcccg caccgatcgc ccttcccaac 5221 agttgcgcag cctgaatggc gaatggcgcc tgatgcggta ttttctcctt acgcatctgt 5281 gcggtatttc acaccgcacg tcaaagcaac catagtacgc gccctgtagc ggcgcattaa 5341 gcgcggcggg tgtggtggtt acgcgcagcg tgaccgctac acttgccagc gccctagcgc 5401 ccgctccttt cgctttcttc ccttcctttc tcgccacgtt cgccggcttt ccccgtcaag
```

-continued

```
5461 ctctaaatcg ggggctccct ttagggttcc gatttagtgc tttacggcac ctcgacccca
5521 aaaaacttga tttgggtgat ggttcacgta gtgggccatc gccctgatag acggttttc
5581 gcccttttgac gttggagtcc acgttcttta atagtggact cttgttccaa actggaacaa
5641 cactcaaccc tatctcgggc tattcttttg atttataagg gattttgccg atttcggcct
5701 attggttaaa aaatgagctg atttaacaaa aatttaacgc gaattttaac aaaatattaa
5761 cgtttacaat tttatggtgc actctcagta caatctgctc tgatgccgca tagttaagcc
5821 agccccgaca cccgccaaca cccgctgacg cgccctgacg ggcttgtctg ctcccggcat
5881 ccgcttacag acaagctgtg accgtctccg ggagctgcat gtgtcagagg ttttcaccgt
5941 catcaccgaa acgcgcga
```

SEQ ID No. 47
```
  1 cgtacggtgg cggcgccatc tgtcttcatc ttcccgccat ctgatgagca gcttaagtct
 61 nnbnnbnnbg gaactgcctc tgttgtgtgc ctgctgaata acttctatcc cagagaggcc
121 aaagtacagt ggaaggtgga taacgccctc caatcgggta actcccagga gagtgtcaca
181 gagcaggaca gcaaggacag cacctacagc ctcagcagca cctgacgct gnnbnnbnnb
241 nnbtacnnbn nbnnbaaagt ctacgcctgc gaagtcaccc atcagggcct gagctcgccc
301 gtcacaaaga gcttcaacag gggagagtgt taataaggcg cgcc
```

SEQ ID No. 48
```
  1 cgtacggtgg cggcgccatc tgtcttcatc ttcccgccat ctgatgagca gcttaagtct
 61 nnbnnbnnbn nbgaactgc ctctgttgtg tgcctgctga ataacttcta tcccagagag
121 gccaaagtac agtggaaggt ggataacgcc ctccaatcgg gtaactccca ggagagtgtc
181 acagagcagg acagcaagga cagcacctac agcctcagca gcaccctgac gctgnnbnnb
241 nnbnnbtacn nbnnbnnbaa agtctacgcc tgcgaagtca cccatcaggg cctgagctcg
301 cccgtcacaa agagcttcaa caggggagag tgttaataag gcgcgcc
```

SEQ ID No. 49
```
  1 cgtacggtgg cggcgccatc tgtcttcatc ttcccgccat ctgatgagca gcttaagtct
 61 nnbnnbnnbn nbnnbggaac tgcctctgtt gtgtgcctgc tgaataactt ctatcccaga
121 gaggccaaag tacagtggaa ggtggataac gccctccaat cgggtaactc ccaggagagt
181 gtcacagagc aggacagcaa ggacagcacc tacagcctca gcagcaccct gacgctgnnb
241 nnbnnbnnbt acnnbnnbnn baaagtctac gcctgcgaag tcacccatca gggcctgagc
301 tcgcccgtca caaagagctt caacagggga gagtgttaat aaggcgcgcc
```

SEQ ID No. 50
```
           5         10         15         20         25         30
  1 R T V A A P S V F I F P P S D E Q L K S X X X G T A S V V C
 31 L L N N F Y P R E A K V Q W K V D N A L Q S G N S Q E S V T
 61 E Q D S K D S T Y S L S S T L T L X X X X Y X X X K V Y A C
 91 E V T H Q G L S S P V T K S F N R G E C
```

SEQ ID No. 51
```
           5         10         15         20         25         30
  1 R T V A A P S V F I F P P S D E Q L K S X X X X G T A S V V
 31 C L L N N F Y P R E A K V Q W K V D N A L Q S G N S Q E S V
 61 T E Q D S K D S T Y S L S S T L T L X X X X Y X X X K V Y A
 91 C E V T H Q G L S S P V T K S F N R G E C
```

```
                      5              10             15             20             25            30    SEQ ID No. 52

1  R  T  V  A  A  P  S  V  F  I  F  P  P  S  D  E  Q  L  K  S  X  X  X  X  X  G  T  A  S  V

31  V  C  L  L  N  N  F  Y  P  R  E  A  K  V  Q  W  K  V  D  N  A  L  Q  S  G  N  S  Q  E  S

61  V  T  E  Q  D  S  K  D  S  T  Y  S  L  S  S  T  L  T  L  X  X  X  X  Y  X  X  X  K  V  Y

91  A  C  E  V  T  H  Q  G  L  S  S  P  V  T  K  S  F  N  R  G  E  C
```

DESCRIPTION OF FIGURES

FIG. 1: Sequence alignment of the amino acid sequences of SEQ ID No. 1 and SEQ ID No. 2.

FIG. 2: Nucleotide sequence encoding the synthetic gene coding for the anti-TNF-alpha camel VHH domain, as well as the translation in amino acid one-letter code. Restriction sites used for cloning are underlined in the nucleotide sequence. Amino acid residues to be randomized in the library are underlined in the amino acid sequence. (Inserted amino acids are not given in this sequence.)

FIG. 5: scFv 2F5 wt synthetic gene library 1 (VH-Linker-VL) and translation, with two structural loops randomized FIG. 6: scFv 2F5 wt synthetic gene library 2 (VH-Linker-VL) and translation, with two structural loops randomized FIG. 7: scFv 2F5 wt synthetic gene library 3 (VH-Linker-VL) and translation, with three structural loops randomized FIG. 8: scFv 2F5 wild-type synthetic gene with translation (VH-Linker-VL)

Figure 3:
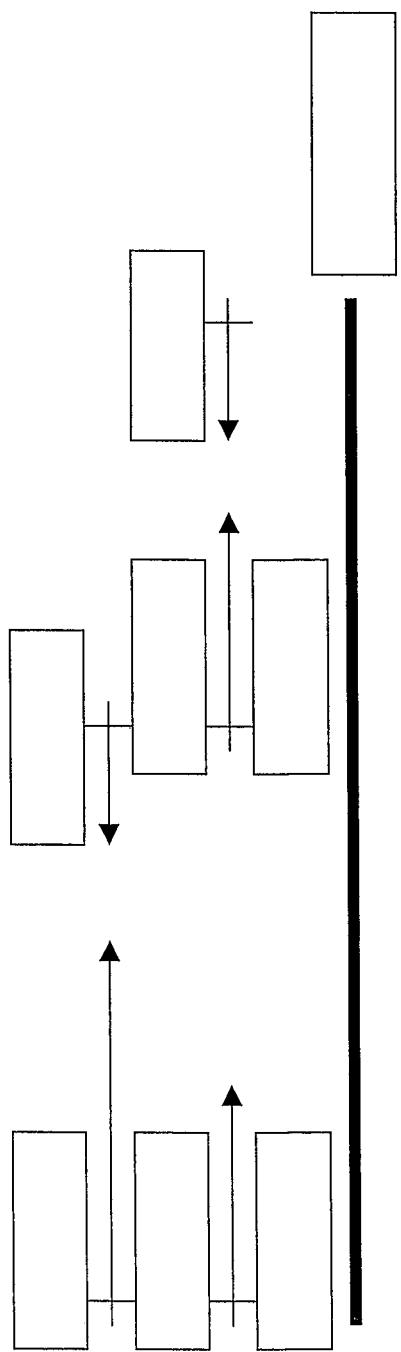
FIG. 3 shows the schematic of the PCR reactions and ligation procedure. Horizontal arrows indicate the positions and directions of the PCR primers, vertical lines indicate the positions of the NcoI, BglII and NotI sites, respectively (from left to right).
Figure 4:
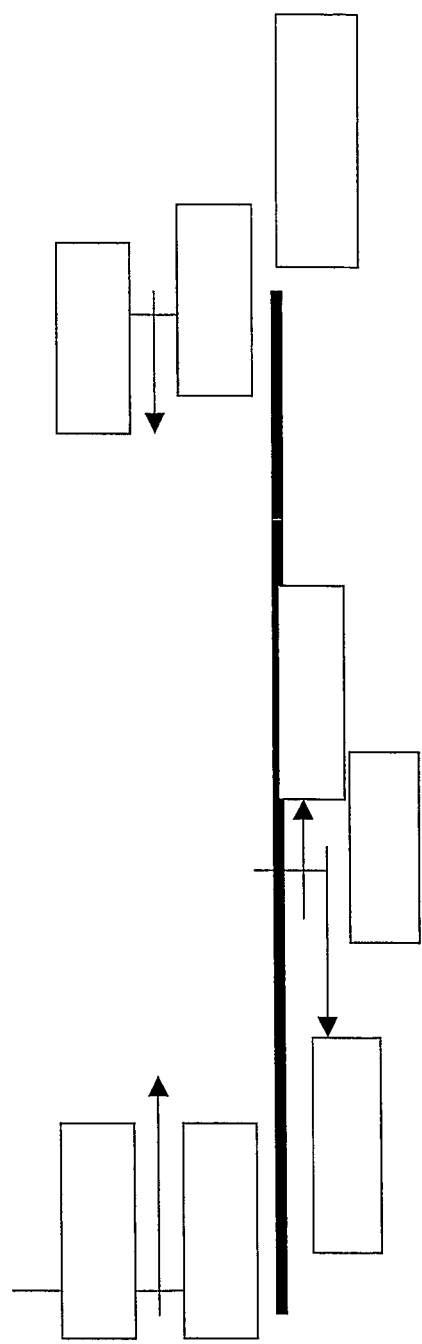
FIG. 4: Schematic of the PCR reactions used to construct the library as described in example 6.

```

The invention claimed is:

1. A method for providing a polypeptide or an antigen binding fragment thereof, comprising an antibody variable domain having a modified structural loop region, wherein the modified structural loop region contributes to a non-CDR antigen binding site that specifically binds to a first epitope, wherein the unmodified structural loop region does not specifically bind to said first epitope, comprising the steps of:
   (a) providing a nucleic acid encoding an immunoglobulin or fragment thereof, comprising at least two structural loops of an antibody variable domain having an antigen binding site comprising CDR loops, wherein said antigen binding site comprising said CDR loops specifically binds a second epitope,
   (b) performing a method of mutagenesis selected from the group consisting of random mutagenesis, semi-random mutagenesis and site-directed random mutagenesis of said structural loop, to modify at least three nucleotides of the nucleic acid of step (a), wherein the modification results in a substitution, deletion and/or insertion of three or more amino acids of said structural loops of the antibody variable domain of step (a),
wherein step (b) results in a structural loop region which comprises the at least one modified structural loop and which specifically binds to said first epitope, wherein said insertion does not comprise an insertion of a region selected from one or more of the group consisting of chimeric CDR-regions or CDR-like regions or canonical structures of CDR regions,
   (c) transferring said modified nucleic acid in an expression system,
   (d) expressing said modified immunoglobulin,
   (e) contacting the expressed modified immunoglobulin with an epitope, and
   (f) determining whether said modified immunoglobulin retains the CDR binding site and further binds to said first epitope.

2. The method according to claim 1, wherein said first epitope is different from said second epitope.

3. The method according to claim 1, wherein the immunoglobulin is of human, camelid or murine origin.

4. The method according to claim 1, wherein the antibody variable domain having a modified structural loop region is an antibody variable domain s selected from the group consisting of VH, Vkappa, Vlambda, VHH, a humanized Variable domain and combinations thereof.

5. The method according to claim 1, wherein the antibody variable domain having a modified structural loop region is an antibody variable domain selected from the group consisting of a VH, a Vkappa, a Vlambda or a VHH domain, wherein said variable domain comprises at least one modification within amino acids 7 to 21, amino acids 25 to 39, amino acids 41 to 81, amino acids 83 to 85, amino acids 89 to 103, or amino acids 106 to 117, where the numbering of the amino acid positions of the antibody variable domain is that of the IMGT.

6. The method according to claim 1, wherein the antibody variable domain having a modified structural loop region is an antibody variable domain of human origin selected from the group consisting of a VH, Vkappa and a Vlambda of human origin, and wherein said variable domain comprises at least one modification within amino acids 8 to 20, amino acids 44 to 50, amino acids 67 to 76, and amino acids 89 to 101, where the numbering of the amino acid position of the domains is that of the IMGT.

7. The method according to claim 1, wherein the antibody variable domain having a modified structural loop region is an antibody variable domain of murine origin, and wherein said variable domain comprises at least one modification within amino acids 6 to 20, amino acids 44 to 52, amino acids 67 to 76, and amino acids 92 to 101, where the numbering of the amino acid positions of the domain is that of the IMGT.

8. The method according to claim 1, wherein the antibody variable domain having a modified structural loop region is an antibody variable domain of camelid origin and comprises at least one modification within amino acids 7 to 18, amino acids 43 to 55, amino acids 68 to 75, and amino acids 91 to 101, where the numbering of the amino acid position of the domains is that of the IMGT.

9. The method according to claim 1, wherein the modified immunoglobulin or fragment thereof is further combined with one or more modified immunoglobulins or fragments thereof, or with unmodified immunoglobulins, or fragments thereof, to obtain a combination immunoglobulin.

10. The method according to claim 1, wherein in step (b), the modification is generated by site-directed random mutation of at least one nucleic acid.

11. The method according to claim 10, characterised in that the nucleic acid comprises at least one nucleotide repeating unit having the sequence 5'-NNS-3', 5'-NNN-3' or 5'-NNK-3'.

12. A method for engineering an immunoglobulin comprising a modified structural loop region, the modified structural loop region comprising a non-CDR binding site that specifically binds to a first epitope of an antigen, wherein the unmodified structural loop region does not significantly bind to said first epitope, comprising the steps of:
   (a) providing a nucleic acid encoding an immunoglobulin comprising at least two structural loops and an antibody variable domain having a CDR binding site for binding a second epitope,
   (b) performing a method of mutagenesis selected from the group consisting of random mutagenesis, semi-random mutagenesis and site-directed random mutagenesis of said structural loop, to modify at least three nucleotides of the nucleic acid of step (a), wherein the modification results in a substitution of three or more amino acids of said structural loops at positions selected from the group consisting of positions 13, 15, 89, 90, 92, and 93, according to the IMGT numbering system, of the antibody variable domain of step (a), wherein said modification does not comprise an insertion of a region selected from one or more of the group consisting of chimeric CDR-regions or CDR-like regions or canonical structures of CDR regions,
   (c) transferring said modified nucleic acid in an expression system,
   (d) expressing said modified immunoglobulin, (e) contacting the expressed modified immunoglobulin with an epitope, and (f) determining whether said modified immunoglobulin retains the CDR binding site and further binds to said first epitope.

13. The method of claim 1, wherein in step (b), the modification is generated by introducing a synthetic oligonucleotide into a larger segment of said nucleic acid.

14. The method according to claim 6, wherein said variable domain comprises at least one modification within amino acid positions 12 to 17, amino acid positions 45 to 50, amino acid positions 69 to 75 and amino acid positions 93 to 98 according to the IMGT numbering system.

15. The method of claim 1, wherein said modified nucleic acid of step (b) is solubly expressed in a prokaryote or eukaryote expression system.

16. The method of claim 1, wherein said expression system is a display system.

17. The method of claim 16, wherein said display system is selected from the group consisting of a cell surface display system, a viral display system, a mRNA display system, a polysomal display system and a ribosomal display system.

18. The method of claim 17, wherein said cell surface display system is selected from the group consisting of a yeast cell display system, a bacterial cell display system, and a mammalian cell display system.

19. The method of claim 17, wherein said viral display system is a phage display system.

20. The method of claim 1, wherein said modified nucleic acid of step (b) is expressed in an in vitro display system.

21. The method of claim 1, wherein said modified nucleic acid of step (b) is expressed with a fusion partner that binds to a specific sequence on the expression vector, thus linking covalently or noncovalently the fusion partner and associated expressed modified nucleic acid of step (b) with the nucleic acid that encodes them.

22. The method of claim 1, wherein the expression system comprises a library displaying or encoding said modified nucleic acid of step (b).

23. The method of claim 1, wherein step (d) comprises expressing said modified nucleic acid of step (b) as an immunoglobulin or fragment thereof.

24. The method of claim 23, wherein step (e) comprises contacting the expressed modified immunoglobulin or fragment thereof, with an antigen comprising said first epitope.

25. The method of the claim 24, wherein step (f) comprises determining whether the expressed modified immunoglobulin or fragment thereof specifically binds to said second epitope.

26. The method of claim 1, wherein the modification of step (b) results in a substitution, deletion and/or insertion of one or more amino acids of at least two of said structural loops of the antibody variable domain of step (a).

27. The method of claim 1, wherein the modification of step (b) results in a substitution, deletion and/or insertion of one or more amino acids of at least three of said structural loops of the antibody variable domain of step (a).

28. The method of claim 1, wherein the modification of step (b) results in a substitution, deletion and/or insertion of one or more amino acids of at least four of said structural loops of the antibody variable domain of step (a).

29. The method of claim 4, further comprising modifying a structural loop region of said a constant domain of said polypeptide or an antigen binding fragment thereof, wherein said modified structural loop region of said constant domain specifically binds a third epitope.

30. The method of claim 1, wherein said first epitope is present on an antigen selected from the group consisting of: TNF, Fcγ1, CD23, TCR, RANKL, cMet, reactive oxygen modified Collagen II, VEGF, CD89, CD20, CD3, EGFR, Her2 and Lewis Y.

31. The method of claim 1, wherein the second epitope is present on an antigen selected from the group consisting of: TNF, FcγR1, CD23, TCR, RANKL, cMet, reactive oxygen modified Collagen II, VEGF, CD89, CD20, CD3, EGFR, Her2 and Lewis Y.

32. The method of claim 29, where the third epitope is present on an antigen selected from the group consisting of: TNF, FcER1, CD23, TCR, VEGF, RANKL, cMet, reactive oxygen modified Collagen II, CD89, CD20, CD3, EGFR, Her2 and Lewis Y.

33. The method of claim 29, where the third epitope is identical to said first epitope and/or said second epitope.

34. The method of claim 1 wherein said first epitope identical to said second epitope.

35. The method of claim 1, wherein said polypeptide is a complete antibody molecule, or an antigen binding fragment thereof.

36. The method of claim 35, wherein said antigen binding fragment is selected from the group consisting of Fab, Fab2, scFv, Fv, dAb, minibody, Fd, VL, VH, VHH and a minidomain consisting of two beta-strands of an immunoglobulin domain connected by at least two structural loops.

37. The method of claim 35, wherein the antibody molecule is selected from the group consisting of IgG, IgA, IgM, IgD and IgE.

38. The method of claim 35, wherein the complete antibody molecule is a bi-specific, full-length antibody.

* * * * *

SEQUENCE LISTING

<160> NUMBER OF SEQ ID NOS: 62

<210> SEQ ID NO 1
<211> LENGTH: 108
<212> TYPE: PRT
<213> ORGANISM: Camelus sp.

<400> SEQUENCE: 1

Pro Arg Glu Pro Gln Val Tyr Thr Leu Pro Pro Ser Arg Asp Glu Leu
 1               5                  10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys Ala Ala Ala
            100                 105

<210> SEQ ID NO 2
<211> LENGTH: 332
<212> TYPE: DNA
<213> ORGANISM: artificial sequence
<220> FEATURE:
<223> OTHER INFORMATION: sequence of the anti-TNF-alpha VHH domain
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
```

```
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (237)..(238)
<223> OTHER INFORMATION: n is a, c, g, or t

<400> SEQUENCE: 2
ccatggcccc ccgagaacca caggtgtaca ccctgccccc atcccgtgac gagctcnnsn      60
nsnnscaagt cagcctgacc tgcctggtca aaggcttcta tcccagcgac atcgccgtgg     120
agtgggagag caatgggcag ccggagaaca actacaagac cacgcctccc gtgctggact     180
ccgacggctc cttcttcctc tacagcaagc ttaccgtgnn snnsnnsagg tggnnsnnsg     240
ggaacgtctt ctcatgctcc gtgatgcatg aggctctgca caaccactac acacagaaga     300
gcctctccct gtctccgggt aaagcggccg ca                                   332

<210> SEQ ID NO 3
<211> LENGTH: 110
<212> TYPE: PRT
<213> ORGANISM: artificial sequence
<220> FEATURE:
<223> OTHER INFORMATION: VHH sequence
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid

<400> SEQUENCE: 3

Met Ala Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Xaa Xaa Xaa Arg Trp Xaa Xaa Gly
65                  70                  75                  80
```

Asn Val Phe Ser Cys Ser Val Met His Glu Ala Leu His Asn His Tyr
            85                  90                  95

Thr Gln Lys Ser Leu Ser Leu Ser Pro Gly Lys Ala Ala Ala
            100                 105                 110

<210> SEQ ID NO 4
<211> LENGTH: 33
<212> TYPE: DNA
<213> ORGANISM: artificial sequence
<220> FEATURE:
<223> OTHER INFORMATION: nucleotide sequence coding for SEQ ID NO:3

<400> SEQUENCE: 4
cttgccatgg cccccccgaga accacaggtg tac                               33

<210> SEQ ID NO 5
<211> LENGTH: 39
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 5
ccatggcaag ttcagctgca ggaaagcggt ggcggcctg                          39

<210> SEQ ID NO 6
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 6
agacgcaggc tgccgccagg ctggaccagg ccgccaccgc                         40

<210> SEQ ID NO 7
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 7
cggcagcctg cgtctgagct gtgcggccag cggccgtacc                         40

<210> SEQ ID NO 8
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 8
aggtgtagcc gctatggtcg ctaaaggtac ggccgctggc                         40

<210> SEQ ID NO 9
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 9
accatagcgg ctacacctat accattggct ggtttcgtca                                40

<210> SEQ ID NO 10
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 10
tcacgttctt ttcctggcgc ctgacgaaac cagccaatgg                                40

<210> SEQ ID NO 11
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 11
cgccaggaaa agaacgtgaa tttgtggcgc gtatttactg                                40

<210> SEQ ID NO 12
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 12
ataggtattg ccgctgctcc agtaaatacg cgccacaaat                                40

<210> SEQ ID NO 13
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 13
gagcagcggc aatacctatt atgcggatag cgtgaaaggc                                40

<210> SEQ ID NO 14
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 14
tgtcgcggct aatcgcgaaa cggcctttca cgctatccgc                                40

<210> SEQ ID NO 15
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 15
gcgattagcc gcgacattgc caagaacacg gtagatctta                                40

<210> SEQ ID NO 16
<211> LENGTH: 41
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 16
ggctccaggt tgttcatcgt aagatctacc gtgttcttgg c                              41

<210> SEQ ID NO 17
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 17
cgatgaacaa cctggagccc gaagacacag ccgtgtatta                                40

<210> SEQ ID NO 18
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 18
gccatcccga gccgcgcaat aatacacggc tgtgtcttcg                                40

<210> SEQ ID NO 19
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 19
gcggctcggg atggcattcc gaccagccgt agcgtggaaa                                40

<210> SEQ ID NO 20
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 20
ccctggcccc agtaattgta gctttccacg ctacggctgg                                40

<210> SEQ ID NO 21
<211> LENGTH: 40
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 21
caattactgg ggccagggca cccaggtgac cgtcagctct                                40

<210> SEQ ID NO 22
<211> LENGTH: 26
<212> TYPE: DNA
<213> ORGANISM: artificial sequence
<220> FEATURE:
<223> OTHER INFORMATION: oligonucleotide for PCR assembly of the
      synthetic gene coding for engineered VHH sequence

<400> SEQUENCE: 22
gcggccgcag agctgacggt cacctg                                              26

<210> SEQ ID NO 23
<211> LENGTH: 83
<212> TYPE: DNA
<213> ORGANISM: artificial sequence
<220> FEATURE:
<223> OTHER INFORMATION: PCR primer 3esynmu1
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t

<400> SEQUENCE: 23
gactccatgg caagtgcaac tgcaggaaag cggaggcggt ctggttnnsc cannsnnsnn         60
snnsggcagc ctgcgtctga gct                                                 83

<210> SEQ ID NO 24
<211> LENGTH: 25
<212> TYPE: DNA
<213> ORGANISM: artificial sequence
<220> FEATURE:
<223> OTHER INFORMATION: PCR primer 3esynmu2

<400> SEQUENCE: 24
catgagatct acggtgttct tggcg                                               25

<210> SEQ ID NO 25
<211> LENGTH: 64
<212> TYPE: DNA
<213> ORGANISM: artificial sequence
<220> FEATURE:
<223> OTHER INFORMATION: PCR primer 3esynmu3
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t

```
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 25
catgagatct tacgatgnns nnsttgnnsn nsnnsnnsnn sgaagatacg gcggtgtatt      60
attg                                                                  64

<210> SEQ ID NO 26
<211> LENGTH: 28
<212> TYPE: DNA
<213> ORGANISM: artificial sequence
<220> FEATURE:
<223> OTHER INFORMATION: PCR primer 3esyn2

<400> SEQUENCE: 26
aatagcggcc gcagagctca cggtcacc                                        28

<210> SEQ ID NO 27
<211> LENGTH: 25
<212> TYPE: DNA
<213> ORGANISM: artificial sequence
<220> FEATURE:
<223> OTHER INFORMATION: PCR primer 3esyn1

<400> SEQUENCE: 27
acgtccatgg caagtgcaac tgcag                                           25

<210> SEQ ID NO 28
<211> LENGTH: 419
<212> TYPE: DNA
<213> ORGANISM: artificial sequence
<220> FEATURE:
<223> OTHER INFORMATION: engineered sequence of the randomized VHH
      library insert
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
```

```
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t
<220> FEATURE:
<221> NAME/KEY: misc_feature
<222> LOCATION: (298)..(299)
<223> OTHER INFORMATION: n is a, c, g, or t
<220> FEATURE:
<221> NAME/KEY: misc_feature
<222> LOCATION: (301)..(302)
<223> OTHER INFORMATION: n is a, c, g, or t

<400> SEQUENCE: 28
ccatggcaag tgcaactgca ggaaagcgga ggcggtctgg ttnnsccann snnsnnsnns      60
ggcagcctgc gtctgagctg cgcggcgtcc ggccgtacct ttagcgacca ttcgggctat     120
acctatacca ttggctggtt ccgtcaggcg ccagggaaag aacgtgaatt tgtggcgcgt     180
atttactgga gcagcggcaa tacctactat gcggatagcg tgaaaggccg ttttgcgatt     240
agccgcgaca tcgccaagaa caccgtagat cttacgatgn nsnnsttgnn snnsnnsnns     300
nnsgaagata cggcggtgta ttattgcgca gcgcgtgacg gcattccgac ctcccgtagc     360
gtggaaagct acaattactg gggccagggc acccaggtga ccgtgagctc tgcggccgc     419

<210> SEQ ID NO 29
<211> LENGTH: 139
<212> TYPE: PRT
<213> ORGANISM: artificial sequence
<220> FEATURE:
<223> OTHER INFORMATION: amino acid sequence translation of SEQ ID NO:28
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (94)..(95)
<223> OTHER INFORMATION: Xaa can be any naturally occurring amino acid
<220> FEATURE:
<221> NAME/KEY: misc_feature
<222> LOCATION: (97)..(101)
<223> OTHER INFORMATION: Xaa can be any naturally occurring amino acid

<400> SEQUENCE: 29

Pro Trp Gln Val Gln Leu Gln Glu Ser Gly Gly Gly Leu Val Xaa Pro
 1               5                  10                  15

Xaa Xaa Xaa Xaa Gly Ser Leu Arg Leu Ser Cys Ala Ala Ser Gly Arg
            20                  25                  30

Thr Phe Ser Asp His Ser Gly Tyr Thr Tyr Thr Ile Gly Trp Phe Arg
        35                  40                  45
```

```
Gln Ala Pro Gly Lys Glu Arg Glu Phe Val Ala Arg Ile Tyr Trp Ser
    50                  55                  60
Ser Gly Asn Thr Tyr Tyr Ala Asp Ser Val Lys Gly Arg Phe Ala Ile
 65                 70                  75                  80
Ser Arg Asp Ile Ala Lys Asn Thr Val Asp Leu Thr Met Xaa Xaa Leu
                85                  90                  95
Xaa Xaa Xaa Xaa Xaa Glu Asp Thr Ala Val Tyr Tyr Cys Ala Ala Arg
            100                 105                 110
Asp Gly Ile Pro Thr Ser Arg Ser Val Glu Ser Tyr Asn Tyr Trp Gly
        115                 120                 125
Gln Gly Thr Gln Val Thr Val Ser Ser Ala Ala
    130                 135
```

```
<210> SEQ ID NO 30
<211> LENGTH: 28
<212> TYPE: DNA
<213> ORGANISM: artificial sequence
<220> FEATURE:
<223> OTHER INFORMATION: PCR primer esynmu4

<400> SEQUENCE: 30
actgctcgag agacatcgcc aagaacac                                        28

<210> SEQ ID NO 31
<211> LENGTH: 54
<212> TYPE: DNA
<213> ORGANISM: artificial sequence
<220> FEATURE:
<223> OTHER INFORMATION: PCR primer 3esynmu5
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 31
cacactcgag atcgcaaasn nsnnsnncac snnsnncgca tagtaggtat tgcc           54

<210> SEQ ID NO 32
<211> LENGTH: 401
<212> TYPE: DNA
<213> ORGANISM: artificial sequence
<220> FEATURE:
<223> OTHER INFORMATION: engineered sequence of the randomized VHH
      library insert
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (208)..(209)
<223> OTHER INFORMATION: n is a, c, g, or t
```

<220> FEATURE:
<221> NAME/KEY: misc_feature
<222> LOCATION: (214)..(215)
<223> OTHER INFORMATION: n is a, c, g, or t
<220> FEATURE:
<221> NAME/KEY: misc_feature
<222> LOCATION: (217)..(218)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t

<400> SEQUENCE: 32

```
ccatggcaag ttcagctgca ggaaagcggt ggcggcctgg tccagcctgg cggcagcctg      60
cgtctgagct gtgcggccag cggccgtacc tttagcgacc atagcggcta cacctatacc     120
attggctggt tcgtcaggc gccaggaaaa gaacgtgaat tgtgtggcgcg tatttactgg     180
agcagcggca ataccctatta tgcgnnsnns gtgnnsnnsn nsttcgcgat ctcgagagac     240
attgccaaga acacggtaga tcttacgatg aacaacctgg agcccgaaga cacagccgtg     300
tattattgcg cggctcggga tggcattccg accagccgta gcgtggaaag ctacaattac     360
tggggccagg gcacccaggt gaccgtcagc tctgcggccg c                         401
```

<210> SEQ ID NO 33
<211> LENGTH: 133
<212> TYPE: PRT
<213> ORGANISM: artificial sequence
<220> FEATURE:
<223> OTHER INFORMATION: amino acid sequence translation of SEQ ID NO:32
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (72)..(74)
<223> OTHER INFORMATION: Xaa can be any naturally occurring amino acid

<400> SEQUENCE: 33

Pro Trp Gln Val Gln Leu Gln Glu Ser Gly Gly Gly Leu Val Gln Pro
1               5                   10                  15

Gly Gly Ser Leu Arg Leu Ser Cys Ala Ala Ser Gly Arg Thr Phe Ser
            20                  25                  30

Asp His Ser Gly Tyr Thr Tyr Thr Ile Gly Trp Phe Arg Gln Ala Pro
        35                  40                  45

Gly Lys Glu Arg Glu Phe Val Ala Arg Ile Tyr Trp Ser Ser Gly Asn
    50                  55                  60

Thr Tyr Tyr Ala Xaa Xaa Val Xaa Xaa Xaa Phe Ala Ile Ser Arg Asp
65                  70                  75                  80

Ile Ala Lys Asn Thr Val Asp Leu Thr Met Asn Asn Leu Glu Pro Glu
            85                  90                  95

Asp Thr Ala Val Tyr Tyr Cys Ala Ala Arg Asp Gly Ile Pro Thr Ser
        100                 105                 110

Arg Ser Val Glu Ser Tyr Asn Tyr Trp Gly Gln Gly Thr Gln Val Thr
    115                 120                 125

Val Ser Ser Ala Ala
        130

<210> SEQ ID NO 34
<211> LENGTH: 247
<212> TYPE: PRT
<213> ORGANISM: artificial sequence

```
<220> FEATURE:
<223> OTHER INFORMATION: Library 26-10-1
<220> FEATURE:
<221> NAME/KEY: misc_feature
<222> LOCATION: (197)..(200)
<223> OTHER INFORMATION: Xaa can be any naturally occurring amino acid
<220> FEATURE:
<221> NAME/KEY: misc_feature
<222> LOCATION: (216)..(222)
<223> OTHER INFORMATION: Xaa can be any naturally occurring amino acid

<400> SEQUENCE: 34
```

Glu Val Gln Leu Gln Gln Ser Gly Pro Glu Leu Val Lys Pro Gly Ala
1               5                   10                  15

Ser Val Arg Met Ser Cys Lys Ser Ser Gly Tyr Ile Phe Thr Asp Phe
            20                  25                  30

Tyr Met Asn Trp Val Arg Gln Ser His Gly Lys Ser Leu Asp Tyr Ile
        35                  40                  45

Gly Tyr Ile Ser Pro Tyr Ser Gly Val Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Ser Ser Gly Asn Lys Trp Ala Met Asp Tyr Trp Gly His Gly
            100                 105                 110

Ala Ser Val Thr Val Ser Ser Gly Gly Gly Ser Gly Gly Gly
            115                 120                 125

Ser Gly Gly Gly Ser Asp Val Val Met Thr Gln Thr Pro Leu Ser
        130                 135                 140

Leu Pro Val Ser Leu Gly Asp Gln Ala Ser Ile Ser Cys Arg Ser Ser
145                 150                 155                 160

Gln Ser Leu Val His Ser Asn Gly Asn Thr Tyr Leu Asn Trp Tyr Leu
                165                 170                 175

Gln Lys Ala Gly Gln Ser Pro Lys Leu Leu Ile Tyr Lys Val Ser Asn
            180                 185                 190

Arg Phe Ser Gly Xaa Xaa Xaa Xaa Phe Ser Gly Ser Gly Ser Gly Thr
        195                 200                 205

Asp Phe Thr Leu Lys Ile Ser Xaa Xaa Xaa Xaa Xaa Xaa Xaa Gly Ile
    210                 215                 220

Tyr Phe Cys Ser Gln Thr Thr His Val Pro Pro Thr Phe Gly Gly Gly
225                 230                 235                 240

Thr Lys Leu Glu Ile Lys Arg
            245

```
<210> SEQ ID NO 35
<211> LENGTH: 247
<212> TYPE: PRT
<213> ORGANISM: artificial sequence
<220> FEATURE:
<223> OTHER INFORMATION: Library 26-10-2
<220> FEATURE:
<221> NAME/KEY: misc_feature
<222> LOCATION: (147)..(151)
<223> OTHER INFORMATION: Xaa can be any naturally occurring amino acid
<220> FEATURE:
<221> NAME/KEY: misc_feature
<222> LOCATION: (197)..(200)
<223> OTHER INFORMATION: Xaa can be any naturally occurring amino acid
```

```
<220> FEATURE:
<221> NAME/KEY: misc_feature
<222> LOCATION: (216)..(222)
<223> OTHER INFORMATION: Xaa can be any naturally occurring amino acid

<400> SEQUENCE: 35

Glu Val Gln Leu Gln Gln Ser Gly Pro Glu Leu Val Lys Pro Gly Ala
1               5                   10                  15

Ser Val Arg Met Ser Cys Lys Ser Gly Tyr Ile Phe Thr Asp Phe
            20                  25                  30

Tyr Met Asn Trp Val Arg Gln Ser His Gly Lys Ser Leu Asp Tyr Ile
            35                  40                  45

Gly Tyr Ile Ser Pro Tyr Ser Gly Val Thr Gly Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Ser Ser Gly Asn Lys Trp Ala Met Asp Tyr Trp Gly His Gly
            100                 105                 110

Ala Ser Val Thr Val Ser Ser Gly Gly Gly Ser Gly Gly Gly
            115                 120                 125

Ser Gly Gly Gly Gly Ser Asp Val Val Met Thr Gln Thr Pro Leu Ser
        130                 135                 140

Leu Pro Xaa Xaa Xaa Xaa Xaa Gln Ala Ser Ile Ser Cys Arg Ser Ser
145                 150                 155                 160

Gln Ser Leu Val His Ser Asn Gly Asn Thr Tyr Leu Asn Trp Tyr Leu
                165                 170                 175

Gln Lys Ala Gly Gln Ser Pro Lys Leu Leu Ile Tyr Lys Val Ser Asn
            180                 185                 190

Arg Phe Ser Gly Xaa Xaa Xaa Xaa Phe Ser Gly Ser Gly Ser Gly Thr
            195                 200                 205

Asp Phe Thr Leu Lys Ile Ser Xaa Xaa Xaa Xaa Xaa Xaa Xaa Gly Ile
        210                 215                 220

Tyr Phe Cys Ser Gln Thr Thr His Val Pro Pro Thr Phe Gly Gly Gly
225                 230                 235                 240

Thr Lys Leu Glu Ile Lys Arg
                245

<210> SEQ ID NO 36
<211> LENGTH: 248
<212> TYPE: PRT
<213> ORGANISM: artificial sequence
<220> FEATURE:
<223> OTHER INFORMATION: Library 26-10-3
<220> FEATURE:
<221> NAME/KEY: misc_feature
<222> LOCATION: (147)..(151)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (217)..(223)
<223> OTHER INFORMATION: Xaa can be any naturally occurring amino acid
```

<400> SEQUENCE: 36

Glu Val Gln Leu Gln Gln Ser Gly Pro Glu Leu Val Lys Pro Gly Ala
1               5                   10                  15

Ser Val Arg Met Ser Cys Lys Ser Gly Tyr Ile Phe Thr Asp Phe
            20                  25                  30

Tyr Met Asn Trp Val Arg Gln Ser His Gly Lys Ser Leu Asp Tyr Ile
            35                  40                  45

Gly Tyr Ile Ser Pro Tyr Ser Gly Val Thr Gly Tyr Asn Gln Lys Phe
50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Ala Gly Ser Ser Gly Asn Lys Trp Ala Met Asp Tyr Trp Gly His Gly
            100                 105                 110

Ala Ser Val Thr Val Ser Ser Gly Gly Gly Ser Gly Gly Gly
            115                 120                 125

Ser Gly Gly Gly Ser Asp Val Val Met Thr Gln Thr Pro Leu Ser
    130                 135                 140

Leu Pro Xaa Xaa Xaa Xaa Xaa Gln Ala Ser Ile Ser Cys Arg Ser Ser
145                 150                 155                 160

Gln Ser Leu Val His Ser Asn Gly Asn Thr Tyr Leu Asn Trp Tyr Leu
                165                 170                 175

Gln Lys Ala Gly Gln Ser Pro Lys Leu Leu Ile Tyr Lys Val Ser Asn
            180                 185                 190

Arg Phe Ser Gly Xaa Val Pro Asp Arg Phe Ser Gly Ser Gly Ser Gly
            195                 200                 205

Thr Asp Phe Thr Leu Lys Ile Ser Xaa Xaa Xaa Xaa Xaa Xaa Gly
    210                 215                 220

Ile Tyr Phe Cys Ser Gln Thr Thr His Val Pro Pro Thr Phe Gly Gly
225                 230                 235                 240

Gly Thr Lys Leu Glu Ile Lys Arg
            245

<210> SEQ ID NO 37
<211> LENGTH: 250
<212> TYPE: PRT
<213> ORGANISM: artificial sequence
<220> FEATURE:
<223> OTHER INFORMATION: Library 26-10-4
<220> FEATURE:
<221> NAME/KEY: misc_feature
<222> LOCATION: (197)..(203)
<223> OTHER INFORMATION: Xaa can be any naturally occurring amino acid
<220> FEATURE:
<221> NAME/KEY: misc_feature
<222> LOCATION: (219)..(225)
<223> OTHER INFORMATION: Xaa can be any naturally occurring amino acid

<400> SEQUENCE: 37

Glu Val Gln Leu Gln Gln Ser Gly Pro Glu Leu Val Lys Pro Gly Ala
1               5                   10                  15

Ser Val Arg Met Ser Cys Lys Ser Gly Tyr Ile Phe Thr Asp Phe
            20                  25                  30

Tyr Met Asn Trp Val Arg Gln Ser His Gly Lys Ser Leu Asp Tyr Ile
            35                  40                  45

Gly Tyr Ile Ser Pro Tyr Ser Gly Val Thr Gly Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Ser Ser Gly Asn Lys Trp Ala Met Asp Tyr Trp Gly His Gly
            100                 105                 110

Ala Ser Val Thr Val Ser Ser Gly Gly Gly Ser Gly Gly Gly Gly
        115                 120                 125

Ser Gly Gly Gly Ser Asp Val Val Met Thr Gln Thr Pro Leu Ser
130                 135                 140

Leu Pro Val Ser Leu Gly Asp Gln Ala Ser Ile Ser Cys Arg Ser Ser
145                 150                 155                 160

Gln Ser Leu Val His Ser Asn Gly Asn Thr Tyr Leu Asn Trp Tyr Leu
                165                 170                 175

Gln Lys Ala Gly Gln Ser Pro Lys Leu Leu Ile Tyr Lys Val Ser Asn
            180                 185                 190

Arg Phe Ser Gly Xaa Xaa Xaa Xaa Xaa Xaa Phe Ser Gly Ser Gly
        195                 200                 205

Ser Gly Thr Asp Phe Thr Leu Lys Ile Ser Xaa Xaa Xaa Xaa Xaa
210                 215                 220

Xaa Gly Ile Tyr Phe Cys Ser Gln Thr Thr His Val Pro Pro Thr Phe
225                 230                 235                 240

Gly Gly Gly Thr Lys Leu Glu Ile Lys Arg
            245                 250

<210> SEQ ID NO 38
<211> LENGTH: 247
<212> TYPE: PRT
<213> ORGANISM: artificial sequence
<220> FEATURE:
<223> OTHER INFORMATION: Library 26-10-5
<220> FEATURE:
<221> NAME/KEY: misc_feature
<222> LOCATION: (40)..(45)
<223> OTHER INFORMATION: Xaa can be any naturally occurring amino acid
<220> FEATURE:
<221> NAME/KEY: misc_feature
<222> LOCATION: (178)..(183)
<223> OTHER INFORMATION: Xaa can be any naturally occurring amino acid

<400> SEQUENCE: 38

Glu Val Gln Leu Gln Gln Ser Gly Pro Glu Leu Val Lys Pro Gly Ala
1               5                   10                  15

Ser Val Arg Met Ser Cys Lys Ser Ser Gly Tyr Ile Phe Thr Asp Phe
            20                  25                  30

Tyr Met Asn Trp Val Arg Gln Xaa Xaa Xaa Xaa Xaa Xaa Asp Tyr Ile
        35                  40                  45

Gly Tyr Ile Ser Pro Tyr Ser Gly Val Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Ser Ser Gly Asn Lys Trp Ala Met Asp Tyr Trp Gly His Gly
            100                 105                 110

Ala Ser Val Thr Val Ser Ser Gly Gly Gly Ser Gly Gly Gly Gly
        115                 120                 125

-continued

```
Ser Gly Gly Gly Gly Ser Asp Val Val Met Thr Gln Thr Pro Leu Ser
    130                 135                 140

Leu Pro Val Ser Leu Gly Asp Gln Ala Ser Ile Ser Cys Arg Ser Ser
145                 150                 155                 160

Gln Ser Leu Val His Ser Asn Gly Asn Thr Tyr Leu Asn Trp Tyr Leu
                165                 170                 175

Gln Xaa Xaa Xaa Xaa Xaa Lys Leu Leu Ile Tyr Lys Val Ser Asn
                180                 185                 190

Arg Phe Ser Gly Val Pro Asp Arg Phe Ser Gly Ser Gly Ser Gly Thr
                195                 200                 205

Asp Phe Thr Leu Lys Ile Ser Arg Val Glu Ala Glu Asp Leu Gly Ile
    210                 215                 220

Tyr Phe Cys Ser Gln Thr Thr His Val Pro Pro Thr Phe Gly Gly Gly
225                 230                 235                 240

Thr Lys Leu Glu Ile Lys Arg
                245
```

<210> SEQ ID NO 39
<211> LENGTH: 741
<212> TYPE: DNA
<213> ORGANISM: artificial sequence
<220> FEATURE:
<223> OTHER INFORMATION: Library 26-10-1 gene
<220> FEATURE:
<221> NAME/KEY: misc_feature
<222> LOCATION: (589)..(590)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (595)..(596)
<223> OTHER INFORMATION: n is a, c, g, or t
<220> FEATURE:
<221> NAME/KEY: misc_feature
<222> LOCATION: (598)..(599)
<223> OTHER INFORMATION: n is a, c, g, or t
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (658)..(659)
<223> OTHER INFORMATION: n is a, c, g, or t
<220> FEATURE:
<221> NAME/KEY: misc_feature
<222> LOCATION: (661)..(662)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t

<400> SEQUENCE: 39

```
gaagttcagc tgcagcagtc tggtccggaa ctggttaaac cgggtgcttc tgttcgtatg      60
tcttgcaaat cttctggtta catcttcacc gacttctaca tgaactgggt tcgtcagtct     120
cacggtaaat ctctggacta catcggttac atctctccgt actctggtgt taccggttac     180
aaccagaaat tcaaaggtaa agctaccctg accgttgaca atcttcttc taccgcttac      240
atggaactgc gttctctgac ctctgaagac tctgctgttt actactgcgc tggttcttct     300
ggtaacaaat gggctatgga ctactggggt cacggtgctt ctgttaccgt tcttctggt      360
ggtggtggtt ctggtggtgg tggttctggt ggtggtggtt ctgacgttgt tatgacccag     420
accccgctgt ctctgccggt ttctctgggt gaccaggctt ctatctcttg ccgttcttct     480
cagtctctgg ttcactctaa cggtaacacc tacctgaact ggtacctgca gaaagctggt     540
cagtctccga aactgctgat ctacaaagtt tctaaccgtt tctctggtnn knnknnknnk     600
ttctctggtt ctggttctgg taccgacttc accctgaaaa tctctnnknn knnknnknnk     660
nnknnkggta tctacttctg ctctcagacc cccacgttc cgccgacctt cggtggtggt      720
accaaactgg aaatcaaacg t                                               741
```

<210> SEQ ID NO 40
<211> LENGTH: 741
<212> TYPE: DNA
<213> ORGANISM: artificial sequence
<220> FEATURE:
<223> OTHER INFORMATION: Library 26-10-2 gene
<220> FEATURE:
<221> NAME/KEY: misc_feature
<222> LOCATION: (439)..(440)
<223> OTHER INFORMATION: n is a, c, g, or t
<220> FEATURE:
<221> NAME/KEY: misc_feature
<222> LOCATION: (442)..(443)
<223> OTHER INFORMATION: n is a, c, g, or t
<220> FEATURE:
<221> NAME/KEY: misc_feature
<222> LOCATION: (445)..(446)
<223> OTHER INFORMATION: n is a, c, g, or t
<220> FEATURE:
<221> NAME/KEY: misc_feature
<222> LOCATION: (448)..(449)
<223> OTHER INFORMATION: n is a, c, g, or t
<220> FEATURE:
<221> NAME/KEY: misc_feature
<222> LOCATION: (451)..(452)
<223> OTHER INFORMATION: n is a, c, g, or t
<220> FEATURE:
<221> NAME/KEY: misc_feature
<222> LOCATION: (589)..(590)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (595)..(596)
<223> OTHER INFORMATION: n is a, c, g, or t
<220> FEATURE:
<221> NAME/KEY: misc_feature
<222> LOCATION: (598)..(599)
<223> OTHER INFORMATION: n is a, c, g, or t
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (658)..(659)
<223> OTHER INFORMATION: n is a, c, g, or t
<220> FEATURE:
<221> NAME/KEY: misc_feature
<222> LOCATION: (661)..(662)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t

<400> SEQUENCE: 40

```
gaagttcagc tgcagcagtc tggtccggaa ctggttaaac cgggtgcttc tgttcgtatg    60
tcttgcaaat cttctggtta catcttcacc gacttctaca tgaactgggt tcgtcagtct   120
cacggtaaat ctctggacta catcggttac atctctccgt actctggtgt taccggttac   180
aaccagaaat tcaaaggtaa agctaccctg accgttgaca atcttcttc taccgcttac    240
atggaactgc gttctctgac ctctgaagac tctgctgttt actactgcgc tggttcttct   300
ggtaacaaat gggctatgga ctactggggt cacggtgctt ctgttaccgt tcttctggt    360
ggtggtggtt ctggtggtgg tggttctggt ggtggtggtt ctgacgttgt tatgacccag   420
accccgctgt ctctgccgnn knnknnknnk nnkcaggctt ctatctcttg ccgttcttct   480
cagtctctgg ttcactctaa cggtaacacc tacctgaact ggtacctgca gaaagctggt   540
cagtctccga actgctgat ctacaaagtt tctaaccgtt tctctggtnn knnknnknnk    600
ttctctggtt ctggttctgg taccgacttc accctgaaaa tctctnnknn knnknnknnk   660
nnknnkggta tctacttctg ctctcagacc acccacgttc cgccgacctt cggtggtggt   720
accaaactgg aaatcaaacg t                                             741
```

<210> SEQ ID NO 41
<211> LENGTH: 741
<212> TYPE: DNA
<213> ORGANISM: artificial sequence
<220> FEATURE:
<223> OTHER INFORMATION: Library 26-10-3 gene
<220> FEATURE:
<221> NAME/KEY: misc_feature
<222> LOCATION: (439)..(440)
<223> OTHER INFORMATION: n is a, c, g, or t
<220> FEATURE:
<221> NAME/KEY: misc_feature
<222> LOCATION: (442)..(443)
<223> OTHER INFORMATION: n is a, c, g, or t
<220> FEATURE:
<221> NAME/KEY: misc_feature
<222> LOCATION: (445)..(446)
<223> OTHER INFORMATION: n is a, c, g, or t
<220> FEATURE:
<221> NAME/KEY: misc_feature
<222> LOCATION: (448)..(449)
<223> OTHER INFORMATION: n is a, c, g, or t
<220> FEATURE:
<221> NAME/KEY: misc_feature
<222> LOCATION: (451)..(452)
<223> OTHER INFORMATION: n is a, c, g, or t
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (658)..(659)
<223> OTHER INFORMATION: n is a, c, g, or t
<220> FEATURE:
<221> NAME/KEY: misc_feature
<222> LOCATION: (661)..(662)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t

<400> SEQUENCE: 41

```
gaagttcagc tgcagcagtc tggtccggaa ctggttaaac cgggtgcttc tgttcgtatg      60
tcttgcaaat cttctggtta catcttcacc gacttctaca tgaactgggt tcgtcagtct     120
cacggtaaat ctctggacta catcggttac atctctccgt actctggtgt taccggttac     180
aaccagaaat tcaaaggtaa agctaccctg accgttgaca atcttcttc taccgcttac     240
atggaactgc gttctctgac ctctgaagac tctgctgttt actactgcgc tggttcttct     300
ggtaacaaat gggctatgga ctactggggt cacggtgctt ctgttaccgt tcttctggt     360
ggtggtggtt ctggtggtgg tggttctggt ggtggtggtt ctgacgttgt tatgacccag     420
accccgctgt ctctgccgnn knnknnknnk nnkcaggctt ctatctcttg ccgttcttct     480
cagtctctgg ttcactctaa cggtaacacc tacctgaact ggtacctgca gaaagctggt     540
cagtctccga aactgctgat ctacaaagtt tctaaccgtt tctctggtgt tccggaccgt     600
ttctctggtt ctggttctgg taccgacttc accctgaaaa tctctnnknn knnknnknnk     660
nnknnkggta tctacttctg ctctcagacc acccacgttc cgccgacctt cggtggtggt     720
accaaactgg aaatcaaacg t                                               741
```

<210> SEQ ID NO 42
<211> LENGTH: 750
<212> TYPE: DNA
<213> ORGANISM: artificial sequence
<220> FEATURE:
<223> OTHER INFORMATION: Library 26-10-4 gene
<220> FEATURE:
<221> NAME/KEY: misc_feature
<222> LOCATION: (589)..(590)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (595)..(596)
<223> OTHER INFORMATION: n is a, c, g, or t

```
<220> FEATURE:
<221> NAME/KEY: misc_feature
<222> LOCATION: (598)..(599)
<223> OTHER INFORMATION: n is a, c, g, or t
<220> FEATURE:
<221> NAME/KEY: misc_feature
<222> LOCATION: (601)..(602)
<223> OTHER INFORMATION: n is a, c, g, or t
<220> FEATURE:
<221> NAME/KEY: misc_feature
<222> LOCATION: (604)..(605)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (658)..(659)
<223> OTHER INFORMATION: n is a, c, g, or t
<220> FEATURE:
<221> NAME/KEY: misc_feature
<222> LOCATION: (661)..(662)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t
<220> FEATURE:
<221> NAME/KEY: misc_feature
<222> LOCATION: (667)..(668)
<223> OTHER INFORMATION: n is a, c, g, or t
<220> FEATURE:
<221> NAME/KEY: misc_feature
<222> LOCATION: (670)..(671)
<223> OTHER INFORMATION: n is a, c, g, or t
<220> FEATURE:
<221> NAME/KEY: misc_feature
<222> LOCATION: (673)..(674)
<223> OTHER INFORMATION: n is a, c, g, or t

<400> SEQUENCE: 42
gaagttcagc tgcagcagtc tggtccggaa ctggttaaac cgggtgcttc tgttcgtatg    60
tcttgcaaat cttctggtta catcttcacc gacttctaca tgaactgggt tcgtcagtct   120
cacggtaaat ctctggacta catcggttac atctctccgt actctggtgt taccggttac   180
aaccagaaat tcaaaggtaa agctaccctg accgttgaca atcttcttc taccgcttac   240 atggaactgc gttctctgac ctctgaagac tctgctgttt actactgcgc tggttcttct   300
ggtaacaaat gggctatgga ctactggggt cacggtgctt ctgttaccgt ttcttctggt   360
ggtggtggtt ctggtggtgg tggttctggt ggtggtggtt ctgacgttgt tatgacccag   420
accccgctgt ctctgccggt ttctctgggt gaccaggctt ctatctcttg ccgttcttct   480
cagtctctgg ttcactctaa cggtaacacc tacctgaact ggtacctgca gaaagctggt   540
cagtctccga aactgctgat ctacaaagtt tctaaccgtt tctctggtnn knnknnknnk   600
nnknnknnkt tctctggttc tggttctggt accgacttca ccctgaaaat ctctnnknnk   660
nnknnknnkn nknnkggtat ctacttctgc tctcagacca cccacgttcc gccgaccttc   720
ggtggtggta ccaaactgga aatcaaacgt                                   750

<210> SEQ ID NO 43
<211> LENGTH: 741
<212> TYPE: DNA
<213> ORGANISM: artificial sequence
```

```
<220> FEATURE:
<223> OTHER INFORMATION: Library 26-10-5 gene
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (130)..(131)
<223> OTHER INFORMATION: n is a, c, g, or t
<220> FEATURE:
<221> NAME/KEY: misc_feature
<222> LOCATION: (133)..(134)
<223> OTHER INFORMATION: n is a, c, g, or t
<220> FEATURE:
<221> NAME/KEY: misc_feature
<222> LOCATION: (532)..(533)
<223> OTHER INFORMATION: n is a, c, g, or t
<220> FEATURE:
<221> NAME/KEY: misc_feature
<222> LOCATION: (535)..(536)
<223> OTHER INFORMATION: n is a, c, g, or t
<220> FEATURE:
<221> NAME/KEY: misc_feature
<222> LOCATION: (538)..(539)
<223> OTHER INFORMATION: n is a, c, g, or t
<220> FEATURE:
<221> NAME/KEY: misc_feature
<222> LOCATION: (541)..(542)
<223> OTHER INFORMATION: n is a, c, g, or t
<220> FEATURE:
<221> NAME/KEY: misc_feature
<222> LOCATION: (544)..(545)
<223> OTHER INFORMATION: n is a, c, g, or t
<220> FEATURE:
<221> NAME/KEY: misc_feature
<222> LOCATION: (547)..(548)
<223> OTHER INFORMATION: n is a, c, g, or t

<400> SEQUENCE: 43
gaagttcagc tgcagcagtc tggtccggaa ctggttaaac cgggtgcttc tgttcgtatg      60
tcttgcaaat cttctggtta catcttcacc gacttctaca tgaactgggt tcgtcagnnk     120
nnknnknnkn nknnkgacta catcggttac atctctccgt actctggtgt taccggttac     180
aaccagaaat tcaaaggtaa agctaccctg accgttgaca atcttcttc taccgcttac      240 atggaactgc gttctctgac ctctgaagac tctgctgttt actactgcgc tggttcttct     300
ggtaacaaat gggctatgga ctactggggt cacggtgctt ctgttaccgt ttcttctggt     360
ggtggtggtt ctggtggtgg tggttctggt ggtggtggtt ctgacgttgt tatgacccag     420 acccgctgt ctctgccggt ttctctgggt gaccaggctt ctatctcttg ccgttcttct      480
cagtctctgg ttcactctaa cggtaacacc tacctgaact ggtacctgca gnnknnknnk     540
nnknnknnka aactgctgat ctacaaagtt tctaaccgtt ctctggtgt tccggaccgt      600 ttctctggtt ctggttctgg taccgacttc accctgaaaa tctctcgtgt tgaagctgaa     660
gacctgggta tctacttctg ctctcagacc acccacgttc cgccgacctt cggtggtggt     720
accaaactgg aaatcaaacg t                                                741
```

```
<210> SEQ ID NO 44
<211> LENGTH: 236
<212> TYPE: PRT
<213> ORGANISM: artificial sequence
<220> FEATURE:
<223> OTHER INFORMATION: protein VL-CL

<400> SEQUENCE: 44

Met Lys Tyr Leu Leu Pro Thr Ala Ala Ala Gly Leu Leu Leu Ala
1               5                   10                  15

Ala Gln Pro Ala Met Ala Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 45
<211> LENGTH: 666
<212> TYPE: PRT
<213> ORGANISM: artificial sequence
<220> FEATURE:
<223> OTHER INFORMATION: VH-CH1 fused to protein III of phage M13

<400> SEQUENCE: 45

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80
```

-continued

```
Thr Arg Tyr Ala Asp Ser Val Lys Gly Arg Phe Thr Ile Ser Ala Asp
                 85                  90                  95
Thr Ser Lys Asn Thr Ala Tyr Leu Gln Met Asn Ser Leu Arg Ala Glu
            100                 105                 110
Asp Thr Ala Val Tyr Tyr Cys Ser Arg Trp Gly Gly Asp Gly Phe Tyr
        115                 120                 125
Ala Met Asp Tyr Trp Gly Gln Gly Thr Leu Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Ala Ala Ala Glu Gln Lys Leu Ile Ser Glu
                245                 250                 255
Glu Asp Leu Asn Gly Ala Ala Thr Val Glu Ser Cys Leu Ala Lys Pro
            260                 265                 270
His Thr Glu Asn Ser Phe Thr Asn Val Trp Lys Asp Asp Lys Thr Leu
        275                 280                 285
Asp Arg Tyr Ala Asn Tyr Glu Gly Cys Leu Trp Asn Ala Thr Gly Val
    290                 295                 300
Val Val Cys Thr Gly Asp Glu Thr Gln Cys Tyr Gly Thr Trp Val Pro
305                 310                 315                 320
Ile Gly Leu Ala Ile Pro Glu Asn Glu Gly Gly Ser Glu Gly Gly
                325                 330                 335
Gly Ser Glu Gly Gly Gly Ser Glu Gly Gly Gly Thr Lys Pro Pro Glu
            340                 345                 350
Tyr Gly Asp Thr Pro Ile Pro Gly Tyr Thr Tyr Ile Asn Pro Leu Asp
        355                 360                 365
Gly Thr Tyr Pro Pro Gly Thr Glu Gln Asn Pro Ala Asn Pro Asn Pro
    370                 375                 380
Ser Leu Glu Glu Ser Gln Pro Leu Asn Thr Phe Met Phe Gln Asn Asn
385                 390                 395                 400
Arg Phe Arg Asn Arg Gln Gly Ala Leu Thr Val Tyr Thr Gly Thr Val
                405                 410                 415
Thr Gln Gly Thr Asp Pro Val Lys Thr Tyr Tyr Gln Tyr Thr Pro Val
            420                 425                 430
Ser Ser Lys Ala Met Tyr Asp Ala Tyr Trp Asn Gly Lys Phe Arg Asp
        435                 440                 445
Cys Ala Phe His Ser Gly Phe Asn Glu Asp Pro Phe Val Cys Glu Tyr
    450                 455                 460
Gln Gly Gln Ser Ser Asp Leu Pro Gln Pro Pro Val Asn Ala Gly Gly
465                 470                 475                 480
Gly Ser Gly Gly Gly Ser Gly Gly Ser Glu Gly Gly Ser Glu
                485                 490                 495
```

```
Gly Gly Gly Ser Glu Gly Gly Ser Gly Gly Ser Gly Gly
            500                 505                 510
Gly Ser Gly Ser Gly Asp Phe Asp Tyr Glu Lys Met Ala Asn Ala Asn
            515                 520                 525
Lys Gly Ala Met Thr Glu Asn Ala Asp Glu Asn Ala Leu Gln Ser Asp
            530                 535                 540
Ala Lys Gly Lys Leu Asp Ser Val Ala Thr Asp Tyr Gly Ala Ala Ile
545                 550                 555                 560
Asp Gly Phe Ile Gly Asp Val Ser Gly Leu Ala Asn Gly Asn Gly Ala
                565                 570                 575
Thr Gly Asp Phe Ala Gly Ser Asn Ser Gln Met Ala Gln Val Gly Asp
            580                 585                 590
Gly Asp Asn Ser Pro Leu Met Asn Asn Phe Arg Gln Tyr Leu Pro Ser
            595                 600                 605
Leu Pro Gln Ser Val Glu Cys Arg Pro Tyr Val Phe Gly Ala Gly Lys
            610                 615                 620
Pro Tyr Glu Phe Ser Ile Asp Cys Asp Lys Ile Asn Leu Phe Arg Gly
625                 630                 635                 640
Val Phe Ala Phe Leu Leu Tyr Val Ala Thr Phe Met Tyr Val Phe Ser
                645                 650                 655
Thr Phe Ala Asn Ile Leu His Lys Glu Ser
            660                 665

<210> SEQ ID NO 46
<211> LENGTH: 5958
<212> TYPE: DNA
<213> ORGANISM: artificial sequence
<220> FEATURE:
<223> OTHER INFORMATION: Fab 4D5 display vector

<400> SEQUENCE: 46
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gttttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacgatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
```

```
catatatact ttagattgat ttaaaacttc attttaatt taaaaggatc taggtgaaga   1140
tccttttga  taatctcatg accaaaatcc cttaacgtga gttttcgttc cactgagcgt   1200
cagaccccgt agaaaagatc aaaggatctt cttgagatcc ttttttctg  cgcgtaatct   1260
gctgcttgca acaaaaaaa  ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga agcgccacg  cttcccgaag gagaaaggc  ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttgtga  tgctcgtcag   1800
gggggcggag cctatggaaa aacgccagca acgcggcctt tttacggttc ctggccttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gcatgcaaat tctatttcaa ggagacagtc ataatgaaat   2280
acctattgcc tacggcagcc gctggattgt tattactcgc ggcccagccg gccatggccg   2340
atatccagat gacccagtcc ccgagctccc tgtccgcctc tgtgggcgat agggtcacca   2400
tcacctgccg tgccagtcag gatgtgaata ctgctgtagc ctggtatcaa cagaaaccag   2460
gaaaagctcc gaaactactg atttactcgg catccttcct ctactctgga gtcccttctc   2520
gcttctctgg atccagatct gggacggatt tcactctgac catcagcagt ctgcagccgg   2580
aagacttcgc aacttattac tgtcagcaac attatactac tcctcccacg ttcggacagg   2640
gtaccaaggt ggagatcaaa cgtacggtgg cggcgccatc tgtcttcatc ttcccgccat   2700
ctgatgagca gcttaagtct ggaactgcct ctgttgtgtg cctgctgaat aacttctatc   2760
ccagagaggc caaagtacag tggaaggtgg ataacgccct ccaatcgggt aactcccagg   2820
agagtgtcac agagcaggac agcaaggaca gcacctacag cctcagcagc accctgacgc   2880
tgagcaaagc agactacgag aaacacaaag tctacgcctg cgaagtcacc catcagggcc   2940
tgagctcgcc cgtcacaaag agcttcaaca ggggagagtg ttaataaggc gcgccgctga   3000
tcctctacgc cggacgcatc gtggccctag tacgcaagtt cacgtaaaaa gggtatctag   3060
aggttgaggt gattttatga aaagaatat  cgcatttctt cttgcatcta tgttcgtttt   3120
ttctattgct acaaatgcat acgctgaggt tcaactagtg gagtctggcg gtggcctggt   3180
gcagccaggg ggctcactcc gtttgtcctg tgcagcttct ggcttcaaca ttaaagacac   3240
ctatatacac tgggtgcgtc aggccccggg taagggcctg gaatggggttg caaggattta   3300
tcctacgaat ggttatacta gatatgccga tagcgtcaag ggccgtttca ctataagcgc   3360
agacacatcc aaaaacacag cctacctgca gatgaacagc ctgcgtgctg aggacactgc   3420
cgtctattat tgttctagat ggggagggga cggcttctat gctatggact actggggtca   3480
```

```
aggaaccctg gtcaccgtct cctcggcgtc gaccaagggc ccatcggtct tccccctggc    3540
accctcctcc aagagcacct ctggggcac agcggccctg gctgcctgg tcaaggacta     3600 cttcccccgaa ccggtgacgg tgtcgtggaa ctcaggtgcc ctgaccagcg gcgtgcacac    3660
cttcccggct gtcctacagt cctcaggact ctactcctc agcagcgtgg tgaccgtgcc     3720
ctccagcagc ttgggcaccc agacctacat ctgcaacgtg aatcacaagc ccagcaacac    3780
caaggtggac aagaaagttg agcccaaatc ttgtgcggcc gcagaacaaa aactcatctc    3840
agaagaggat ctgaatgggg ccgcatagac tgttgaaagt tgtttagcaa aacctcatac    3900
agaaaattca tttactaacg tctggaaaga cgacaaaact ttagatcgtt acgctaacta    3960
tgagggctgt ctgtggaatg ctacaggcgt tgtggtttgt actggtgacg aaactcagtg    4020
ttacggtaca tgggttccta ttgggcttgc tatccctgaa aatgagggtg gtggctctga    4080
gggtggcggt tctgagggtg gcggttctga gggtggcggt actaaacctc ctgagtacgg    4140
tgatacacct attccgggct atacttatat caaccctctc gacggcactt atccgcctgg    4200
tactgagcaa aaccccgcta atcctaatcc ttctcttgag gagtctcagc ctcttaatac    4260
tttcatgttt cagaataata ggttccgaaa taggcagggt gcattaactg tttatacggg    4320
cactgttact caaggcactg accccgttaa aacttattac cagtacactc ctgtatcatc    4380
aaaagccatg tatgacgctt actggaacgg taaattcaga gactgcgctt tccattctgg    4440
ctttaatgag gatccattcg tttgtgaata tcaaggccaa tcgtctgacc tgcctcaacc    4500
tcctgtcaat gctggcggcg gctctggtgg tggttctggt ggcggctctg agggtggcgg    4560
ctctgagggt ggcggttctg agggtggcgg ctctgagggt ggcggttccg gtggcggctc    4620
cggttccggt gattttgatt atgaaaaaat ggcaaacgct aataagggg ctatgaccga    4680 aaatgccgat gaaaacgcgc tacagtctga cgctaaaggc aaacttgatt ctgtcgctac    4740
tgattacggt gctgctatcg atggtttcat tggtgacgtt tccggccttg ctaatggtaa    4800
tggtgctact ggtgattttg ctggctctaa ttcccaaatg gctcaagtcg gtgacggtga    4860
taattcacct ttaatgaata atttccgtca atatttacct tctttgcctc agtcggttga    4920
atgtcgccct tatgtctttg gcgctggtaa accatatgaa ttttctattg attgtgacaa    4980
aataaactta ttccgtggtg tctttgcgtt tcttttatat gttgccacct ttatgtatgt    5040
attttcgacg tttgctaaca tactgcataa ggagtcttaa taagaattca ctggccgtcg    5100
ttttacaacg tcgtgactgg gaaaaccctg gcgttaccca acttaatcgc cttgcagcac    5160 atccccctt cgccagctgg cgtaatagcg aagaggcccg caccgatcgc ccttcccaac    5220
agttgcgcag cctgaatggc gaatggcgcc tgatgcggta ttttctcctt acgcatctgt    5280
gcggtatttc acaccgcacg tcaaagcaac catagtacgc gccctgtagc ggcgcattaa    5340
gcgcggcggg tgtggtggtt acgcgcagcg tgaccgctac acttgccagc gccctagcgc    5400
ccgctccttt cgctttcttc ccttcctttc tcgccacgtt cgccggcttt ccccgtcaag    5460
ctctaaatcg ggggctccct ttagggttcc gatttagtgc tttacggcac ctcgacccca    5520
aaaaacttga tttgggtgat ggttcacgta gtgggccatc gccctgatag acggtttttc    5580
gccctttgac gttggagtcc acgttcttta atagtggact cttgttccaa actggaacaa    5640
cactcaaccc tatctcgggc tattcttttg atttataagg gattttgccg atttcggcct    5700
attggttaaa aaatgagctg atttaacaaa aatttaacgc gaattttaac aaaatattaa    5760
cgtttacaat tttatggtgc actctcagta caatctgctc tgatgccgca tagttaagcc    5820
agccccgaca cccgccaaca cccgctgacg cgccctgacg ggcttgtctg ctcccggcat    5880
```

```
ccgcttacag acaagctgtg accgtctccg ggagctgcat gtgtcagagg tttttcaccgt    5940 catcaccgaa acgcgcga                                                   5958
```

<210> SEQ ID NO 47
<211> LENGTH: 344
<212> TYPE: DNA
<213> ORGANISM: artificial sequence
<220> FEATURE:
<223> OTHER INFORMATION: synthetic gene
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (232)..(233)
<223> OTHER INFORMATION: n is a, c, g, or t
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (247)..(248)
<223> OTHER INFORMATION: n is a, c, g, or t
<220> FEATURE:
<221> NAME/KEY: misc_feature
<222> LOCATION: (250)..(251)
<223> OTHER INFORMATION: n is a, c, g, or t
<220> FEATURE:
<221> NAME/KEY: misc_feature
<222> LOCATION: (253)..(254)
<223> OTHER INFORMATION: n is a, c, g, or t

<400> SEQUENCE: 47

```
cgtacggtgg cggcgccatc tgtcttcatc ttcccgccat ctgatgagca gcttaagtct      60
nnbnnbnnbg gaactgcctc tgttgtgtgc ctgctgaata acttctatcc cagagaggcc     120
aaagtacagt ggaaggtgga taacgccctc caatcgggta actcccagga gagtgtcaca     180
gagcaggaca gcaaggacag cacctacagc ctcagcagca ccctgacgct gnnbnnbnnb     240
nnbtacnnbn nbnnbaaagt ctacgcctgc gaagtcaccc atcagggcct gagctcgccc     300
gtcacaaaga gcttcaacag gggagagtgt taataaggcg cgcc                     344
```

<210> SEQ ID NO 48
<211> LENGTH: 347
<212> TYPE: DNA
<213> ORGANISM: artificial sequence
<220> FEATURE:
<223> OTHER INFORMATION: synthetic gene
<220> FEATURE:
<221> NAME/KEY: misc_feature
<222> LOCATION: (61)..(62)
<223> OTHER INFORMATION: n is a, c, g, or t

```
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (250)..(251)
<223> OTHER INFORMATION: n is a, c, g, or t
<220> FEATURE:
<221> NAME/KEY: misc_feature
<222> LOCATION: (253)..(254)
<223> OTHER INFORMATION: n is a, c, g, or t
<220> FEATURE:
<221> NAME/KEY: misc_feature
<222> LOCATION: (256)..(257)
<223> OTHER INFORMATION: n is a, c, g, or t

<400> SEQUENCE: 48
cgtacggtgg cggcgccatc tgtcttcatc ttcccgccat ctgatgagca gcttaagtct    60
nnbnnbnnbn nbggaactgc ctctgttgtg tgcctgctga ataacttcta tcccagagag   120
gccaaagtac agtggaaggt ggataacgcc ctccaatcgg gtaactccca ggagagtgtc   180
acagagcagg acagcaagga cagcacctac agcctcagca gcaccctgac gctgnnbnnb   240
nnbnnbtacn nbnnbnnbaa agtctacgcc tgcgaagtca cccatcaggg cctgagctcg   300
cccgtcacaa agagcttcaa caggggagag tgttaataag gcgcgcc                347

<210> SEQ ID NO 49
<211> LENGTH: 350
<212> TYPE: DNA
<213> ORGANISM: artificial sequence
<220> FEATURE:
<223> OTHER INFORMATION: synthetic gene
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
```

```
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (247)..(248)
<223> OTHER INFORMATION: n is a, c, g, or t
<220> FEATURE:
<221> NAME/KEY: misc_feature
<222> LOCATION: (253)..(254)
<223> OTHER INFORMATION: n is a, c, g, or t
<220> FEATURE:
<221> NAME/KEY: misc_feature
<222> LOCATION: (256)..(257)
<223> OTHER INFORMATION: n is a, c, g, or t
<220> FEATURE:
<221> NAME/KEY: misc_feature
<222> LOCATION: (259)..(260)
<223> OTHER INFORMATION: n is a, c, g, or t

<400> SEQUENCE: 49
cgtacggtgg cggcgccatc tgtcttcatc ttcccgccat ctgatgagca gcttaagtct      60
nnbnnbnnbn nbnnbggaac tgcctctgtt gtgtgcctgc tgaataactt ctatcccaga     120
gaggccaaag tacagtggaa ggtggataac gccctccaat cgggtaactc ccaggagagt     180
gtcacagagc aggacagcaa ggacagcacc tacagcctca gcagcaccct gacgctgnnb     240
nnbnnbnnbt acnnbnnbnn baaagtctac gcctgcgaag tcacccatca gggcctgagc     300
tcgcccgtca caaagagctt caacagggga gagtgttaat aaggcgcgcc                350

<210> SEQ ID NO 50
<211> LENGTH: 110
<212> TYPE: PRT
<213> ORGANISM: artificial sequence
<220> FEATURE:
<223> OTHER INFORMATION: synthetic amino acid sequence
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (78)..(81)
<223> OTHER INFORMATION: Xaa can be any naturally occurring amino acid
<220> FEATURE:
<221> NAME/KEY: misc_feature
<222> LOCATION: (83)..(85)
<223> OTHER INFORMATION: Xaa can be any naturally occurring amino acid

<400> SEQUENCE: 50

Arg Thr Val Ala Ala Pro Ser Val Phe Ile Phe Pro Pro Ser Asp Glu
1               5                   10                  15

Gln Leu Lys Ser Xaa Xaa Xaa Gly Thr Ala Ser Val Val Cys Leu Leu
            20                  25                  30

Asn Asn Phe Tyr Pro Arg Glu Ala Lys Val Gln Trp Lys Val Asp Asn
        35                  40                  45
```

```
Ala Leu Gln Ser Gly Asn Ser Gln Glu Ser Val Thr Glu Gln Asp Ser
    50                  55                  60

Lys Asp Ser Thr Tyr Ser Leu Ser Ser Thr Leu Thr Leu Xaa Xaa Xaa
 65                  70                  75                  80

Xaa Tyr Xaa Xaa Xaa Lys Val Tyr Ala Cys Glu Val Thr His Gln Gly
                85                  90                  95

Leu Ser Ser Pro Val Thr Lys Ser Phe Asn Arg Gly Glu Cys
            100                 105                 110

<210> SEQ ID NO 51
<211> LENGTH: 111
<212> TYPE: PRT
<213> ORGANISM: artificial sequence
<220> FEATURE:
<223> OTHER INFORMATION: synthetic amino acid sequence
<220> FEATURE:
<221> NAME/KEY: misc_feature
<222> LOCATION: (21)..(24)
<223> OTHER INFORMATION: Xaa can be any naturally occurring amino acid
<220> FEATURE:
<221> NAME/KEY: misc_feature
<222> LOCATION: (79)..(82)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid

<400> SEQUENCE: 51

Arg Thr Val Ala Ala Pro Ser Val Phe Ile Phe Pro Pro Ser Asp Glu
 1               5                  10                  15

Gln Leu Lys Ser Xaa Xaa Xaa Xaa Gly Thr Ala Ser Val Val Cys Leu
                20                  25                  30

Leu Asn Asn Phe Tyr Pro Arg Glu Ala Lys Val Gln Trp Lys Val Asp
            35                  40                  45

Asn Ala Leu Gln Ser Gly Asn Ser Gln Glu Ser Val Thr Glu Gln Asp
 50                  55                  60

Ser Lys Asp Ser Thr Tyr Ser Leu Ser Ser Thr Leu Thr Leu Xaa Xaa
 65                  70                  75                  80

Xaa Xaa Tyr Xaa Xaa Xaa Lys Val Tyr Ala Cys Glu Val Thr His Gln
                85                  90                  95

Gly Leu Ser Ser Pro Val Thr Lys Ser Phe Asn Arg Gly Glu Cys
            100                 105                 110

<210> SEQ ID NO 52
<211> LENGTH: 112
<212> TYPE: PRT
<213> ORGANISM: artificial sequence
<220> FEATURE:
<223> OTHER INFORMATION: synthetic amino acid sequence
<220> FEATURE:
<221> NAME/KEY: misc_feature
<222> LOCATION: (21)..(25)
<223> OTHER INFORMATION: Xaa can be any naturally occurring amino acid
<220> FEATURE:
<221> NAME/KEY: misc_feature
<222> LOCATION: (80)..(83)
<223> OTHER INFORMATION: Xaa can be any naturally occurring amino acid
<220> FEATURE:
<221> NAME/KEY: misc_feature
<222> LOCATION: (85)..(87)
<223> OTHER INFORMATION: Xaa can be any naturally occurring amino acid
```

<400> SEQUENCE: 52

Arg Thr Val Ala Ala Pro Ser Val Phe Ile Phe Pro Pro Ser Asp Glu
1               5                   10                  15

Gln Leu Lys Ser Xaa Xaa Xaa Xaa Gly Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Xaa
65                  70                  75                  80

Xaa Xaa Xaa Tyr Xaa Xaa Xaa Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 53
<211> LENGTH: 401
<212> TYPE: DNA
<213> ORGANISM: artificial sequence
<220> FEATURE:
<223> OTHER INFORMATION: synthetic gene coding for the anti-TNF-alpha
      camel VHH domain

<400> SEQUENCE: 53
ccatggcaag ttcagctgca ggaaagcggt ggcggcctgg tccagcctgg cggcagcctg      60
cgtctgagct gtgcggccag cggccgtacc tttagcgacc atagcggcta cacctatacc     120
attggctggt tcgtcaggc gccaggaaaa gaacgtgaat tgtggcgcg tatttactgg       180 agcagcggca atacctatta tgcggatagc gtgaaaggcc gtttcgcgat tagccgcgac     240
attgccaaga acacggtaga tcttacgatg aacaacctgg agcccgaaga cacagccgtg     300
tattattgcg cggctcggga tggcattccg ccagccgta gcgtggaaag ctacaattac      360
tggggccagg gcacccaggt gaccgtcagc tctgcggccg c                         401

<210> SEQ ID NO 54
<211> LENGTH: 133
<212> TYPE: PRT
<213> ORGANISM: artificial sequence
<220> FEATURE:
<223> OTHER INFORMATION: amino acid translation of SEQ ID NO:53

<400> SEQUENCE: 54

Pro Trp Gln Val Gln Leu Gln Glu Ser Gly Gly Gly Leu Val Gln Pro
1               5                   10                  15

Gly Gly Ser Leu Arg Leu Ser Cys Ala Ala Ser Gly Arg Thr Phe Ser
            20                  25                  30

Asp His Ser Gly Tyr Thr Tyr Thr Ile Gly Trp Phe Arg Gln Ala Pro
        35                  40                  45

Gly Lys Glu Arg Glu Phe Val Ala Arg Ile Tyr Trp Ser Ser Gly Asn
    50                  55                  60

Thr Tyr Tyr Ala Asp Ser Val Lys Gly Arg Phe Ala Ile Ser Arg Asp
65                  70                  75                  80

Ile Ala Lys Asn Thr Val Asp Leu Thr Met Asn Asn Leu Glu Pro Glu
                85                  90                  95

Asp Thr Ala Val Tyr Tyr Cys Ala Ala Arg Asp Gly Ile Pro Thr Ser
            100                 105                 110

Arg Ser Val Glu Ser Tyr Asn Tyr Trp Gly Gln Gly Thr Gln Val Thr
        115                 120                 125

Val Ser Ser Ala Ala
    130

<210> SEQ ID NO 55
<211> LENGTH: 791
<212> TYPE: DNA
<213> ORGANISM: artificial sequence
<220> FEATURE:
<223> OTHER INFORMATION: scFv 2F5 wt synthetic gene library 1
      (VH-Linker-VL)
<220> FEATURE:
<221> NAME/KEY: misc_feature
<222> LOCATION: (196)..(197)
<223> OTHER INFORMATION: n is a, c, g, or t
<220> FEATURE:
<221> NAME/KEY: misc_feature
<222> LOCATION: (199)..(200)
<223> OTHER INFORMATION: n is a, c, g, or t
<220> FEATURE:
<221> NAME/KEY: misc_feature
<222> LOCATION: (202)..(203)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (208)..(209)
<223> OTHER INFORMATION: n is a, c, g, or t
<220> FEATURE:
<221> NAME/KEY: misc_feature
<222> LOCATION: (259)..(260)
<223> OTHER INFORMATION: n is a, c, g, or t
<220> FEATURE:
<221> NAME/KEY: misc_feature
<222> LOCATION: (262)..(263)
<223> OTHER INFORMATION: n is a, c, g, or t

<400> SEQUENCE: 55 ccatgcgga tcaccctgaa agagagtgga ccccccctgg tgaaacctac ccagaccctg      60
actctgactt gctcatttag cggctttagc ctgagcgatt ttggcgtcgg cgttggttgg    120
attcgccagc ctcccggcaa agccctggaa tggctggcca tcatctactc cgatgatgac    180
aagcgttata gccccnnsnn snnsnnsnns ctgaccatca ccaaagatac gagcaagaac    240
caggtggttt tggtaatgnn snnsgtgagc cccgtcgaca ccgcgactta tttctgtgcc    300
catcgtcgtg gtccgaccac cctgtttggt gtgccgattg cacgcggtcc cgtgaatgcg    360
atggatgtgt gggggcaggg gattaccgtg accatttcat ccggtggagg tggtagtgga    420
gggggtgggt caggcggtgg cggctccgcc ttacaactga cgcagagccc gtctagtttg    480
agcgcaagcg tgggcgatcg tattacaatt acctgtcggg cgagccaagg tgttacctcc    540
gccctggcct ggtatcgtca gaaacccggg agcccgccac agttgttgat ctacgatgcg    600
tcctcactgg aatcaggggt ccctagccgc ttttccgggt ccggcagcgg cacggaattt    660
acattgacca taagcacccct gcgtccggaa gattttgcca cctattattg ccaacagctg    720
cacttttatc cccataccct cggtgggggg acgcgggttg acgtgcgtcg taccgtagct    780
gctgcggccg c                                                          791

<210> SEQ ID NO 56
<211> LENGTH: 263
<212> TYPE: PRT
<213> ORGANISM: artificial sequence

```
<220> FEATURE:
<223> OTHER INFORMATION: amino acid translation of SEQ ID NO:55
<220> FEATURE:
<221> NAME/KEY: misc_feature
<222> LOCATION: (66)..(70)
<223> OTHER INFORMATION: Xaa can be any naturally occurring amino acid
<220> FEATURE:
<221> NAME/KEY: misc_feature
<222> LOCATION: (87)..(88)
<223> OTHER INFORMATION: Xaa can be any naturally occurring amino acid

<400> SEQUENCE: 56

Pro Trp Arg Ile Thr Leu Lys Glu Ser Gly Pro Pro Leu Val Lys Pro
1               5                   10                  15

Thr Gln Thr Leu Thr Leu Thr Cys Ser Phe Ser Gly Phe Ser Leu Ser
            20                  25                  30

Asp Phe Gly Val Gly Val Gly Trp Ile Arg Gln Pro Pro Gly Lys Ala
        35                  40                  45

Leu Glu Trp Leu Ala Ile Ile Tyr Ser Asp Asp Asp Lys Arg Tyr Ser
    50                  55                  60

Pro Xaa Xaa Xaa Xaa Xaa Leu Thr Ile Thr Lys Asp Thr Ser Lys Asn
65                  70                  75                  80

Gln Val Val Leu Val Met Xaa Xaa Val Ser Pro Val Asp Thr Ala Thr
                85                  90                  95

Tyr Phe Cys Ala His Arg Arg Gly Pro Thr Thr Leu Phe Gly Val Pro
            100                 105                 110

Ile Ala Arg Gly Pro Val Asn Ala Met Asp Val Trp Gly Gln Gly Ile
        115                 120                 125

Thr Val Thr Ile Ser Ser Gly Gly Gly Ser Gly Gly Gly Gly Ser
    130                 135                 140

Gly Gly Gly Gly Ser Ala Leu Gln Leu Thr Gln Ser Pro Ser Ser Leu
145                 150                 155                 160

Ser Ala Ser Val Gly Asp Arg Ile Thr Ile Thr Cys Arg Ala Ser Gln
                165                 170                 175

Gly Val Thr Ser Ala Leu Ala Trp Tyr Arg Gln Lys Pro Gly Ser Pro
            180                 185                 190

Pro Gln Leu Leu Ile Tyr Asp Ala Ser Ser Leu Glu Ser Gly Val Pro
        195                 200                 205

Ser Arg Phe Ser Gly Ser Gly Ser Gly Thr Glu Phe Thr Leu Thr Ile
    210                 215                 220

Ser Thr Leu Arg Pro Glu Asp Phe Ala Thr Tyr Tyr Cys Gln Gln Leu
225                 230                 235                 240

His Phe Tyr Pro His Thr Phe Gly Gly Gly Thr Arg Val Asp Val Arg
                245                 250                 255

Arg Thr Val Ala Ala Ala Ala
            260

<210> SEQ ID NO 57
<211> LENGTH: 791
<212> TYPE: DNA
<213> ORGANISM: artificial sequence
<220> FEATURE:
<223> OTHER INFORMATION: scFv 2F5 wt synthetic gene library 2
      (VH-Linker-VL)
<220> FEATURE:
<221> NAME/KEY: misc_feature
<222> LOCATION: (37)..(38)
<223> OTHER INFORMATION: n is a, c, g, or t
```

```
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (259)..(260)
<223> OTHER INFORMATION: n is a, c, g, or t
<220> FEATURE:
<221> NAME/KEY: misc_feature
<222> LOCATION: (262)..(263)
<223> OTHER INFORMATION: n is a, c, g, or t

<400> SEQUENCE: 57
ccatggcgga tcaccctgaa agagagtgga cccccnnsn nsnnscctnn snnsnnsctg    60
actctgactt gctcatttag cggctttagc ctgagcgatt ttggcgtcgg cgttggttgg   120
attcgccagc ctcccggcaa agccctggaa tggctggcca tcatctactc cgatgatgac   180
aagcgttata gccccctcgct gaataccgt ctgaccatca ccaaagatac gagcaagaac   240
caggtggttt tggtaatgnn snnsgtgagc cccgtcgaca ccgcgactta tttctgtgcc   300
catcgtcgtg gtccgaccac cctgtttggt gtgccgattg cacgcggtcc cgtgaatgcg   360
atggatgtgt gggggcaggg gattaccgtg accatttcat ccggtggagg tggtagtgga   420
gggggtgggt caggcggtgg cggctccgcc ttacaactga cgcagagccc gtctagtttg   480
agcgcaagcg tgggcgatcg tattacaatt acctgtcggg cgagccaagg tgttacctcc   540
gccctggcct ggtatcgtca gaaacccggg agcccgccac agttgttgat ctacgatgcg   600
tcctcactgg aatcaggggt ccctagccgc ttttcgggt ccggcagcgg cacggaattt    660
acattgacca taagcaccct gcgtccggaa gattttgcca cctattattg ccaacagctg   720 cactttatc cccataacctt cggtgggggg acgcgggttg acgtgcgtcg taccgtagct   780
gctgcggccg c                                                        791

<210> SEQ ID NO 58
<211> LENGTH: 263
<212> TYPE: PRT
<213> ORGANISM: artificial sequence
<220> FEATURE:
<223> OTHER INFORMATION: amino acid translation of SEQ ID NO:57
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (87)..(88)
<223> OTHER INFORMATION: Xaa can be any naturally occurring amino acid
```

<400> SEQUENCE: 58

Pro Trp Arg Ile Thr Leu Lys Glu Ser Gly Pro Pro Xaa Xaa Xaa Pro
1               5                   10                  15

Xaa Xaa Xaa Leu Thr Leu Thr Cys Ser Phe Ser Gly Phe Ser Leu Ser
            20                  25                  30

Asp Phe Gly Val Gly Val Gly Trp Ile Arg Gln Pro Pro Gly Lys Ala
            35                  40                  45

Leu Glu Trp Leu Ala Ile Ile Tyr Ser Asp Asp Lys Arg Tyr Ser
50                  55                  60

Pro Ser Leu Asn Thr Arg Leu Thr Ile Thr Lys Asp Thr Ser Lys Asn
65                  70                  75                  80

Gln Val Val Leu Val Met Xaa Xaa Val Ser Pro Val Asp Thr Ala Thr
                85                  90                  95

Tyr Phe Cys Ala His Arg Arg Gly Pro Thr Thr Leu Phe Gly Val Pro
            100                 105                 110

Ile Ala Arg Gly Pro Val Asn Ala Met Asp Val Trp Gly Gln Gly Ile
            115                 120                 125

Thr Val Thr Ile Ser Ser Gly Gly Gly Gly Ser Gly Gly Gly Gly Ser
130                 135                 140

Gly Gly Gly Gly Ser Ala Leu Gln Leu Thr Gln Ser Pro Ser Ser Leu
145                 150                 155                 160

Ser Ala Ser Val Gly Asp Arg Ile Thr Ile Thr Cys Arg Ala Ser Gln
                165                 170                 175

Gly Val Thr Ser Ala Leu Ala Trp Tyr Arg Gln Lys Pro Gly Ser Pro
            180                 185                 190

Pro Gln Leu Leu Ile Tyr Asp Ala Ser Ser Leu Glu Ser Gly Val Pro
            195                 200                 205

Ser Arg Phe Ser Gly Ser Gly Ser Gly Thr Glu Phe Thr Leu Thr Ile
210                 215                 220

Ser Thr Leu Arg Pro Glu Asp Phe Ala Thr Tyr Tyr Cys Gln Gln Leu
225                 230                 235                 240

His Phe Tyr Pro His Thr Phe Gly Gly Gly Thr Arg Val Asp Val Arg
            245                 250                 255

Arg Thr Val Ala Ala Ala Ala
            260

<210> SEQ ID NO 59
<211> LENGTH: 791
<212> TYPE: DNA
<213> ORGANISM: artificial sequence
<220> FEATURE:
<223> OTHER INFORMATION: scFv 2F5 wt synthetic gene library 3
      (VH-Linker-VL)
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (196)..(197)
<223> OTHER INFORMATION: n is a, c, g, or t
<220> FEATURE:
<221> NAME/KEY: misc_feature
<222> LOCATION: (199)..(200)
<223> OTHER INFORMATION: n is a, c, g, or t
<220> FEATURE:
<221> NAME/KEY: misc_feature
<222> LOCATION: (202)..(203)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (208)..(209)
<223> OTHER INFORMATION: n is a, c, g, or t
<220> FEATURE:
<221> NAME/KEY: misc_feature
<222> LOCATION: (259)..(260)
<223> OTHER INFORMATION: n is a, c, g, or t
<220> FEATURE:
<221> NAME/KEY: misc_feature
<222> LOCATION: (262)..(263)
<223> OTHER INFORMATION: n is a, c, g, or t

<400> SEQUENCE: 59

```
ccatggcgga tcaccctgaa agagagtgga ccccccnnsn nsnnsc ctnn snnsnnsctg    60
actctgactt gctcatttag cggctttagc ctgagcgatt ttggcgtcgg cgttggttgg   120
attcgccagc ctcccggcaa agccctggaa tggctggcca tcatctactc cgatgatgac   180
aagcgttata gccccnnsnn snnsnnsnns ctgaccatca ccaaagatac gagcaagaac   240
caggtggttt tggtaatgnn snnsgtgagc cccgtcgaca ccgcgactta tttctgtgcc   300
catcgtcgtg gtccgaccac cctgtttggt gtgccgattg cacgcggtcc cgtgaatgcg   360
atggatgtgt gggggcaggg gattaccgtg accatttcat ccggtggagg tggtagtgga   420
gggggtgggt caggcggtgg cggctccgcc ttacaactga cgcagagccc gtctagtttg   480
agcgcaagcg tgggcgatcg tattacaatt acctgtcggg cgagccaagg tgttacctcc   540
gccctggcct ggtatcgtca gaaacccggg agcccgccac agttgttgat ctacgatgcg   600
tcctcactgg aatcagggg t ccctagccgc ttttccgggt ccggcagcgg cacggaattt   660
acattgacca taagcaccct gcgtccggaa gattttgcca cctattattg ccaacagctg   720
cacttttatc cccatacctt cggtgggggg acgcgggttg acgtgcgtcg taccgtagct   780
gctgcggccg c                                                         791
```

<210> SEQ ID NO 60
<211> LENGTH: 263
<212> TYPE: PRT
<213> ORGANISM: artificial sequence
<220> FEATURE:
<223> OTHER INFORMATION: amino acid translation of SEQ ID NO:59
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (66)..(70)
<223> OTHER INFORMATION: Xaa can be any naturally occurring amino acid
<220> FEATURE:
<221> NAME/KEY: misc_feature
<222> LOCATION: (87)..(88)
<223> OTHER INFORMATION: Xaa can be any naturally occurring amino acid

<400> SEQUENCE: 60

Pro Trp Arg Ile Thr Leu Lys Glu Ser Gly Pro Pro Xaa Xaa Xaa Pro
1               5                   10                  15

Xaa Xaa Xaa Leu Thr Leu Thr Cys Ser Phe Ser Gly Phe Ser Leu Ser
            20                  25                  30

Asp Phe Gly Val Gly Val Gly Trp Ile Arg Gln Pro Pro Gly Lys Ala
        35                  40                  45

Leu Glu Trp Leu Ala Ile Ile Tyr Ser Asp Asp Lys Arg Tyr Ser
    50                  55                  60

Pro Xaa Xaa Xaa Xaa Xaa Leu Thr Ile Thr Lys Asp Thr Ser Lys Asn
65                  70                  75                  80

Gln Val Val Leu Val Met Xaa Xaa Val Ser Pro Val Asp Thr Ala Thr
                85                  90                  95

Tyr Phe Cys Ala His Arg Arg Gly Pro Thr Thr Leu Phe Gly Val Pro
            100                 105                 110

Ile Ala Arg Gly Pro Val Asn Ala Met Asp Val Trp Gly Gln Gly Ile
        115                 120                 125

Thr Val Thr Ile Ser Ser Gly Gly Gly Gly Ser Gly Gly Gly Gly Ser
    130                 135                 140

Gly Gly Gly Gly Ser Ala Leu Gln Leu Thr Gln Ser Pro Ser Ser Leu
145                 150                 155                 160

Ser Ala Ser Val Gly Asp Arg Ile Thr Ile Thr Cys Arg Ala Ser Gln
                165                 170                 175

Gly Val Thr Ser Ala Leu Ala Trp Tyr Arg Gln Lys Pro Gly Ser Pro
            180                 185                 190

Pro Gln Leu Leu Ile Tyr Asp Ala Ser Ser Leu Glu Ser Gly Val Pro
        195                 200                 205

Ser Arg Phe Ser Gly Ser Gly Ser Gly Thr Glu Phe Thr Leu Thr Ile
    210                 215                 220

Ser Thr Leu Arg Pro Glu Asp Phe Ala Thr Tyr Tyr Cys Gln Gln Leu
225                 230                 235                 240

His Phe Tyr Pro His Thr Phe Gly Gly Gly Thr Arg Val Asp Val Arg
                245                 250                 255

Arg Thr Val Ala Ala Ala Ala
            260

<210> SEQ ID NO 61
<211> LENGTH: 791
<212> TYPE: DNA
<213> ORGANISM: artificial sequence
<220> FEATURE:
<223> OTHER INFORMATION: scFv 2F5 wild-type synthetic gene

<400> SEQUENCE: 61
ccatggcgga tcaccctgaa agagagtgga ccccccctgg tgaaacctac ccagaccctg      60
actctgactt gctcatttag cggctttagc ctgagcgatt ttggcgtcgg cgttggttgg     120

```
attcgccagc ctcccggcaa agccctggaa tggctggcca tcatctactc cgatgatgac    180
aagcgttata gcccctcgct gaataccgt ctgaccatca ccaaagatac gagcaagaac    240
caggtggttt tggtaatgac ccgtgtgagc cccgtcgaca ccgcgactta tttctgtgcc    300
catcgtcgtg gtccgaccac cctgtttggt gtgccgattg cacgcggtcc cgtgaatgcg    360
atggatgtgt gggggcaggg gattaccgtg accatttcat ccggtggagg tggtagtgga    420
gggggtgggt caggcggtgg cggctccgcc ttacaactga gcagagccc gtctagtttg    480
agcgcaagcg tgggcgatcg tattacaatt acctgtcggg cgagccaagg tgttacctcc    540
gccctggcct ggtatcgtca gaaacccggg agcccgccac agttgttgat ctacgatgcg    600
tcctcactgg aatcagggt ccctagccgc ttttccgggt ccggcagcgg cacggaattt    660
acattgacca taagcaccct gcgtccggaa gattttgcca cctattattg ccaacagctg    720
cactttatc cccataccct cggtgggggg acgcgggttg acgtgcgtcg taccgtagct    780
gctgcggccg c                                                        791
```

<210> SEQ ID NO 62
<211> LENGTH: 263
<212> TYPE: PRT
<213> ORGANISM: artificial sequence
<220> FEATURE:
<223> OTHER INFORMATION: amino acid translation of SEQ ID NO:61

<400> SEQUENCE: 62

```
Pro Trp Arg Ile Thr Leu Lys Glu Ser Gly Pro Pro Leu Val Lys Pro
1               5                   10                  15

Thr Gln Thr Leu Thr Leu Thr Cys Ser Phe Ser Gly Phe Ser Leu Ser
            20                  25                  30

Asp Phe Gly Val Gly Val Gly Trp Ile Arg Gln Pro Pro Gly Lys Ala
        35                  40                  45

Leu Glu Trp Leu Ala Ile Ile Tyr Ser Asp Asp Lys Arg Tyr Ser
    50                  55                  60

Pro Ser Leu Asn Thr Arg Leu Thr Ile Thr Lys Asp Thr Ser Lys Asn
65                  70                  75                  80

Gln Val Val Leu Val Met Thr Arg Val Ser Pro Val Asp Thr Ala Thr
                85                  90                  95

Tyr Phe Cys Ala His Arg Arg Gly Pro Thr Thr Leu Phe Gly Val Pro
            100                 105                 110

Ile Ala Arg Gly Pro Val Asn Ala Met Asp Val Trp Gly Gln Gly Ile
        115                 120                 125

Thr Val Thr Ile Ser Ser Gly Gly Gly Ser Gly Gly Gly Gly Ser
    130                 135                 140

Gly Gly Gly Gly Ser Ala Leu Gln Leu Thr Gln Ser Pro Ser Ser Leu
145                 150                 155                 160

Ser Ala Ser Val Gly Asp Arg Ile Thr Ile Thr Cys Arg Ala Ser Gln
                165                 170                 175

Gly Val Thr Ser Ala Leu Ala Trp Tyr Arg Gln Lys Pro Gly Ser Pro
            180                 185                 190

Pro Gln Leu Leu Ile Tyr Asp Ala Ser Ser Leu Glu Ser Gly Val Pro
        195                 200                 205

Ser Arg Phe Ser Gly Ser Gly Ser Gly Thr Glu Phe Thr Leu Thr Ile
    210                 215                 220

Ser Thr Leu Arg Pro Glu Asp Phe Ala Thr Tyr Tyr Cys Gln Gln Leu
225                 230                 235                 240
```

-continued

```
His Phe Tyr Pro His Thr Phe Gly Gly Gly Thr Arg Val Asp Val Arg
            245                 250                 255

Arg Thr Val Ala Ala Ala Ala
            260
```